(12) United States Patent
Dueck et al.

(10) Patent No.: US 11,890,438 B1
(45) Date of Patent: Feb. 6, 2024

(54) THERAPEUTIC SUBSTANCE DELIVERY

(71) Applicants: Wolfram Frederik Dueck, Hannover (DE); Daniel Smyth, Mechelen (BE)

(72) Inventors: Wolfram Frederik Dueck, Hannover (DE); Daniel Smyth, Mechelen (BE)

(73) Assignee: Cochlear Limited, Macquarie University (AU)

(*) Notice: Subject to any disclaimer, the term of this patent is extended or adjusted under 35 U.S.C. 154(b) by 472 days.

(21) Appl. No.: 17/019,619

(22) Filed: Sep. 14, 2020

Related U.S. Application Data

(60) Provisional application No. 62/899,265, filed on Sep. 12, 2019.

(51) Int. Cl.
*A61M 31/00* (2006.01)
*A61N 1/05* (2006.01)

(52) U.S. Cl.
CPC .......... *A61M 31/00* (2013.01); *A61N 1/0541* (2013.01); *A61M 2205/05* (2013.01); *A61M 2210/0668* (2013.01)

(58) Field of Classification Search
CPC .............. A61M 31/00; A61M 25/007; A61M 2025/0024; A61M 2025/0025; A61M 2025/1065; A61M 2210/0662; A61M 2210/0668; A61M 2210/0675; A61M 2210/0681; A61M 2210/0687; A61M 2210/0693; A61M 2205/05; A61M 2025/1015; A61M 25/0119; A61M 35/00; A61M 37/00; A61F 11/04; A61F 11/045; A61N 1/36036; A61N 1/36038; A61N 1/0541
See application file for complete search history.

(56) References Cited

U.S. PATENT DOCUMENTS

| | | | | |
|---|---|---|---|---|
| 4,043,345 A | * | 8/1977 | Kramann | A61M 25/0119 604/523 |
| 4,887,996 A | * | 12/1989 | Bengmark | A61M 27/008 604/528 |
| 5,421,818 A | | 6/1995 | Arenberg | |
| 6,045,528 A | | 4/2000 | Arenberg et al. | |
| 6,377,849 B1 | | 4/2002 | Lenarz et al. | |
| 6,575,932 B1 | * | 6/2003 | O'Brien | A61M 25/007 604/101.01 |
| 6,648,873 B2 | | 11/2003 | Arenberg et al. | |

(Continued)

FOREIGN PATENT DOCUMENTS

WO 2016149561 A1 9/2016

OTHER PUBLICATIONS

Andrew M. Ayoob et al., "The role of intracochlear drug delivery devices in the management of inner ear disease," Expert Opin. Drug Deliv., Jan. 2015, pp. 465-479, vol. 12, No. 3.

*Primary Examiner* — Nilay J Shah
(74) *Attorney, Agent, or Firm* — Pilloff Passino & Cosenza LLP; Martin J. Cosenza

(57) ABSTRACT

An apparatus including a therapeutic substance delivery device configured for attachment to a first tissue area internal of a recipient, the delivery device configured to enable movement of a therapeutic substance outlet of the delivery device proximate a second tissue area away from the first tissue area after attachment to the first tissue area to deliver the therapeutic substance from the outlet while implanted in the recipient.

35 Claims, 25 Drawing Sheets

(56) References Cited

U.S. PATENT DOCUMENTS

| | | | |
|---|---|---|---|
| 6,659,996 B1* | 12/2003 | Kaldany | A61M 37/0069 604/509 |
| 7,650,194 B2 | 1/2010 | Fritsch et al. | |
| 8,750,988 B2* | 6/2014 | Jolly | A61M 31/002 604/28 |
| 2003/0097121 A1* | 5/2003 | Jolly | A61F 11/00 604/20 |
| 2004/0078057 A1* | 4/2004 | Gibson | A61N 1/0541 607/3 |
| 2005/0033377 A1* | 2/2005 | Milojevic | A61N 1/36038 607/45 |
| 2006/0287689 A1* | 12/2006 | Debruyne | A61P 41/00 607/57 |
| 2007/0088335 A1* | 4/2007 | Jolly | A61N 1/0541 604/891.1 |
| 2009/0149833 A1* | 6/2009 | Cima | A61P 23/02 604/93.01 |
| 2010/0030130 A1* | 2/2010 | Parker | A61N 1/36038 604/20 |
| 2010/0106134 A1 | 4/2010 | Jolly et al. | |
| 2011/0112462 A1* | 5/2011 | Parker | H04R 25/70 604/20 |
| 2012/0078362 A1 | 3/2012 | Haffner et al. | |
| 2013/0289467 A1 | 10/2013 | Haffner et al. | |
| 2013/0338700 A1* | 12/2013 | Matheny | A61F 2/186 606/199 |
| 2014/0031852 A1* | 1/2014 | Edgren | A61B 17/24 606/199 |
| 2015/0374964 A1* | 12/2015 | Verhoeven | A61M 5/14276 604/247 |
| 2017/0367892 A1* | 12/2017 | Kim | A61M 31/00 |

\* cited by examiner

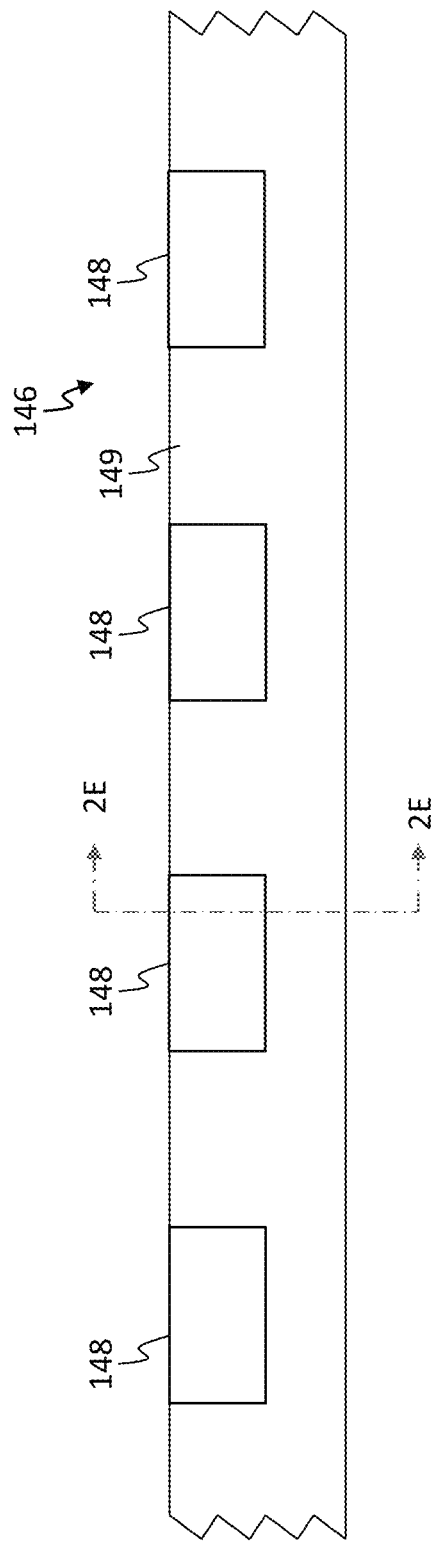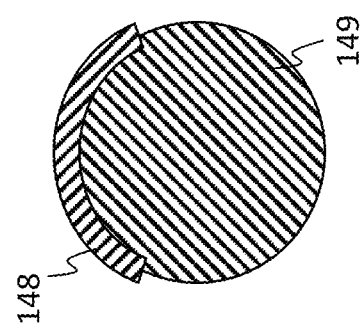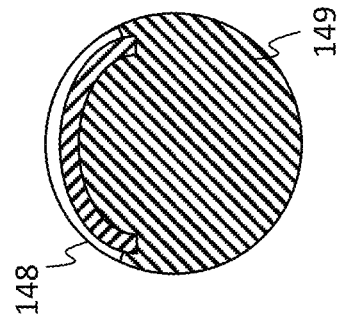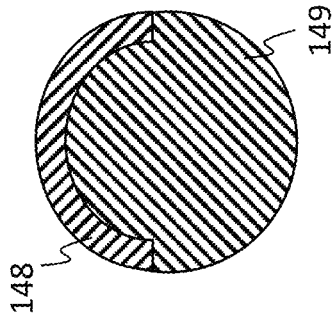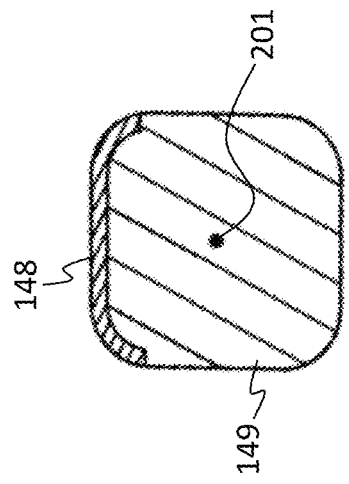

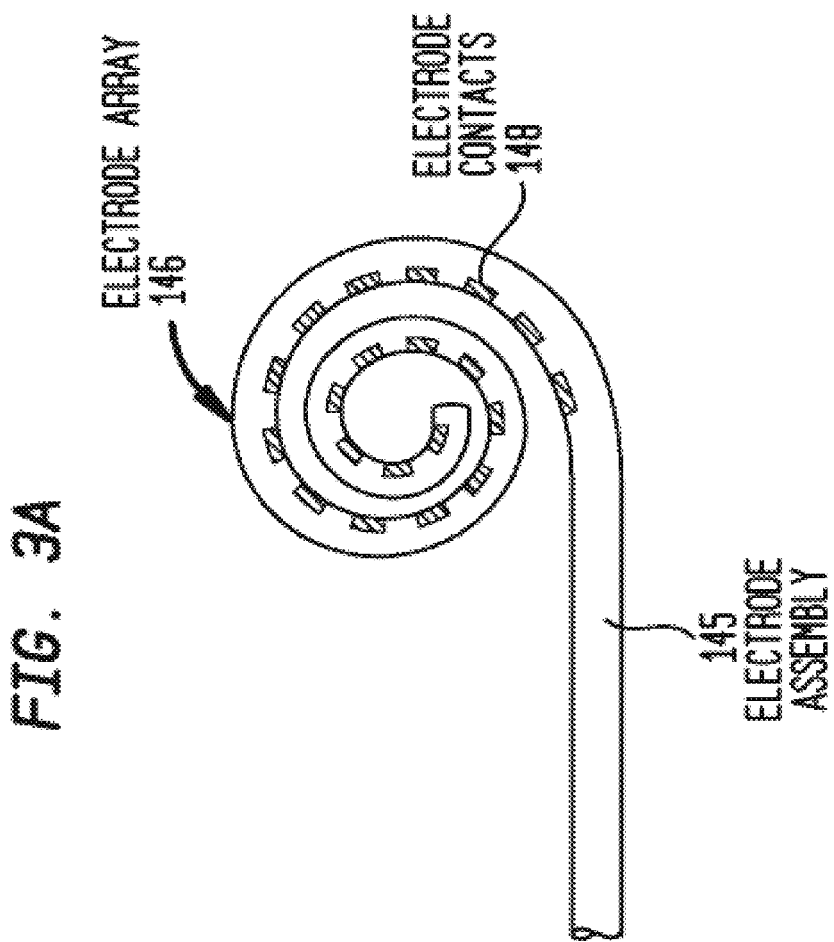

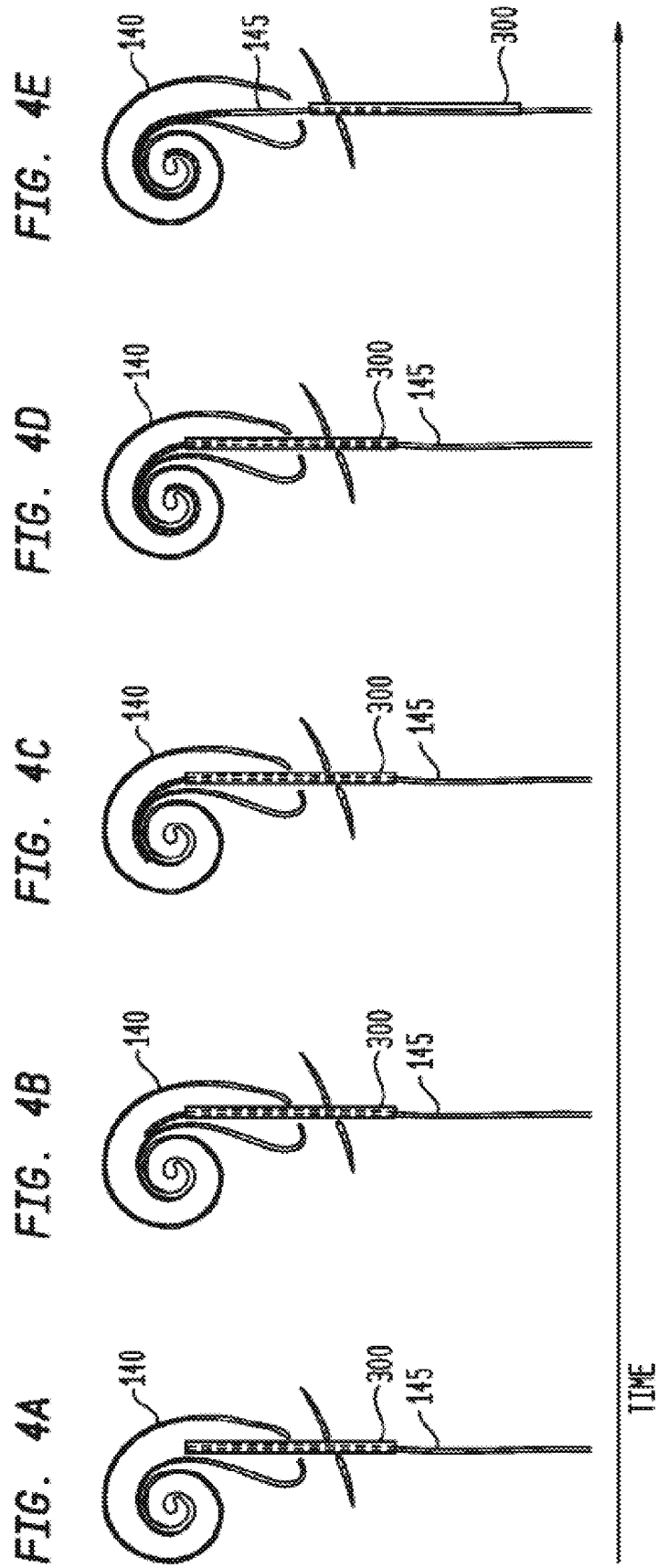

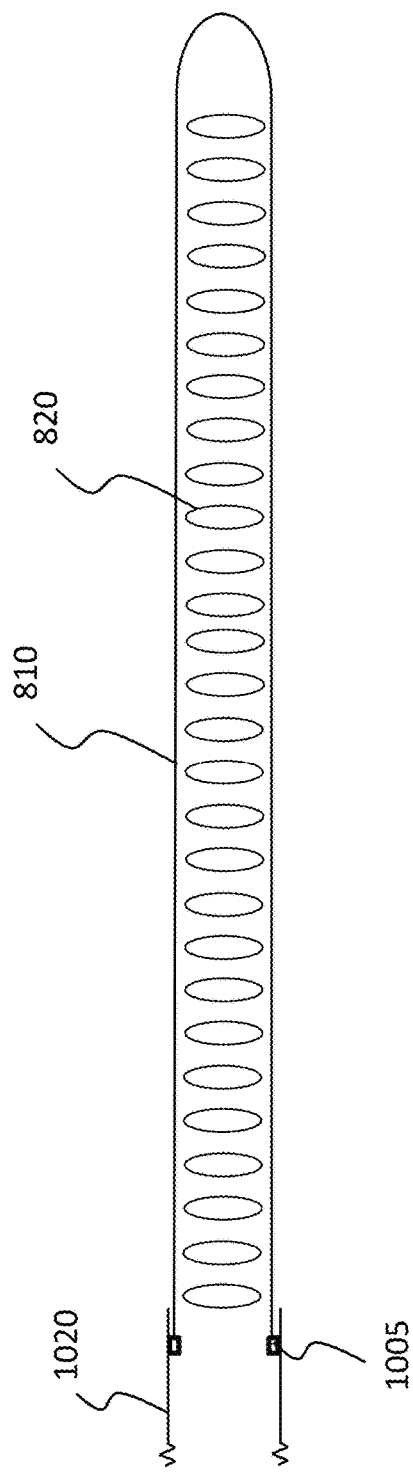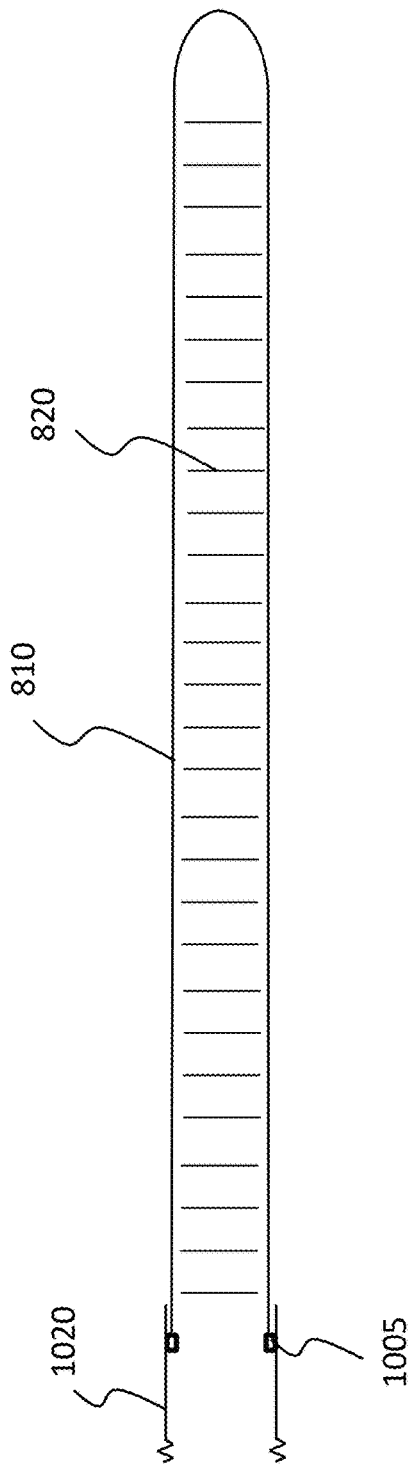

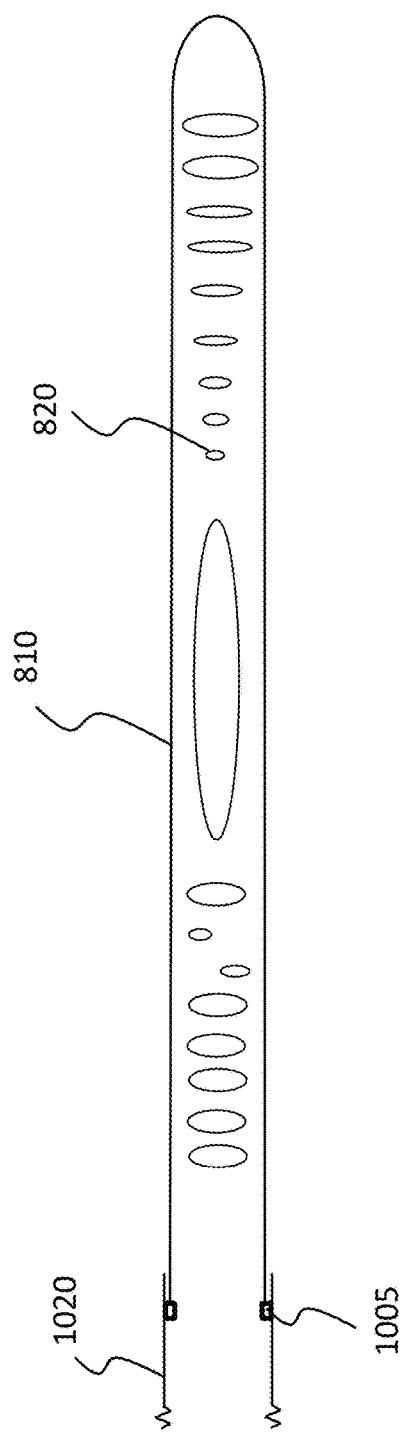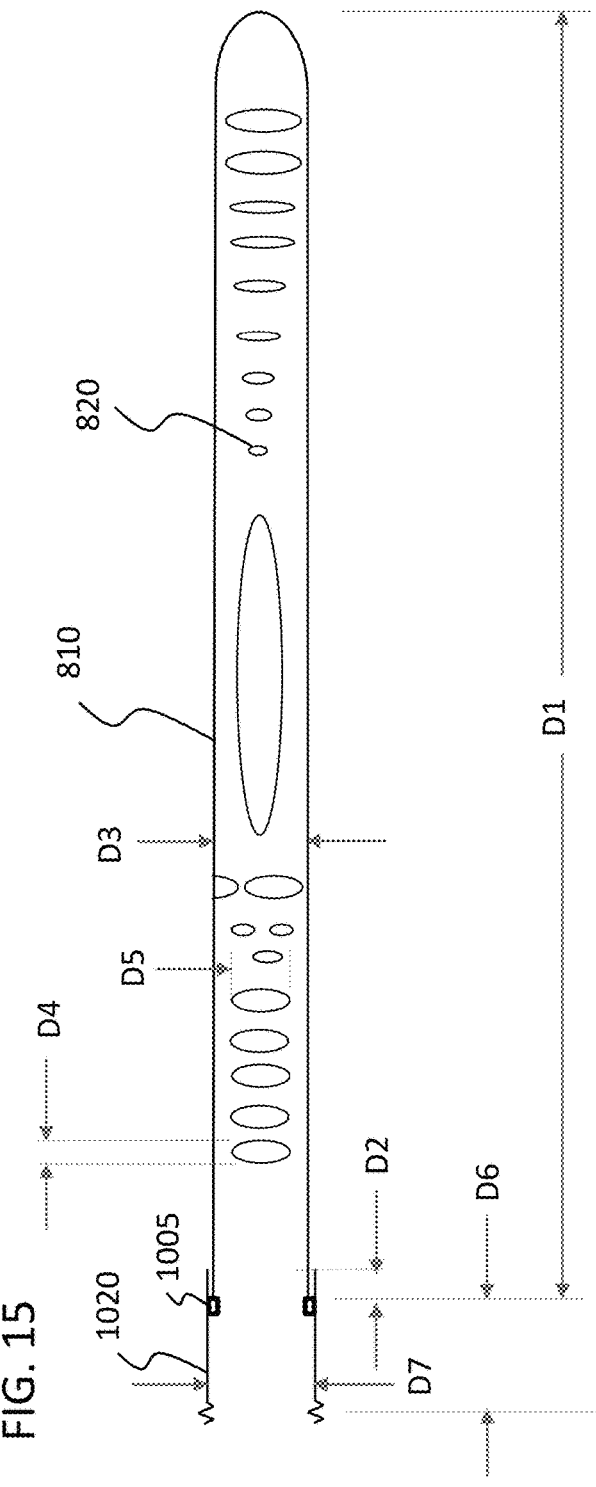

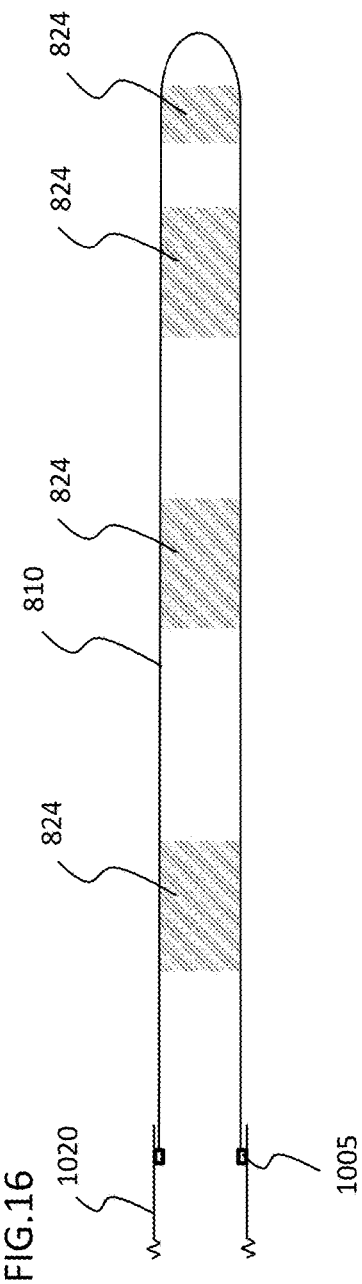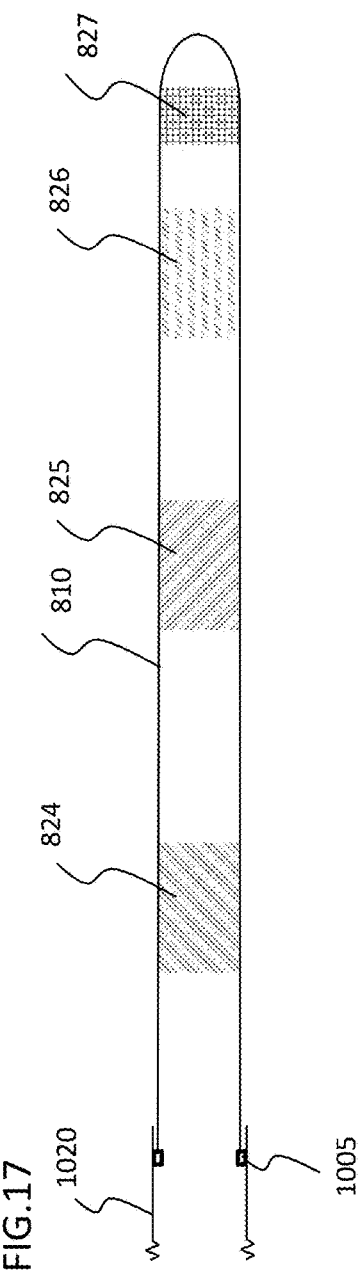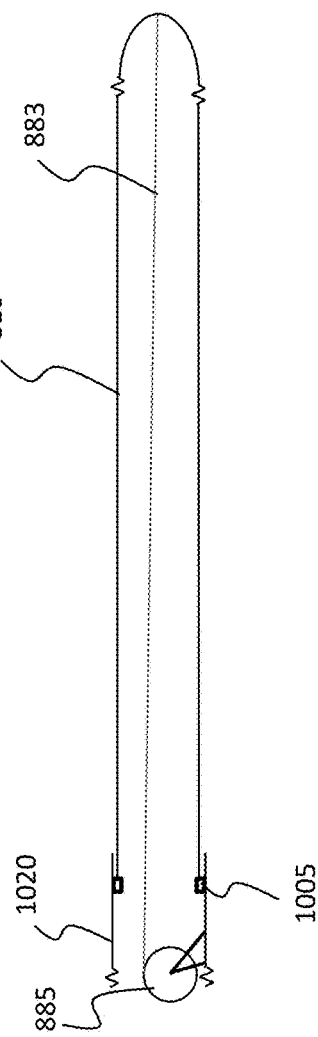

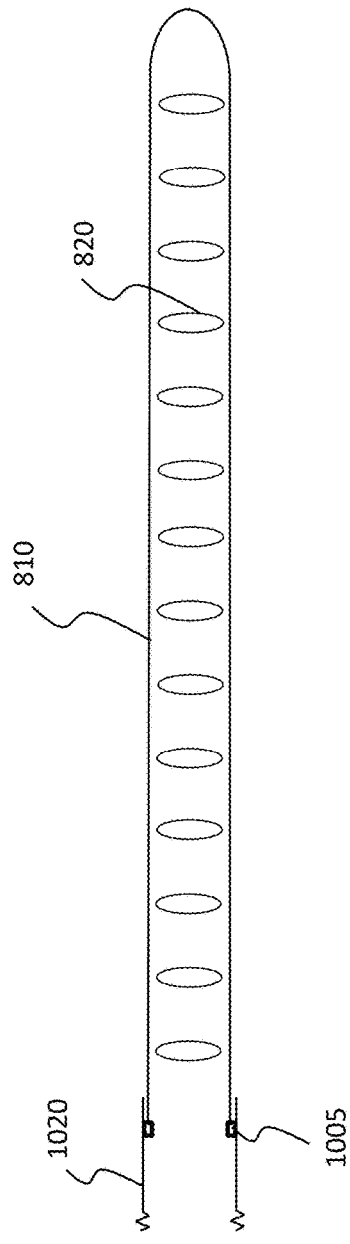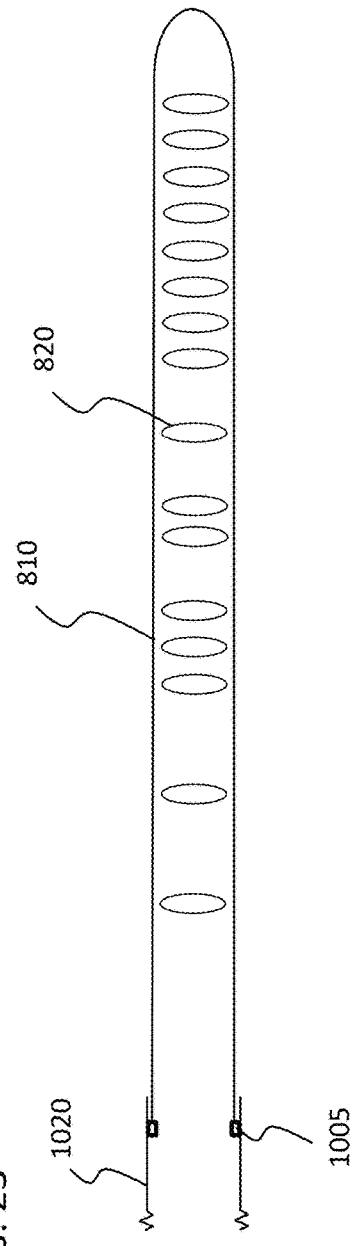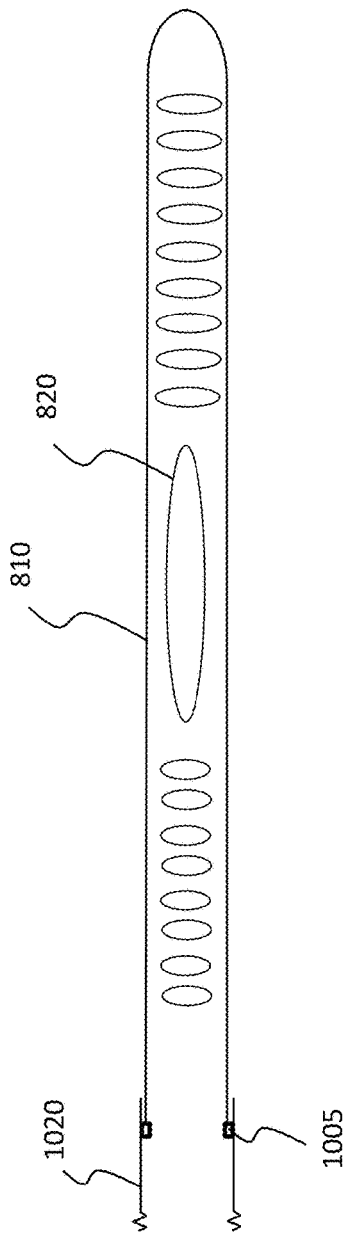

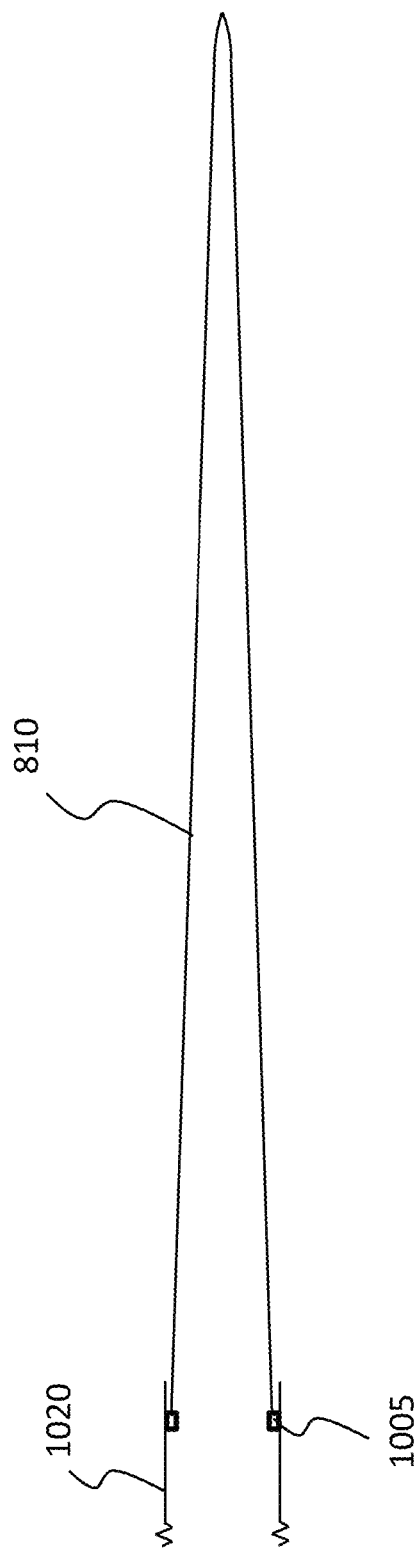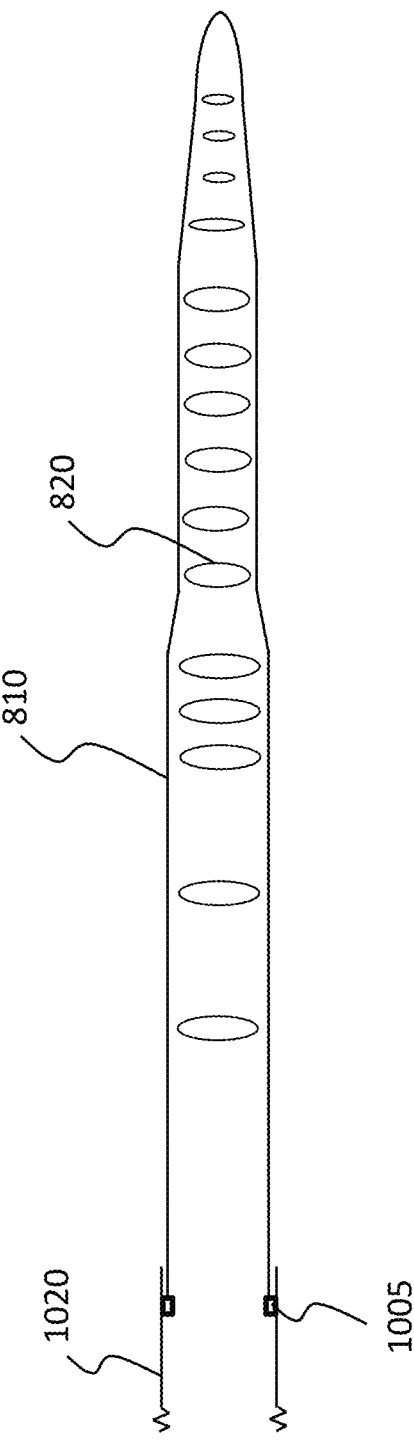

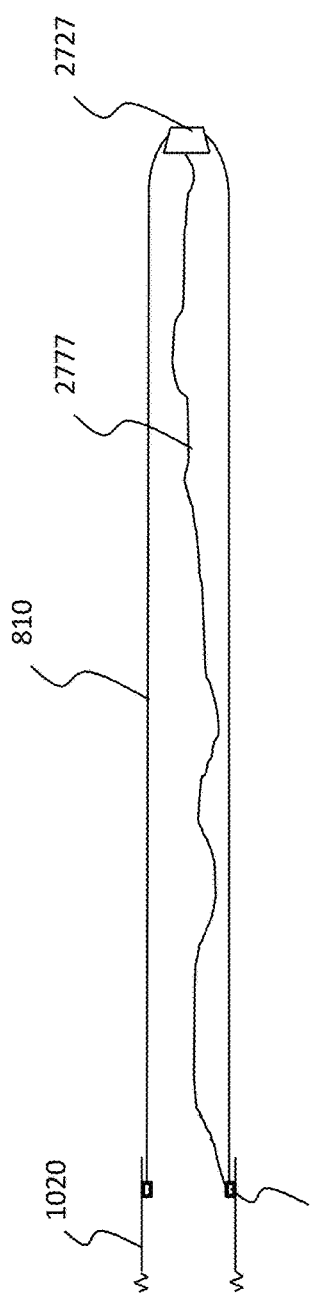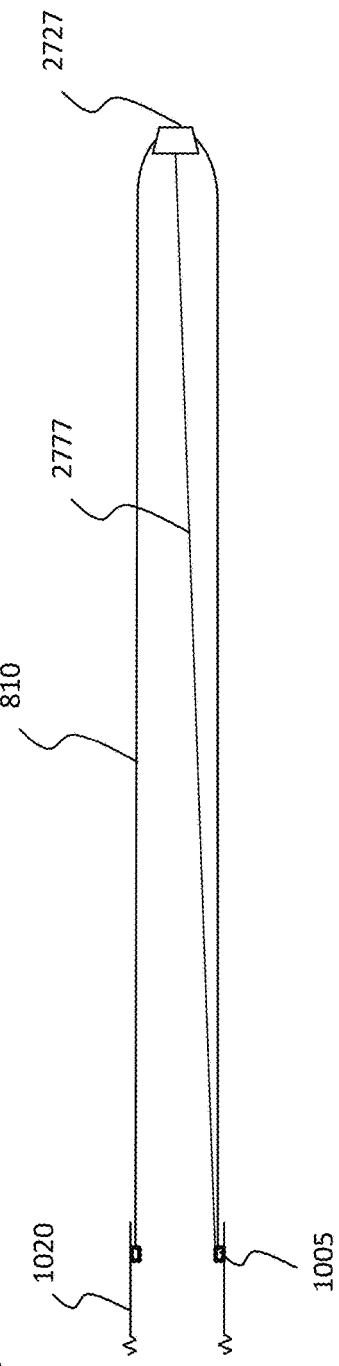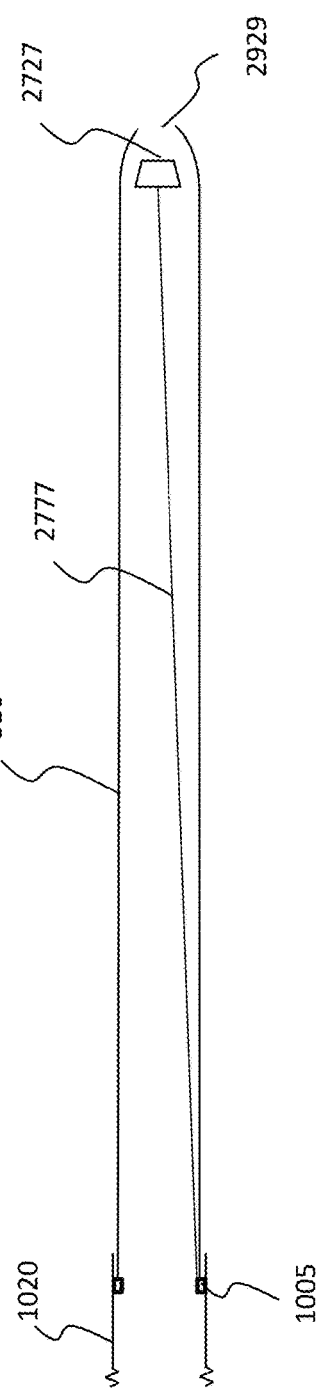

THERAPEUTIC SUBSTANCE DELIVERY

CROSS-REFERENCE TO RELATED APPLICATIONS

This application claims priority to Provisional U.S. Patent Application No. 62/899,265, entitled THERAPEUTIC SUBSTANCE DELIVERY, filed on Sep. 12, 2019, naming Wolfram Frederik DUECK of Hannover, Germany as an inventor, the entire contents of that application being incorporated herein by reference in its entirety.

BACKGROUND

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions and/or recipient monitoring for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In accordance with an exemplary embodiment, there is an apparatus, comprising a therapeutic substance delivery device configured for attachment to a first tissue area internal of a recipient, the delivery device configured to enable movement of a therapeutic substance outlet of the delivery device proximate a second tissue area away from the first tissue area after attachment to the first tissue area to deliver the therapeutic substance from the outlet while implanted in the recipient.

In accordance with an exemplary embodiment, there is an apparatus, comprising a first structure configured to be attached to tissue internal of a recipient, and a second structure configured to be supported by the first structure in an initial state during a first temporal period, and configured to be deployed from the first structure in a deployed state during a second temporal period after the first temporal period, wherein the apparatus is a therapeutic substance delivery device configured to deliver therapeutic substance from the second structure to a location remote from the first structure during and/or after deployment of the second structure, and the second structure is at least one of in or controllably placeable in fluid communication with the first structure so that therapeutic substance can travel from the first structure to the second structure.

In accordance with an exemplary embodiment, there is an apparatus, comprising a means for securing the apparatus to tissue, and a means for delivering therapeutic substance inside a cochlea.

In accordance with an exemplary embodiment, there is a method, comprising, from a fixed location inside a recipient, deploying an outlet of a therapeutic substance delivery device to a location remote from the fixed location while another part of the therapeutic substance delivery device is stationary relative to the fixed location so that the outlet is proximate tissue remote from the fixed location; and delivering therapeutic substance from the outlet after deployment.

BRIEF DESCRIPTION OF THE DRAWINGS

Embodiments are described below with reference to the attached drawings, in which:

FIGS. 2A-2H are views of exemplary electrode arrays to which the teachings detailed herein can be applicable;

FIGS. 3A and 3B are side and perspective views of an electrode assembly extended out of an embodiment of an insertion sheath of the insertion tool illustrated in FIG. 2;

FIGS. 4A-4E are simplified side views depicting an exemplary insertion process of the electrode assembly into the cochlea;

FIGS. 12-18 and 22-26 depict exemplary deployment apparatuses;

FIGS. 27-29 depict exemplary outlet opening; and

DETAILED DESCRIPTION

Merely for ease of description, the techniques presented herein for location-based selection of processing settings are primarily described herein with reference to an illustrative medical device, namely a cochlear implant. However, it is to be appreciated that the techniques presented herein may also be used with a variety of other medical devices that, while providing a wide range of therapeutic benefits to recipients, patients, or other users, may benefit from setting changes based on the location of the medical device. For example, the techniques presented herein can be used with other hearing prostheses, including acoustic hearing aids, bone conduction devices, middle ear auditory prostheses, direct acoustic stimulators, other electrically simulating auditory prostheses (e.g., auditory brain stimulators), etc. The techniques presented herein can also be used with vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation, etc. Thus, embodiments include methods that include one or more of the just-detailed treatments and/or usages of the one or more just detailed apparatuses in combination with any one or more of the teachings herein. Also, embodiments include apparatuses and/or systems that include devices or sub-systems that are for one or more of the just-detailed treatments and/or usages of the one or more just detailed apparatuses in combination with any one or more of the teachings herein.

Figure 1:
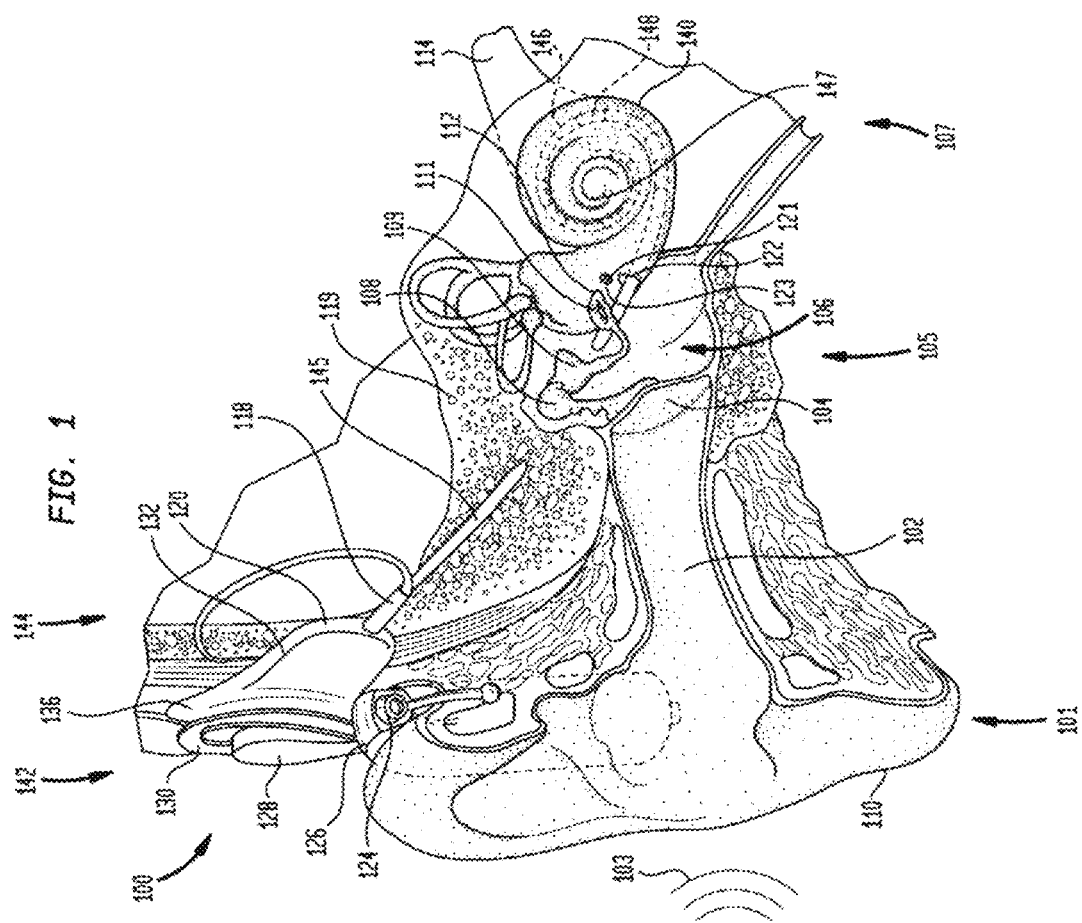
FIG. 1 is a perspective view of an exemplary hearing prosthesis.

FIG. 1 is a perspective view of an exemplary cochlear implant 100 implanted in a recipient having an outer ear 101, a middle ear 105, and an inner ear 107. In a fully functional ear, outer ear 101 comprises an auricle 110 and an ear canal 102. It is briefly noted that while some embodiments focused upon a cochlear implant that utilizes an electrode array, other embodiments can be utilized in combination with other types of implants, such as, for example, a middle ear implant or a direct acoustic cochlear stimulation device. Embodiments include the utilization of the teachings detailed herein with a mechanical actuator device that is located inside the cochlea. Moreover, at least some exemplary embodiments can be utilized with transcutaneous bone conduction devices and/or conventional acoustic hearing aids that are entirely outside the skin of the recipient. Any disclosure of one herein corresponds to a disclosure of any one or more of the others unless otherwise noted.

Acoustic pressure or sound waves 103 are collected by auricle 110 and channeled into and through ear canal 102. Disposed across the distal end of ear canal 102 is a tympanic membrane 104 that vibrates in response to sound waves 103. This vibration is coupled to oval window or fenestra ovalis 112 through the three bones of the middle ear 105, collectively referred to as the ossicles 106, and comprising the malleus 108, the incus 109, and the stapes 111. Ossicles 106 filter and amplify the vibrations delivered by tympanic membrane 104, causing oval window 112 to articulate, or vibrate. This vibration sets up waves of fluid motion of the perilymph within cochlea 140. Such fluid motion, in turn, activates hair cells (not shown) inside the cochlea which in turn causes nerve impulses to be generated which are transferred through spiral ganglion cells (not shown) and auditory nerve 114 to the brain (also not shown) where they are perceived as sound.

The exemplary cochlear implant illustrated in FIG. 1 is a partially-implanted stimulating medical device. Specifically, cochlear implant 100 comprises external components 142 attached to the body of the recipient, and internal or implantable components 144 implanted in the recipient. External components 142 typically comprise one or more sound input elements for detecting sound, such as microphone 124, a sound processor (not shown), and a power source (not shown). Collectively, these components are housed in a behind-the-ear (BTE) device 126 in the example depicted in FIG. 1. External components 142 also include a transmitter unit 128 comprising an external coil 130 of a transcutaneous energy transfer (TET) system. BTE device 126, often referred to as a sound processor processes the output of microphone 124 and generates encoded stimulation data signals which are provided to external coil 130.

Internal components 144 comprise an internal receiver unit 132 including a coil 136 of the TET system, a stimulator unit 120, and an elongate stimulating lead assembly 118. Internal receiver unit 132 and stimulator unit 120 are hermetically sealed within a biocompatible housing commonly referred to as a stimulator/receiver unit. Internal coil 136 of receiver unit 132 receives power and stimulation data from external coil 130. Stimulating lead assembly 118 has a proximal end connected to stimulator unit 120, and extends through mastoid bone 119. Lead assembly 118 has a distal region, referred to as electrode assembly 145, a portion of which is implanted in cochlea 140.

Electrode assembly 145 can be inserted into cochlea 140 via a cochleostomy 122, or through round window 121, oval window 112, promontory 123, or an opening in an apical turn 147 of cochlea 140. Integrated in electrode assembly 145 is an array 146 of longitudinally-aligned and distally extending electrode contacts 148 for stimulating the cochlea by delivering electrical, optical, or some other form of energy. Stimulator unit 120 generates stimulation signals each of which is delivered by a specific electrode contact 148 to cochlea 140, thereby stimulating auditory nerve 114.

Figure 2A:
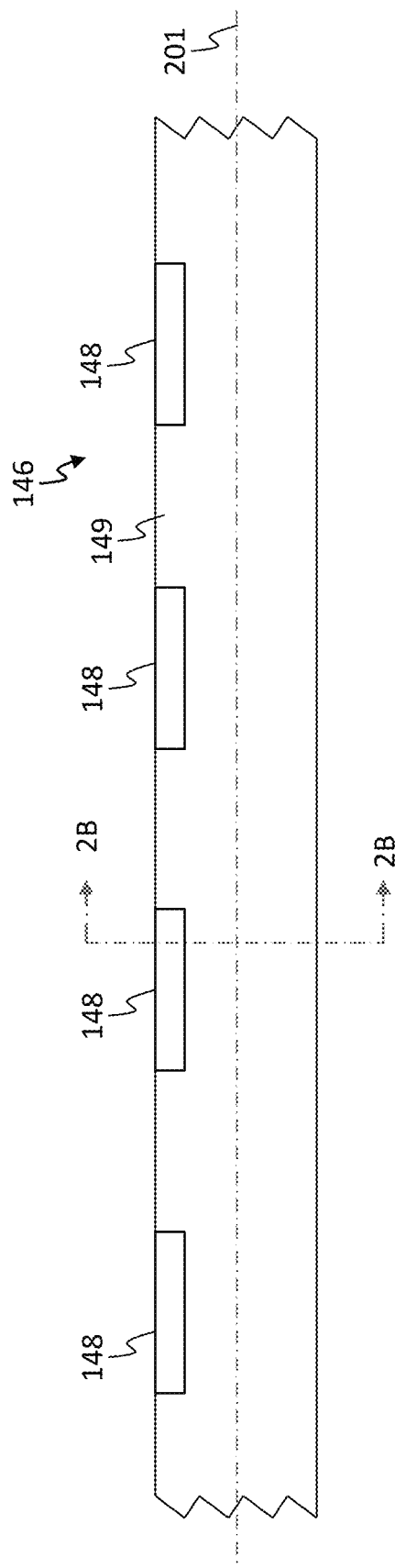
Figure 2C:
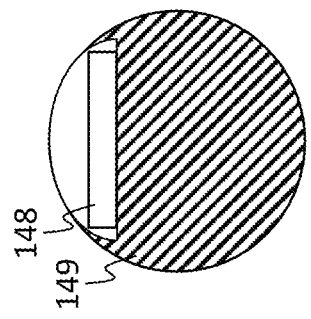
Figure 2B:
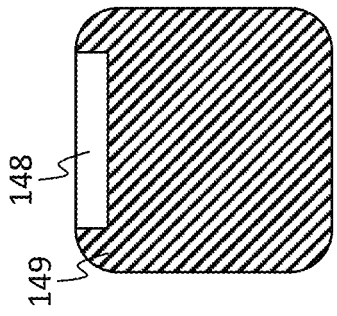

FIG. 2A depicts a conceptual side view of a portion of electrode array 146, depicting four electrode contacts 148 evenly spaced along a longitudinal axis of the electrode array 146. It is noted that in some alternate embodiments, the electrode is not evenly spaced. FIG. 2B depicts a conceptual cross-sectional view through one of the electrode contacts 148, which also depicts the carrier 149 of the electrode contact 148. In an exemplary embodiment, the carrier 149 is made of silicone. Not depicted in the figures are electrical leads and stiffener components that are sometimes embedded in the carrier 149. The embodiment of FIG. 2B represents an electrode array 146 that has a generally rectangular cross-section. FIG. 2C depicts an alternate embodiment where the electrode array 146 has a generally circular cross-section. It is also noted that in some exemplary embodiments, the cross-section is oval shaped. Thus, the embodiment of FIGS. 2A-2C is a species of the genus of an electrode array having a generally continuously curving cross-section. Any electrode array of any cross-section or any configuration can be utilized with the teachings detailed herein.

The electrode contacts 148 depicted in FIGS. 2A-2C are so-called flat contacts. In this regard, the surface of the electrode contact that faces the wall of the cochlea/the faces away from the longitudinal axis of the electrode array 146 is flat. Conversely, as seen in FIGS. 2D-2H, in some alternate embodiments, the electrode contacts 148 are so-called half band electrodes. In some exemplary embodiments, a band of contact material is "smashed" or otherwise compressed into a "half band," as seen in the figures. It is noted that by "half band," this does not mean that the electrode contact must necessarily span half of the outside diameter of the electrode array, as is the case in FIGS. 2G and 2H. The term is directed towards the configuration of the electrode itself as that term has meaning in the art. Any electrode contact that can have utilitarian value according to the teachings detailed herein can be utilized in at least some exemplary embodiments.

As can be seen from FIGS. 2A-2H, the positioning of the electrode contacts relative to the carrier 149 can vary with respect to alignment of the outer surface of the carrier with the outer surface of the contact. For example, FIGS. 2A, 2E, and 2F depict the outer surface of the contacts 148 as being flush with the outer surface of the carrier 149. Conversely, FIGS. 2C and 2G depict the contact 148 as being recessed with respect to the outer surface of the carrier 149, while FIG. 2H depicts the contact 148 as being proud relative to the outer surface of the contact 149. It is noted that these various features are not limited to the specific contact geometry and/or the specific carrier geometry depicted in the figures, and that one or more features of one exemplary embodiment can be combined with one or more features of another exemplary embodiment. For example, while FIG. 2H depicts a half band contact as being proud of the carrier

149 having a generally circular cross-section, a flat electrode such as that depicted in FIG. 2A can be proud of the carrier as well.

Figure 3B:
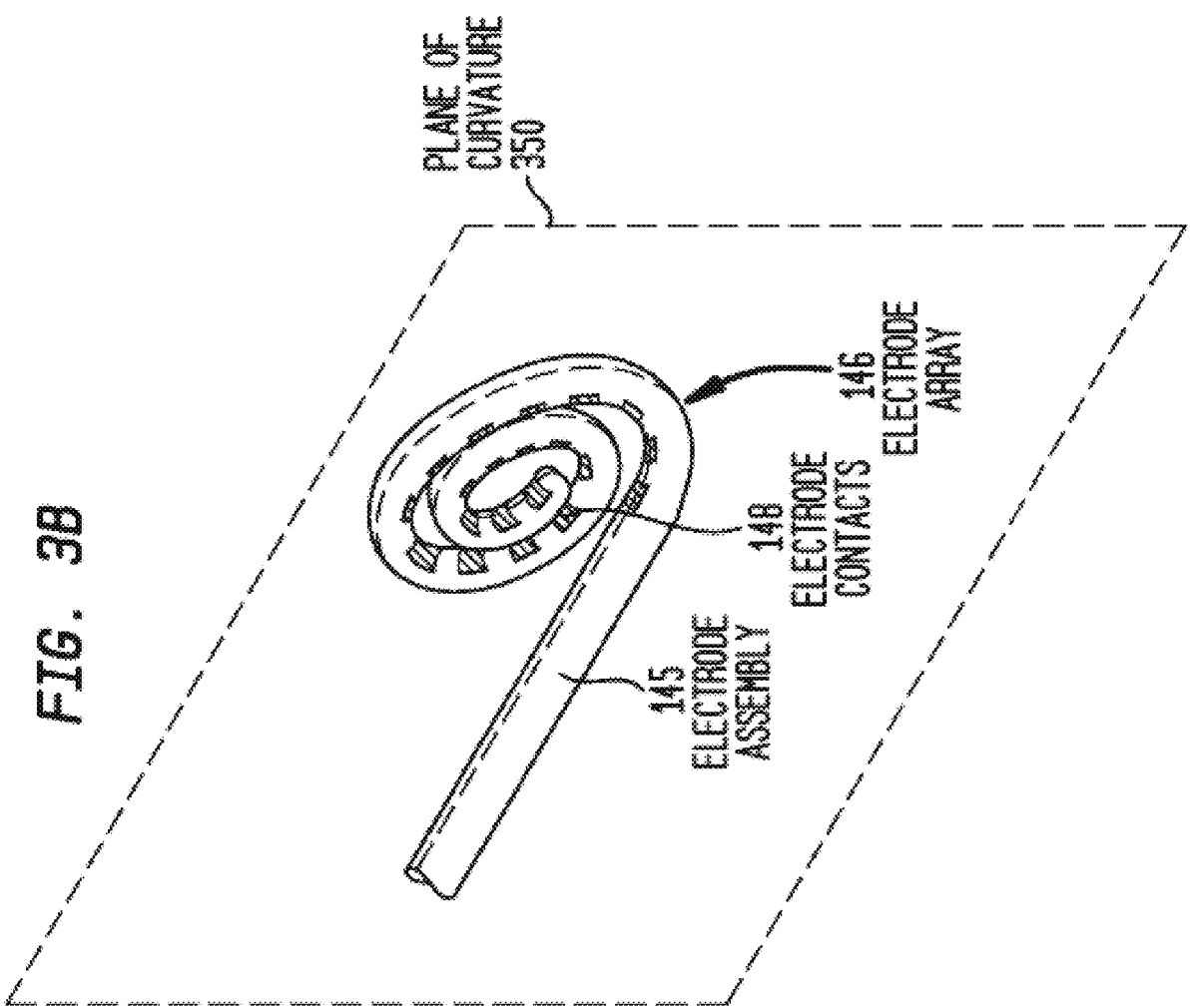

FIGS. 3A and 3B are side and perspective views, respectively, of representative electrode assembly 145. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve, so that it is able to conform to the curved interior of cochlea 140. As shown in FIG. 3B, when not in cochlea 140, electrode assembly 145 generally resides in a plane 350 as it returns to its curved configuration. That said, it is noted that the teachings detailed herein and/or variations thereof can be applicable to a so-called straight electrode array, which electrode array does not curl after being free of a stylet or insertion guide tube etc., but instead remains straight. It is noted that when in the cochlea, the electrode assembly 145 takes on a conical shape with respect to plane 350 in that it can be described as winding upward away from the plane 350 about an axis normal thereto, owing to the shape of the cochlea (more on this below).

The perimodiolar electrode assembly 145 of FIGS. 3A and 3B is pre-curved in a direction that results in electrode contacts 148 being located on the interior of the curved assembly, as this causes the electrode contacts to face the modiolus when the electrode assembly is implanted in or adjacent to cochlea 140.

It is also noted that while the embodiments of FIGS. 2A-3B have been presented in terms of a so-called non-tapered electrode array (where the cross-sections of the array on a plane normal to the longitudinal axis at various locations along the longitudinal axis (e.g., in between each electrode (or a majority of the electrodes), in the middle of each electrode (or a majority of the electrodes) etc.) have generally the same cross-sectional area and shape), in an alternate embodiment, the teachings detailed herein can be applicable to a so-called tapered electrode, where the cross-sectional areas on planes taken normal to the longitudinal axis decrease with location towards the distal end of the electrode array.

FIGS. 4A-4E depict an exemplary insertion regime of an electrode assembly according to an exemplary embodiment. As shown in FIG. 4A, the combined arrangement of an insertion guide tube 300 and electrode assembly 145 is substantially straight. This is due in part to the rigidity of insertion guide tube 300 relative to the bias force applied to the interior wall of the guide tube by pre-curved electrode assembly 145.

As noted, in some embodiments, the electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly from returning to its pre-curved configuration. In the embodiment configured to be implanted in scala tympani of the cochlea, electrode assembly 145 is pre-curved to have a radius of curvature that approximates and/or is less than the curvature of medial side of the scala tympani of the cochlea. Such embodiments of the electrode assembly are referred to as a perimodiolar electrode assembly, and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

Drug delivery to the inner ear is sometimes achieved by oral or intravenous application of the drug which has shown to be inefficient due to concentrations in the inner ear below the therapeutic range of the drug. To overcome this issue, a local administration approach using drug loaded gels which are applied onto the round window and relies on drug diffusion through the round window membrane are currently explored. Another approach currently explored are drug eluting cochlear implant electrodes. These approaches result in a concentration gradient of the drug with high concentrations at the base and low concentrations further toward the apex. Another problem is the little control over dosing. Drug pumps are also currently explored to deliver the dissolved drug directly into the cochlea by inserting a cannula through the round window membrane. The standard cannulas have a single exit point at its end which results in drug delivery to a discrete location inside the inner ear and therefore a concentration gradient along the scala. Another issue is that CI electrodes and cannulas have to be rigid or stiff enough to be able to insert them into the cochlear (i.e. scala tympani through the round window or cochleostomy). Inserting those relatively stiff electrodes and/or cannulas can cause damage to inner ear structures know as insertion trauma—Insertion trauma often results in loss of hearing. At least some embodiments of some of the teachings herein do not have one or more or all of the just detailed features.

In some instances, complex pharmacokinetics of the inner ear hinders the distribution of drugs administered to the basal region of the cochlear along the scala tympani into the apical region. Any drug delivery mechanism where drug is administered at discrete locations outside or inside the cochlea as described above faces this issue if an even distribution throughout the scala is desired. Another issue with respect to delivery at discrete locations in the inner ear might be a too fast metabolic rate of the drug which does not allow bioactive drug to reach regions which are far away from the discrete delivery points. Drug-loaded hydrogels or polymers attached to an electrode like the dexamethasone loaded electrode array can achieve drug release over a certain length of the cochlear but the elution rate is limited by passive diffusion and treatment duration by the total amount of drug the device can hold. At least some embodiments of some of the teachings herein do not have one or more or all of the just detailed features.

At least some embodiments disclosed herein overcomes at least one or more or all of the above noted issues. Some embodiments enable even drug concentration from base to apex and/or a larger area towards the apex. Some embodiments render minimal risk of damage to inner ear structures and associated loss of residual hearing. Some embodiments also provide controlled and sustained drug administration rates.

Figure 5:
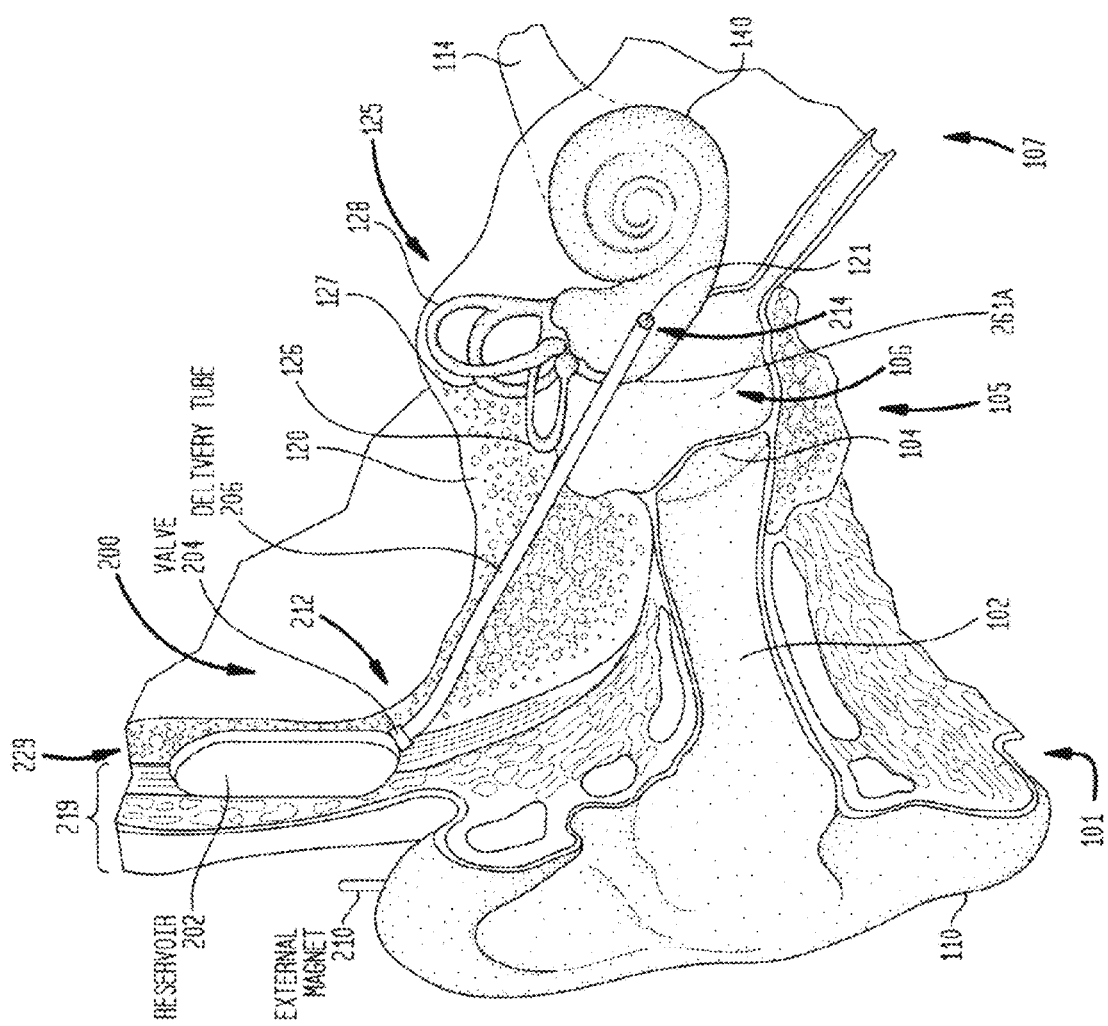
FIGS. 5-7 present an exemplary therapeutic substance delivery system.

FIG. 5 depicts an exemplary drug delivery device, the details of which will be provided below. It can be utilitarian to have a prompt and/or extended delivery solution for use in the delivery of treatment substances to a target location of a recipient. In general, extended treatment substance delivery refers to the delivery of treatment substances over a period of time (e.g., continuously, periodically, etc.). The extended delivery may be activated during or after surgery and can be extended as long as is needed. The period of time may not immediately follow the initial implantation of the auditory prosthesis. Embodiments of the teachings herein can facilitate extended delivery of treatment substances, as well as facilitating prompt delivery of such substances.

FIG. 5 illustrates an implantable delivery system 200 that can be utilized with the teachings detailed herein, and otherwise modified as detailed by way of example below. The delivery system has a passive actuation mechanism. However, it is noted that the delivery system 200 can also or instead have an active actuation system.

Exemplary embodiment, the delivery system 200 can utilize an implanted battery-powered pump and/or an implanted pump that is magnetically linked temporarily to a motor located outside the recipient where the magnetic field that extends from the motor to the implanted pump is utilized to turn The implanted pump (magnets having poles can be "spun," where the implanted magnet will attract and repel from the external magnet, and thus move/turn the implanted pump.

Figure 6:
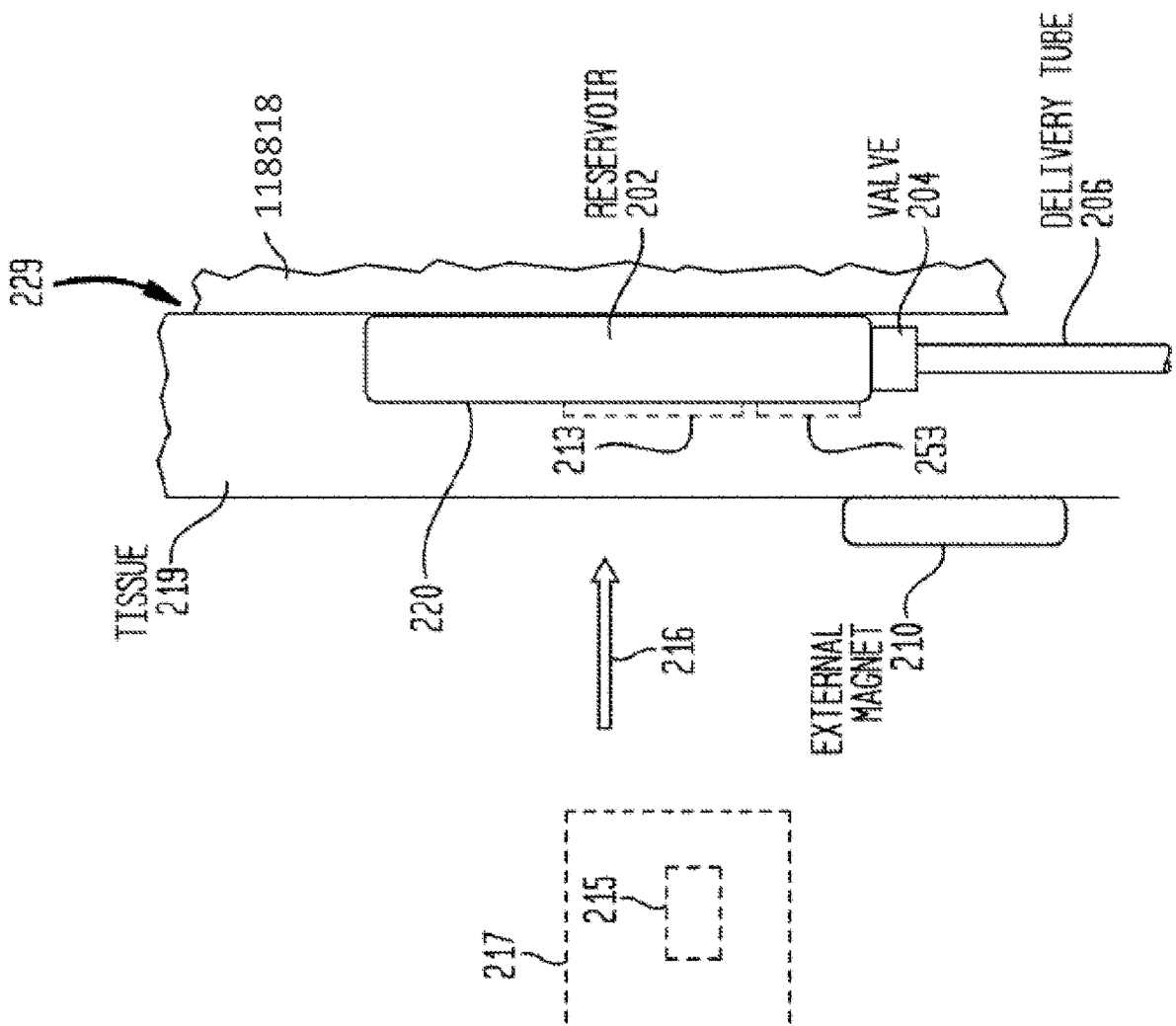

The delivery system 200 is sometimes referred to herein as an inner ear delivery system because it is configured to deliver treatment substances to the recipient's inner ear (e.g., the target location is the interior of the recipient's cochlea 140). FIG. 6 illustrates a first portion of the delivery system 200, while FIG. 7 is a cross-sectional view of a second portion of the delivery system 200.

Figure 7:
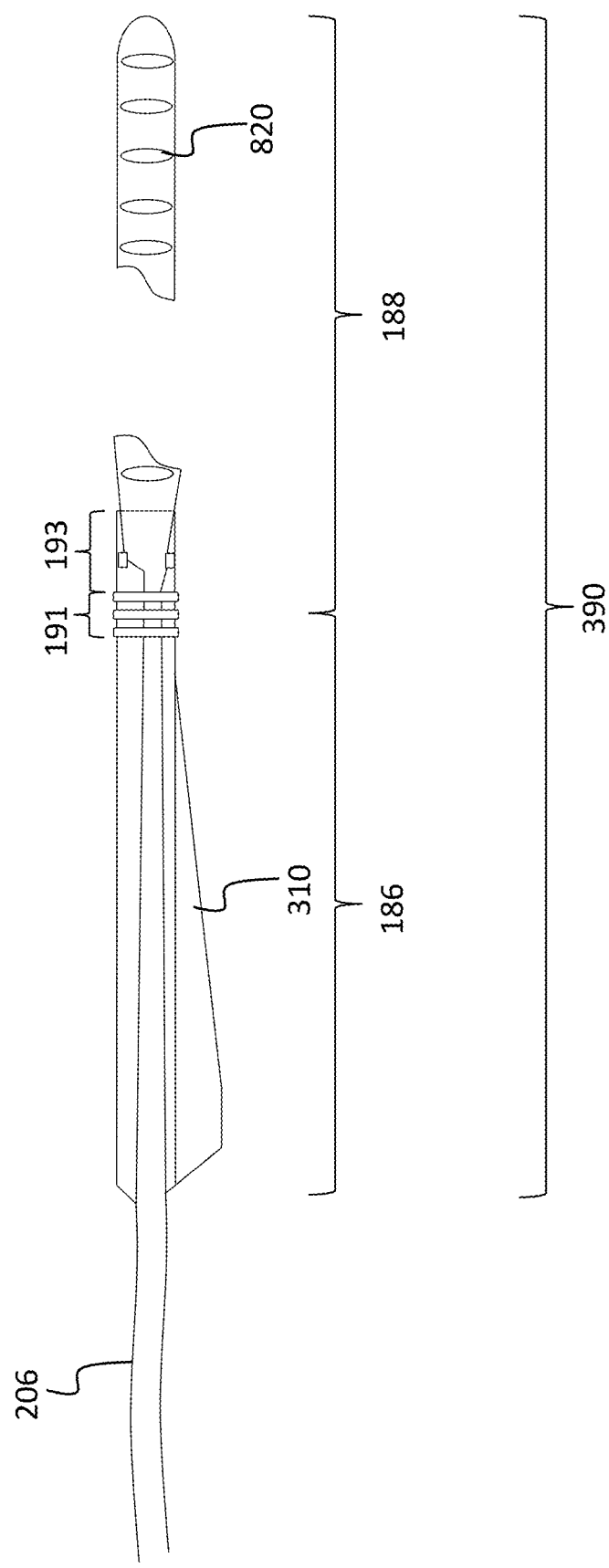

Delivery system 200 of FIGS. 5-7 comprises a reservoir 202, a valve 204, a delivery tube 206, and a delivery device 390. For ease of illustration, the delivery system 200 is shown separate from any implantable auditory prostheses. However, it is to be appreciated that the delivery system 200, the delivery system 200 as modified below, and other delivery systems as detailed herein and variations thereof, and any of the other delivery systems detailed herein and/or variations thereof, could be used with, for example, cochlear implants, such as that presented in FIG. 1, direct acoustic stimulators, middle ear implants, bone conduction devices, etc. Also, the delivery system(s) herein can be used as standalone devices. The delivery systems herein can be used as temporary devices or permanent devices, and this is further detailed below. The implantable components (e.g., reservoir, valve, delivery tube, etc.) of delivery system 200 (or any other delivery system and/or portions thereof detailed herein) could be separate from or integrated with the other components of the implantable auditory prosthesis. Additionally, the delivery system 200 can include, or operate with, an external magnet 210, which is separate from or part of the implantable auditory prostheses, for purposes of, e.g., controlling operation of valve 204.

The reservoir 202 is positioned, in some embodiments, within the recipient underneath a portion of the recipient's skin/muscle/fat, collectively referred to herein as tissue 219. The reservoir 202 may be positioned between layers of the recipient's tissue 219 or may be adjacent to a subcutaneous outer surface 229 of the recipient's skull. For example, the reservoir 202 may be positioned in a surgically created pocket at the outer surface 229 (i.e., adjacent to a superior portion 118818 of the temporal bone 115).

The reservoir 202 or a variation thereof and the components that extend therefrom to the delivery device (sometimes herein referred to in the generic sense of the working end, which would include the extendable delivery device detailed below in embodiments where that is connected to the delivery tube—more on this below) can be an external device as well (which could be the same as the implant reservoir 202, or a less robust (in the sense that it need not be an implantable device) external reservoir that could be utilized for surgical and/or outpatient procedures at a medical facility, or could be an extra reservoir that could be carried by the recipient during normal activities and/or could be a reservoir that would be located in the recipient's home or at a location where the recipient is stationary (which could be an automobile, etc.). Any arrangement that will enable the reservoir and the associated components to reach the extendable delivery device and provide therapeutics options there to utilize at least some embodiments. Additional details of some of the embodiments will be described below.

The reservoir 202 is, prior to or after implantation, at least partially filled with a treatment substance/therapeutic substance for delivery to the inner ear 107 of the recipient. The treatment substance may be, for example, in a liquid form, a gel form, and/or comprise nanoparticles or pellets. In certain arrangements, the treatment substance may initially be in a crystalline/solid form that is subsequently dissolved. For example, a reservoir could include two chambers, one that comprises a fluid (e.g., artificial perilymph or saline) and one that comprises the crystalline/solid treatment substance. The fluid may be mixed with the crystalline/solid treatment substance to form a fluid or gel treatment substance that may be subsequently delivered to the recipient.

The reservoir 202 includes a needle port (not shown) so that the reservoir 202 can be refilled via a needle injection through the skin. The reservoir 202 may be explanted and replaced with another reservoir that is, prior to or after implantation, at least partially filled with a treatment substance. The reservoir 202 may have a preformed shape and the reservoir is implanted in this shape. The reservoir 202 may have a first shape that facilitates implantation and a second shape for use in delivering treatment substances to the recipient. For example, the reservoir 202 may have a rolled or substantially flat initial shape that facilitates implantation. The reservoir 202 may then be configured to expand after implantation. Such may be used, for example, to insert the reservoir through a tympanostomy into the middle ear or ear canal, through an opening in the inner ear, or to facilitate other minimally invasive insertions. Reservoir 202 may have other shapes as needed to operate with hearing prostheses, as will be detailed below by way of example and not by way of limitation.

As shown in FIG. 5, the delivery tube 206 includes a proximal end 212 and a distal end 214. The proximal end 212 of the delivery tube 206 is fluidically coupled to the reservoir 202 via the valve 204. As shown in FIG. 7, the distal end 214 of the delivery tube 206 is fluidically coupled to a delivery device 390, which can be positioned through the round window 121 or another entrance into the cochlea, as will be describe below. As described further below, the delivery tube 206 may be secured within the recipient so that the distal end 214/deliver device 390 remains located in the cochlea. In other embodiments, the delivery device 390 is only temporarily in the cochlea (more on this below). It is briefly noted that while the embodiments are directed herein to a delivery device that is located in, at least in part, and/or provides therapeutic substance of the cochlea, embodiments include devices that are configured to be located in, at least in part, and/or provide therapeutic substance to other portions of the body, such as by way of example only and not by way of limitation, the semi-circular canals of the vestibular system, and/or fragile blood vessels of the brain, etc. In an exemplary embodiment, the teachings detailed herein can provide access to portions of the body that would be too traumatic for access by, for example, would normally needle or lumen or the like. Accordingly, any disclosure herein of a device that is configured to enter into the cochlea and/or provide therapeutic substance into the cochlea corresponds to a disclosure of an alternate embodiment of a device that is configured to enter into any other body portion and/or deliver therapeutic substance to any other body portion that is enabled by the art utilizing the teachings detailed herein, such as veins, arteries, the heart, portions of the brain, portions of the eyes, portions of the nervous system, in between vertebrae sections, etc.

FIGS. 5-7 illustrate a system that utilizes a passive actuation mechanism to produce a pumping action to transfer a treatment substance from the reservoir 202 to the delivery device 390 at the distal end 214 of the delivery tube 206. More specifically, in this system, the reservoir 202 is compressible in response to an external force 216. That is, at least one part or portion of the reservoir 202, such as wall 220 or a portion thereof, is formed from a resiliently flexible material that is configured to deform in response to application of the external force 216. In some implementations of the system of FIG. 5, positioning of the reservoir 202 adjacent the superior portion of the mastoid provides a surface that is sufficiently rigid to counter the external force 216. As a result, a pressure change occurs in the reservoir 202 so as to propel (push) a portion of the treatment substance out of the reservoir through valve 204.

It is briefly noted that the insertion regime of the electrode array detailed above can be followed, in some embodiments, for inserting the delivery devices herein.

FIGS. 5 and 6 illustrate a specific arrangement in which the reservoir 202 includes a resiliently flexible wall 220. It is to be appreciated that the reservoir 202 can be formed from various resiliently flexible parts and rigid parts. It is also to be appreciated that the reservoir 202 may have a variety of shapes and sizes (e.g., cylindrical, square, rectangular, etc.) or other configurations. For example, the reservoir 202 could further include a spring mounted base that maintains a pressure in the reservoir 202 until the reservoir is substantially empty. Other mechanisms for maintaining a pressure in the reservoir may be used in other arrangements. By way of example only and not by way of limitation, the delivery tube could be pinched or otherwise compressed at certain locations to move the fluid therein along the tube. In an exemplary embodiment, pumping action can be achieved by, for example, peristaltic action of pinching a flexible tube utilizing rotating rollers or the like. Any device system or method that will enable the movements of fluid can be utilized in at least some exemplary embodiments.

External force is applied on the tissue 219 adjacent to the reservoir 202 to create the external force. As will be described below, in some embodiments, an external vibratory device of a passive transcutaneous bone conduction device that vibrates to evoke a hearing percept is pressed onto the soft tissue 219 under which the reservoir 202 is located. The movement (e.g., oscillation/vibration) of the actuator causes deformations the reservoir 202 to create the pumping action that propels the treatment substance out of the reservoir.

Internal and/or external magnets and/or magnetic materials may be used in the arrangements of FIGS. 5 and 6 to ensure that the actuator 217 applies force at an optimal location of the reservoir 202. For example, the reservoir 202 may include a magnetic positioning member 213 located at or near an optimal location for application of an external force from the actuator 217. The actuator 217 may include a magnet 215 configured to magnetically mate with the magnetic positioning member 213. As such, when actuator 217 is properly positioned, the magnet 215 will mate with the magnetic positioning member 213 and the force from the actuator 217 will be applied at the optimal location.

A remote control, remotely placed actuator (subcutaneous or otherwise) may be alternatively used. For example, in a further arrangement, the implant includes implanted electronics 253 (shown using dotted lines in FIG. 6). These implanted electronics 253 may be configured to, for example, control the valve 204 and/or include an actuation mechanism that can force treatment substance from the reservoir 202. The implanted electronics 253 may be powered and/or controlled through a transcutaneous link (e.g., RF link). As such, the implanted electronics 253 may include or be electrically connected to an RF coil, receiver/transceiver unit, etc.

The implanted electronics 253 may include or be connected to a sensor that is used, at least in part, to assist in control of delivery of the treatment substance to the recipient. For example, a sensor (e.g., a temperature sensor, a sensor to detect infection or bacteria growth, etc.) may provide indications of when a treatment substance should be delivered and/or when delivery should be ceased for a period of time. A sensor may also be configured to determine an impact of the treatment substance on the recipient (e.g., evaluate effectiveness of the treatment substance).

As noted, the treatment substance (sometimes herein referred to as therapeutic substance) is released from the reservoir 202 through the valve 204. The valve 204 may be a check valve (one-way valve) that allows the treatment substance to pass therethrough in one direction only. This assures that released treatment substances do not back-flow into the reservoir 202. The valve 204 is a valve that is configured to open in response to the pressure change in the reservoir 202 (e.g., a ball check valve, diaphragm check valve, swing check valve or tilting disc check valve, etc.). The valve 204 may be a stop-check valve that includes an override control to stop flow regardless of flow direction or pressure. That is, in addition to closing in response to backflow or insufficient forward pressure (as in a normal check valve), a stop-check value can also be deliberately opened or shut by an external mechanism, thereby preventing any flow regardless of forward pressure. The valve 204 may be a stop-check value that is controlled by an external electric or magnetic field generated by, for example, the external magnet 210, an electromagnet, etc. In the system of FIGS. 5 and 6, the valve is responsive to a magnetic field generated by external magnet 210. As such, the valve 204 will open when the external magnet 210 is positioned in proximity to the valve 204 and will close when the external magnet 210 is removed from the proximity of the valve 204. Variable magnet strengths of external magnets may be used to control the dosage of the treatment substance. Additionally, an electromagnet may be used in place of the external magnet 210.

The use of a stop-check valve can prevent unintended dosing of the treatment substance when, for example, an accidental external force acts on the reservoir 202. The reservoir 202 is formed such that an increase in pressure of the reservoir 202 without an accompanying treatment substance release will not damage (i.e., rupture) the reservoir.

The use of a magnetically activated stop-check valve is merely exemplary and that other types of valves may be used. For example, the valve 204 may be actuated (i.e., opened) in response to an electrical signal (e.g., piezoelectric valve). The electrical signal may be received from a portion of an auditory prosthesis (not shown) that is implanted with the delivery system 200 or the electrical signal may be received from an external device (e.g., an RF actuation signal received from an external sound processor, remote control, etc.). In some instances, manually applied (e.g., finger) force be also able to open the valve 204.

Once the treatment substance/therapeutic substance is released through valve 204, the treatment substance flows through the delivery tube 206 to the delivery device 390. The delivery device 390 operates as a transfer mechanism to transfer the treatment substance from the delivery tube 206 to the cochlea.

The reservoir 202 may include a notification mechanism that transmits a signal or notification indicating that the reservoir 202 is substantially empty and/or can benefit from refilling. For example, one or more electrode contacts (not shown) may be present and become electrically connected when the reservoir is substantially empty. Electronic components associated with or connected to the reservoir 202 may accordingly transmit a signal indicating that reservoir needs filled or replaced. In an exemplary embodiment, methods include detecting a change in an electrical impedance of a section of the reservoirs flexible wall, which can be a latent variable indicative of an amount of substance in the reservoir or tube, etc., and can be indicative of an empty or near empty reservoir. In an exemplary embodiment, the electrical impedance decreases when the pressure drops and the stretched material relaxes. Embodiments include devices systems and methods of detecting this phenomenon and or utilizing this phenomenon to determine at least approximately an amount of substance a reservoir and/or in the tube and/or determine whether at least approximately the amount of fluid has been exhausted or is approaching exhaustion.

Figure 8:
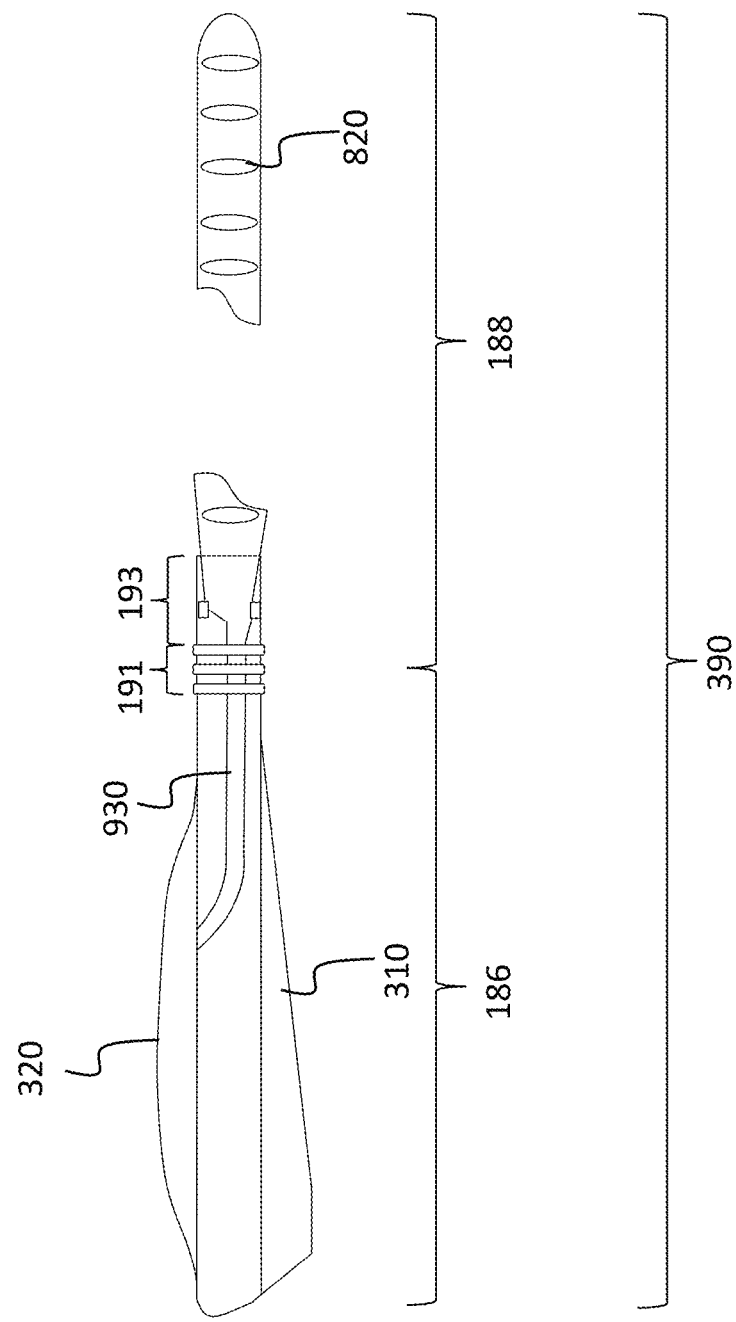
FIG. 8 presents an alternate embodiment of a delivery system.

FIG. 7 represents an exemplary delivery device 390 that is in fluid communication with tube 206. FIG. 8 depicts an exemplary delivery device that is used independently of the teachings of FIGS. 5-6. It is note that some embodiments can be utilized in combination with some or all of the features of electrode array assembly 190 of FIG. 1B, while in other embodiments, the therapeutic substance delivery system is a standalone device.

The delivery device 390 includes element 310, which is a quasi-handle like device utilized with utilitarian value vis-à-vis inserting the 188 section into a cochlea. By way of example only and not by way of limitation, element 310, which is a silicone body that extends laterally away from the longitudinal axis of the device 390, and has a thickness that is less than that of the main body of the assembly. The thickness combined with the material structure is sufficient so that the handle can be gripped at least by a tweezers or the like during implantation and by application of a force on to the tweezers, the force can be transferred into the device 390 so that section 188 can be inserted into the cochlea.

In an exemplary embodiment, delivery tube 206 extends from the reservoir to the delivery device 390. The delivery tube can provide therapeutic substances from the reservoir.

Further, it is noted that in an alternate embodiment, a reverse fluid direction regime can be implemented where perilymph and/or other bodily fluids are pulled into the tube 206 so that sampling of the body fluid can be executed. In an exemplary embodiment, there can be a time lag between the development of a negative pressure within the tube 206 and the closure or shrinkage of the passageways into the tube. Moreover, putting on the material that is utilized to make the tube, the tube can be a "slow resist" material that will be slow to collapse upon the presence of a negative pressure inside the tube. Indeed, in an exemplary embodiment, the tube can be configured so that upon deployment, the tube basically will not collapse under limited negative pressure regimes. That is, upon deployment, the tube will basically remain deployed/"inflated" until a significant negative pressure inside the tube exists if even that. Accordingly, by utilizing a tube that will remain expanded even in a scenario where the inside of the pressure is less than the outside pressure, the tubes can be utilized to draw in body fluids. This can have utilitarian value with respect to enabling the implant to sample or otherwise analyze the body fluids, such as, for example, to determine a concentration of a therapeutic substance in a body fluid and/or to determine the presence of indicators that would indicate a problem and/or a good occurrence, and thus embodiments include devices systems and/or methods of utilizing such to determine whether or not certain action should be taken, such as increasing and/or decreasing the amount of therapeutic substance delivered (volume, mass, either amount or flow rates, etc.).

The embodiment of FIG. 8 differs from FIG. 7 in that there is reservoir 320. In an exemplary embodiment, this is an optional feature. In some embodiments, delivery tube 206 could feed reservoir 320 (not shown). In an exemplary embodiment, there is only reservoir 320 (FIG. 8) while in other embodiments, there is only the reservoir of FIG. 5 (FIG. 7). As will be detailed below, in some embodiments, the reservoir 320 can be refilled via delivery tube 206, such as from the reservoir of FIG. 5 or from another component, while in other embodiments, the reservoir 320 can be refilled as will be disclosed below, such as through the tympanic membrane. Thus, in an exemplary embodiment, there is no delivery tube 206 extending to the delivery device 390, while in other embodiments, there is no reservoir 320. In an exemplary embodiment, reservoir 320 as with the reservoir of FIG. 5, is configured to contain a bioactive substance or otherwise some form of mass that has fluid properties. In an exemplary embodiment, the reservoir 320 and/or delivery tube 206 is in fluid communication with one or more portions of the device making up section 188, as will be described in greater detail below. Some additional features of "the plumbing" will be described below. First however, some exemplary features of the reservoir 320 will now be described.

In an exemplary embodiment, the reservoir is an expandable reservoir. By way of example only and not by way of limitation, in an exemplary embodiment, the reservoir is made out of an elastomeric material and forms an elastomeric enclosure. In an exemplary embodiment, in a relaxed state, the reservoir 320 establishes a first interior volume and takes up a first exterior volume. When in an expanded state, the reservoir 320 establishes a second interior volume that is larger than the first interior volume, and also takes up a second exterior volume that is larger than the first exterior volume. In an exemplary embodiment, the reservoir has any one or more or all of the features of the reservoir of U.S. Patent Application No. 62/722,273, entitled "Mass Transport Inside Mammals," to Daniel Smyth, filed on Aug. 24, 2018, and communicates with the 188 section as disclosed in that application. In an exemplary embodiment, a volume changing material is placed next to the flexible reservoir to pressurized the reservoir. In an exemplary scenario both the reservoir and the volume changing material are fixed in a relative location to each other, such as, for example, inside a titanium housing, or to a titanium platform, etc.

Figure 9:
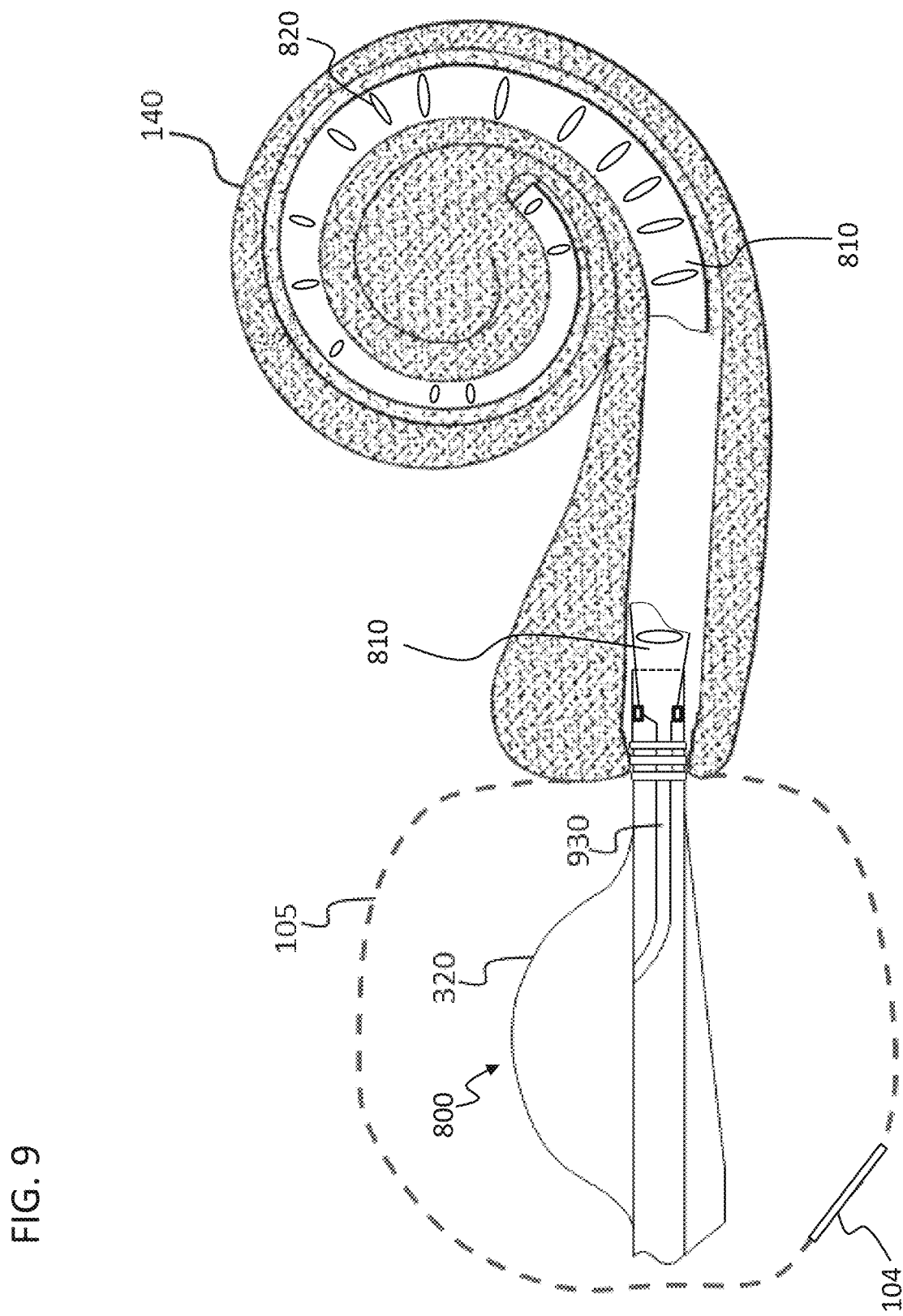
FIGS. 9-10 depict exemplary insertion regimes of the delivery devices into the cochlea.
Figure 10:
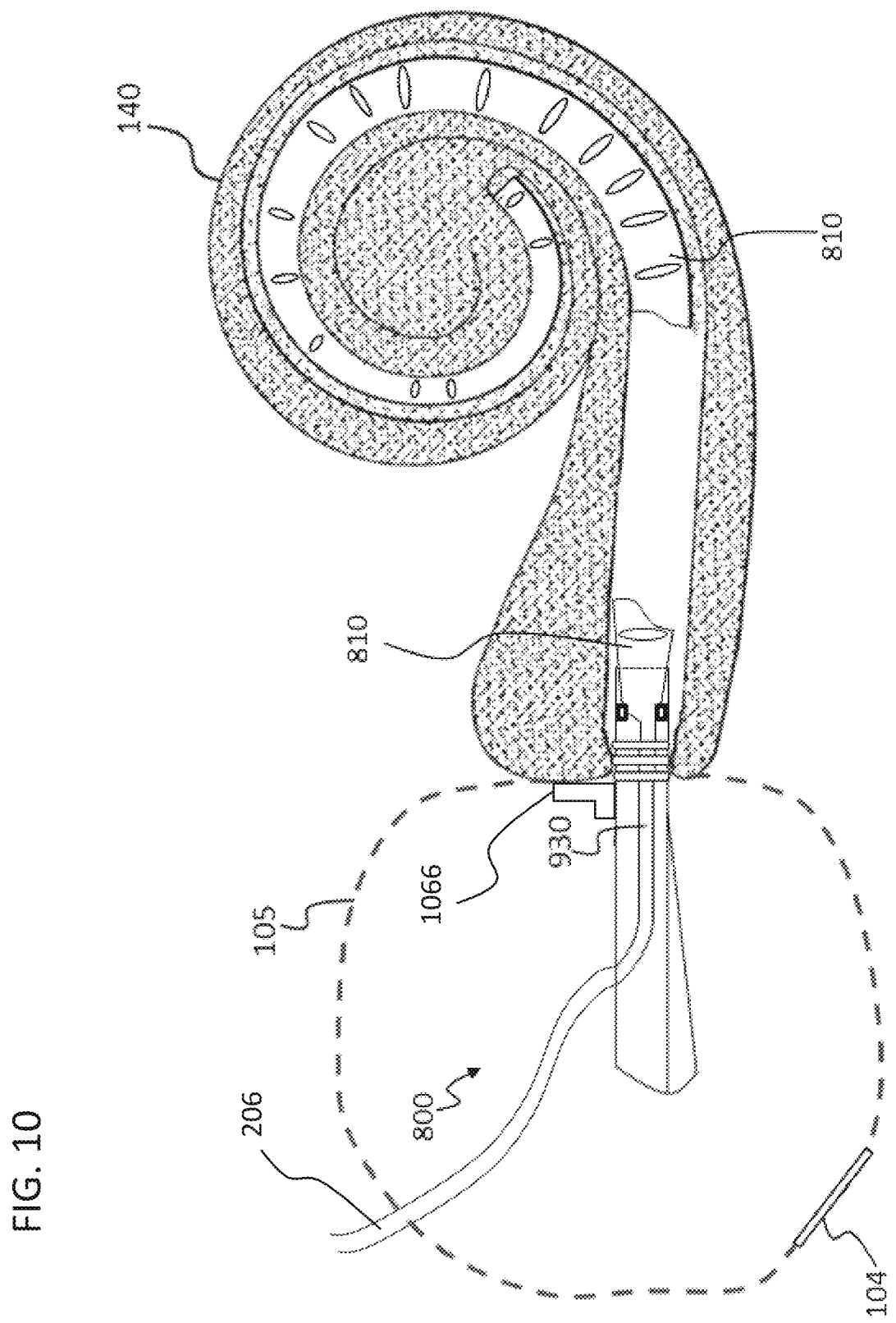

FIG. 9 presents a conceptual representation of the delivery system 390 (that of FIG. 8, but this is representative of the embodiment of FIG. 7 as well—that said, FIG. 10 presents a variation of the embodiment of FIG. 7) inserted into a cochlea 140 that is configured to prosthetically remain in the cochlea (that is, it is configured to remain in the cochlea for a time period concomitant with the use of a prosthetic device, as opposed to a temporary insertion such as might be the case for a needle or the like). FIG. 9 depicts a conceptual drawing depicting the intra-cochlea region [[188]] of the delivery system 390 in the cochlea 140, and the proximal region 186 of the delivery system located outside the cochlea 140. Conduit 930 (more on this below) of the delivery system extends from inside the cochlea 140 to outside the cochlea into the middle ear cavity, which is functionally represented by the dashed enclosure 105, and to the reservoir 320.

It is noted that the schematic of FIG. 9 is provided at least for the purpose of presenting a delivery system 390 according to an exemplary embodiment. In an exemplary embodiment, the delivery system 390 along with a portion of the conduit 930 is inserted into the scala tympani. Accordingly, in an exemplary embodiment, there is a delivery system 390 configured such that the delivery system 390 is insertable into the scala tympani, and the reservoir is located in the middle ear cavity outside the scala vestibule but in fluid communication at least indirectly therewith.

As noted above, in an alternative embodiment, the reservoir 320 could instead be replaced with the reservoir of FIG. 5. Delivery tube 206 could extend to conduit 930 and thus place the reservoir of FIG. 5 into fluid communication therewith. This is shown by way of example in FIG. 10, which depicts an alternate embodiment of the delivery device 390 (the same principle of FIG. 7 for all intents and purposes).

Delivery device 390 includes a cochlea wall interface (represented by section 191 in the FIGs.) that interfaces with the hole extending into the cochlea. The cochlea wall interface is part of a "stationary" component of the delivery system. It is stationary in the sense that when the delivery system is located in the cochlea, it is not a component that is deployed, as compared to component 810 (which is a delivery apparatus, as will be described below), which is the deployable component which is deployed from the stationary component. Component 810 is shown in an incomplete manner, where the portion thereof that extends from the location proximate the stationary component to the location proximate about the first turn is not shown. Component 810 includes outlets 820, which permit therapeutic substance delivered to the delivery system to exit delivery system and into the cochlea. Some additional details of this will now be described.

Note also that while the embodiments depicted above have focused on the utilization of a single reservoir, in an alternate embodiment, two or more reservoirs can be utilized. The reservoirs can be manifold to one another so that the reservoirs expand and/or contract at a similar (which includes the same) rate as each other or can be fluidically separated from each other so that expansion and/or contraction of one as a result of mass flow in and/or out of that one reservoir does not affect the pressure in the other reservoirs. Consistent with FIG. 5, it is noted that in some embodiments, the reservoir or one or all of the reservoirs or a portion of one or more can be located at other locations other than the middle ear. In some embodiments, all or part of the reservoir is located in a surgical cavity created during surgery. It is briefly noted that the reservoir can be located anywhere that can enable the teachings detailed herein and/or other embodiments where therapeutic substance is delivered to other body parts.

It is briefly noted that frequently, the phrase "drug" will be utilized herein. Embodiments are directed towards a drug delivery system. However, embodiments are not so limited unless otherwise specified. In this regard, embodiments are directed towards a therapeutic substance delivery system. Therapeutic substances include drugs, but also include non-drug substances. In an exemplary embodiment, therapeutic substances include steroids and biologics. Therapeutic substances can also include minerals and the like. Any disclosure herein of drug or the containment of drug or the delivery of drug also corresponds to another embodiment that corresponds to an embodiment that is directed towards a therapeutic substance. That is, typically, the word drug used herein is shorthand for therapeutic substance. Accordingly, embodiments include the present disclosure where the word drug is replaced by the word therapeutic substance, unless otherwise specified.

Further, it is noted that while some embodiments of the teachings detailed herein are utilized to treat the effects associated with implanting a component in the ear system of the recipient, such as by way of example only and not by way of limitation, providing anti-inflammatory substances and/or steroids to the cochlea following a cochlear implant electrode array insertion, other embodiments of the teachings detailed herein are not utilized per se with an implant. In this regard, the teachings detailed herein can be utilized to treat hearing problems irrespective of whether or not the recipient is utilizing the prosthesis. By way of example only and not by way of limitation, in an exemplary embodiment, the teachings detailed herein can be utilized to treat a syndrome that is attacking the hair cells of the cochlea prior to the utilization of a hearing prosthesis—even in some instances—by the recipient. That said, the teachings detailed herein can be utilized in isolation from any other prostheses. It is also noted that the teachings detailed herein can be used in combination with conventional hearing aids. In this regard, the teachings detailed herein can be utilized to treat ailments associated with the hearing and/or balance system of a recipient that may or may not rise to the level of requiring an implantable and/or partially implantable hearing prosthesis.

Some embodiments of the delivery system detailed herein can include a refillable drug reservoir (with or without a pump) that can be placed in a suitable space outside the cochlea (e.g., middle ear), or above the mastoid bone, or, in some embodiments, outside the recipient (more on this below). The drug reservoir is connected, in some embodiments, to a catheter (which could be represented by tube 206 or conduit 320) which contains a deployable drug delivery apparatus, which can be in the form of a tube, with, in some embodiments but not others, a closed ending which is built in some sections but not others or completely from a drug permeable membrane. The deployable drug delivery apparatus in combination with the catheter can have features at its end to enable opening the cochlea (cochleostomy) without drilling, enable piercing the round window membrane, enable fixation and sealing the opening (e.g. a flange with holes) and enable safe alignment tangential to the scala tympani. Still, in some embodiments, a hole might be drilled into the cochlea bony wall (cochleostomy), through which the delivery device is inserted.

Figure 11:
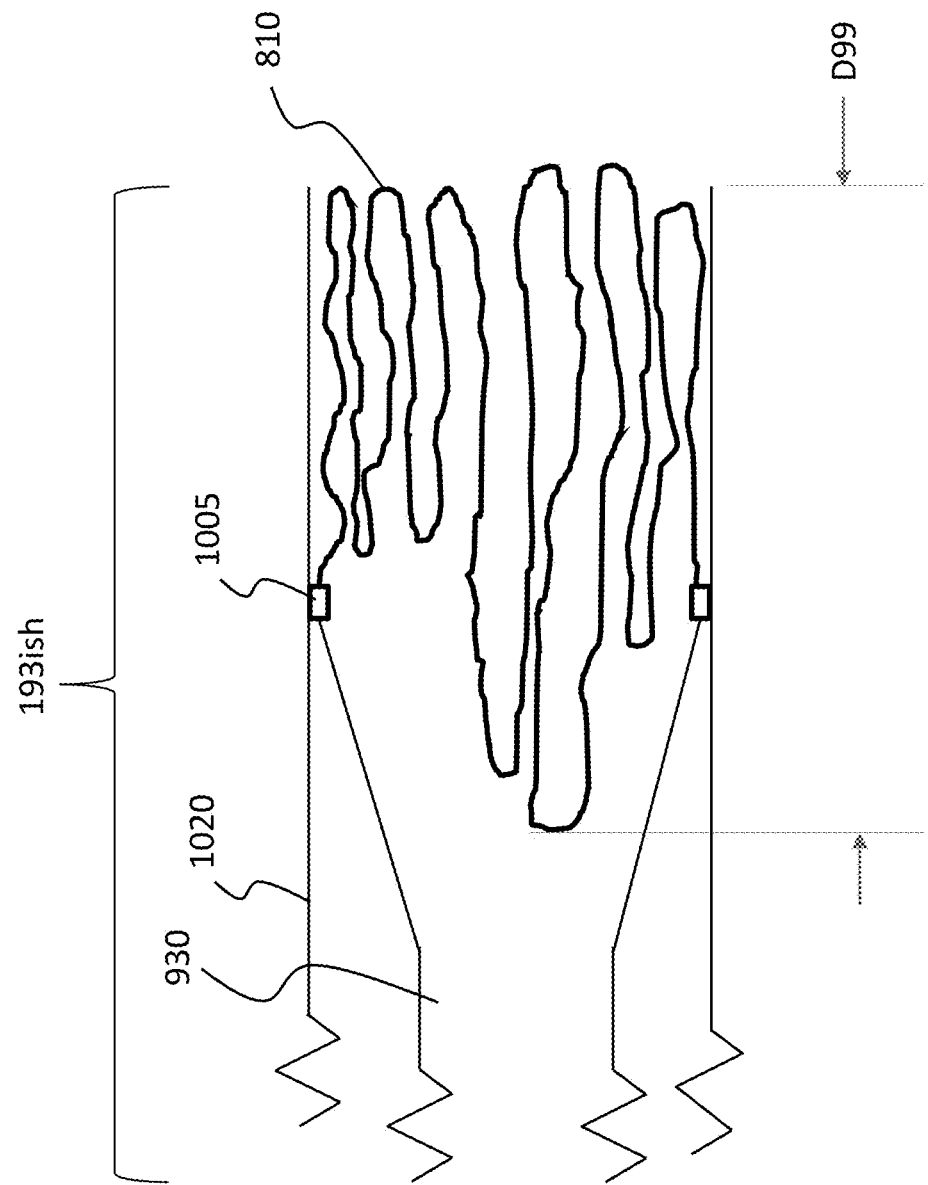
FIG. 11 depicts an exemplary pre-deployment state of an embodiment.

FIG. 11 presents a portion of the delivery device 390 that includes a section, section 193*ish*. This is the cochlea wall interface section plus the portion that extends into the cochlea a bit, hence the identifier "193*ish*," as opposed to "193." More on this below. Here, we are describing some things that we want to describe first, before we describe some things we want to describe later.

Section 193*ish* includes tubular body 1020, through which conduit 930 extends (which could instead be tube 206, in some embodiments—any disclosure of conduit 930 corresponds to the disclosure of tube 206, and vice versa, unless otherwise noted). Conduit 930 extends to seal ring 1005, and forms a fluid tight seal therewith. As can be seen, delivery apparatus 810 is also connected to seal ring 1005, and also forms a fluid tight seal therewith. In the embodiment shown in FIG. 11, the delivery apparatus 810 is in a pre-deployed/undeployed state.

In an exemplary embodiment, the delivery system is configured to increase the pressure and/or increase the mass flow rate (potentially from zero in some embodiments) and/or increase the amount of mass within the conduit 930 relative to that which is the case when the delivery apparatus 810 is in the pre-deployed/undeployed state. The increase of mass/pressure, etc., can, in some embodiments, exert a pressure/force within the delivery apparatus 810, which will eject the delivery apparatus 810 and/or expand the delivery apparatus 810 from the state that it is in in FIG. 11 to a state as seen in FIG. 12. That is, FIG. 12 presents the delivery apparatus 810 in a deployed state, albeit without the curve that would exist if deployed in the cochlea. As can be seen, outlets 820 are arrayed along the length of the delivery apparatus 810. These outlets can be orifices that enable the therapeutic substance that is delivered from the conduit 930 to exit the delivery apparatus 810 and enter the cochlea. In an exemplary embodiment, this is analogous to blowing up a long and thin balloon of the type that is used to make things such as dogs, bunnies, and other familiar shapes, by twisting the balloons and folding the balloon, etc. In some embodiments, the principle of operation that results in the balloon expanding is the same as that utilized herein. In an exemplary embodiment, a pump is utilized to increase the pressure/mass/mass flow rate so as to extend the delivery apparatus 810 from the tubular body 1020. The seal 1005 is significantly strong enough to hold the delivery apparatus 810, or, more accurately, the end of the delivery apparatus 810, in place, so that it does not shoot off/shoot out (beyond that which is desired, if such is shooting out) when the pressure and/or the mass and/or the mass flow rate is increased. In an exemplary embodiment, the delivery apparatus 810 and/or the total implantable component is configured to provide the surgeon or other healthcare professional visual and/or tactile and/or other types of feedback that tells the professional the penetration depth into the cochlea, or at least an indicator of an approximate penetration depth into the cochlea. Further, in an exemplary embodiment, the implant is configured to enable the deployment of the tube to be stopped within 1, 2, 3, 4, 5, 6, 7, 8, 9, 10, 15, 20, 25 or 30 seconds or any value or range of values therebetween in one second increments upon the surgeon or other healthcare professional taking action to stop deployment. Still further, in an exemplary embodiment that can enable the healthcare professional to control the deployment distance, the implantable device can be provided with different tubes of different lengths, and different tubes could be utilized depending on the depth of insertion desired. Still further, in an exemplary embodiment, the surgeon or other healthcare professional can attach different length tubes to the rest of the body of the device depending on how far he or she seeks the tube to be inserted into the cochlea. Accordingly, embodiments include kits that have different length tubes that the healthcare professional can select or otherwise attach to the rest of the device to have a variable insertion depth. Accordingly, at least some exemplary embodiments do not include stopping the insertion depth of a device that can be inserted further (e.g., such as with a controllable tether as detailed herein), but instead always deploy the tube to the fullest length, and that length is predetermined by selecting one tube over the other. It is also noted that in at least some exemplary embodiments, there pressure relief valves on the device to provide a level of prevention of damage to the cochlea structures and/or to the device overall, such as rupturing the reservoir and/or the tube. By way of example only and not by way of limitation, a pressure release valve with a predetermined pressure relief action can be utilized to release fluid that would otherwise be delivered to the cochlea into another body component, such as for example the middle ear. Accordingly, in an exemplary embodiment, the reservoir 320 and/or the tube 930 that leads to the apparatus 810 can include a pressure relief valve that prevents the therapeutic substance into the middle ear upon a given pressure being reached, which pressure should be the same as that within the apparatus 810 or otherwise very close thereto.

FIG. 13 presents an exemplary embodiment where the outlets 820 (orifices 820) are initially closed or otherwise in a state that significantly restricts the flow of therapeutic substance therethrough. This can have utilitarian value with respect to maintaining a significant pressure within the delivery apparatus 810 so that the delivery apparatus fully or at least effectively fully is deployed as a result of the pressure build up within the delivery apparatus 810. Then, as the pressure continues to build, for example, after full deployment or effectively full deployment, the pressure then opens the outlets 820 so that the outlets 820 expand from the state as seen in FIG. 13 to the state as seen in FIG. 12.

It is also noted that with respect to the orifices detailed herein, the orifices can be adhesively sealed shut, but upon the deployment of the delivery apparatus 810, the adhesive seal will "fail." This can be as a result of the tensile forces on the delivery apparatus in the longitudinal and/or lateral direction and/or can be a result of the pressure increase inside the delivery apparatus. In an exemplary embodiment, adhesive is not used, but instead, there are "weakened" areas of the tube that establish the delivery apparatus 810. These "weakened" areas rip or tear or fail upon deployment (due to the increase in tensile forces and/or pressure within the tube, etc.). In an exemplary embodiment, there are areas of the tube that dissolve when exposed to the perilymph or other body fluids. The dissolution of the areas of the tube create the openings detailed herein. A combination of any of these can be in at least some exemplary embodiments. One or more of these features can also be applied to the porosity of the delivery apparatus 810—the increase in tensile forces and/or pressure can result in the pores opening to increase the flow rate of therapeutic substance out of the delivery apparatus 810.

While the embodiments of FIGS. 12 and 13 have focused on the utilization of outlets in the form of orifices having an oval shape, in other embodiments, other shapes can be used, such as circular shapes, square shapes or other rectangular shapes, pentagon shapes, hexagon, triangular, trapezoid, etc. (note that these are when viewed from the outside/the perspective of FIG. 12, for example). Any configuration that will enable the teachings detailed herein can be utilized in at least some embodiments. Moreover, while openings of relatively large size vis-à-vis the lateral diameter of the delivery apparatus 810 have been utilized, smaller openings can be utilized as well. Conversely, larger openings can be used. Also, a combination of different size openings can be used in a given delivery apparatus 810. In this regard, FIG. 14 presents an exemplary embodiment where smaller and larger openings are utilized relative to the embodiment of FIG. 12. In some exemplary embodiments apparatus 810 can have specific mechanical properties, such as, by way of example only and not by way of limitation, mechanical properties of or akin to a very thin foil of latex, polyurethane (high tear resistance) and/or silicone rubber (good biocompatibility), and in some embodiments, apparatus 810 can be made of one or more of these materials. In some embodiments, the material of apparatus 810 is a flexible structure with very little volume, a low Young's modulus (as low as possible in some embodiments while enabling the teachings herein) and/or a high tear resistance (it can, in some embodiments, be as high as possible that will enable the teachings herein). By rough analogy, a scaled down and leaky condom made from an implantable polymer such as silicone rubber with pores that open when stretched could describe an embodiment of apparatus 810. Also, in some embodiments, such as where apparatus 810 is deployed before inserting a cochlear implant electrode array and/or where the electrode array is used with the apparatus 810 in the cochlear and/or deployed in the cochlea, some materials of the apparatus 810 can be used to hold back on/limit/reduce and/or eliminate stimulation by-products and/or protect the electrode against biofouling, such as while also enabling the electrode array to deliver a charge. In some embodiments, the material of apparatus 810 would be the same material properties as described herein (thin, flexible, a Young's modulus that is low, such as low as possible that will enable the teachings herein, such as one that will come as close as possible to the tissue's modulus of the tissue that may/will interface with the apparatus 810, etc.). In an exemplary embodiment, a laser can be used to create holes in the above mentioned polymer foils (Latex, PU, PDMS), which, in the relaxed state of the deployed tube (inside pressure equals outside pressure, for example) the holes are large enough to let sodium, chloride and potassium ions pass in and out but too small to let larger molecules like amino acids, proteins and cells through. Once the internal pressure increases to deliver the drug or other therapeutic substance, the pores might increase in size according to the teachings herein to let pass the drug or other therapeutic substance. During this phase of increased hole size, the entry of amino acids, protein and cells can be avoided due to the outflux of the therapeutic substance. In some embodiments, conductive polymers like polypyorrol, PEDOT or conductive hydrogels can be used to build all or parts of the tube/apparatus 810. Still, to be clear, any device, system and or method that will enable active pharmaceutical ingredients to be delivered according to the teachings herein can be used in some embodiments.

Referring back to FIG. 7 and FIG. 9, the cochlea wall interface section 191 can be configured to "grip" the cochlea wall and/or the hole therethrough and/or the window so as to hold the local portion of the delivery device 390 stationary (or at least relatively stationary (the window(s) could move a bit)) relative to the cochlea, at least in the longitudinal direction (the delivery device 390 might move laterally, akin to a locked oar on a boat—the oar will not be movable in the outboard or inboard direction, but will be movable forward, backward, upward, and downward). Devices that grip the cochlea wall and/or other tissue are known in the art. Any device that can be utilized to grip or otherwise hold the delivery device in place can be utilized in at least some exemplary embodiments. By way of example only and not by way of limitation, barbed components, spike components, adhesives, sutures, flanges, bone screws, etc., can be utilized to hold the delivery device 390 stationary in at least one direction of the longitudinal direction (e.g., device cannot be inserted anymore but could be pulled in the opposite direction freely, etc.). In an exemplary embodiment, an outer surface of the delivery device 390 can expand, after being inserted into the hole through the bony wall between the interior in the middle ear, so as to establish a compression fit, to secure the delivery device in the hole. In an exemplary embodiment, splints/wedges can be inserted in the hole after and/or along with the delivery device 390 so that the resulting compression and friction will hold the delivery device in the hole. In an exemplary embodiment, the outer surface of the delivery device 390 is in the form of a cone or a wedge, having a diameter that expands with location along the longitudinal direction, such that as the delivery device is inserted into the hole, the delivery device gradually comes into compressive contact with the sidewall of the hole. In an exemplary embodiment, anchors can jut out or structure can jut out (spring loaded, or mechanically moved by moving other components, etc.) to clamp the delivery device in the hole (there could be a flange on the middle ear side and then structure that is on the delivery device but now inside the cochlea due to movement thereof then extends outward and clamps down on the wall). In an exemplary embodiment, one or more resilient ribs or O-rings or seals can be arrayed about the outside diameter of the tube 1020 (they can be part of the tube) and the resilient nature will provide a sufficient securement of the delivery device (the securement does not need to be permanent or robust—it can be securement for a temporary time and/or simply for positioning purposes with respect to an anesthetized human that is not moving in a surgical situation). Any device, system, and/or method that can enable the tube 1020 or other pertinent device of the delivery device to be secured at least with respect to longitudinal movement in the direction the cochlea can be utilized in at least some exemplary embodiments.

In an exemplary embodiment, a stop flange can be located on the extra cochlear portion to hold the stationary portion of the delivery device 390 in place in at least one direction relative to the rest of the cochlea. FIG. 10 depicts an exemplary stop flange 1066 doing such.

Also, in at least some exemplary embodiments, the cochlea wall interface section 191 can be configured to seal the hole/passageway into the cochlea, at least a certain amount.

In view of the above, it can be seen that some embodiments include an apparatus, comprising a therapeutic substance delivery device configured for attachment to a first tissue area internal of a recipient (in some embodiments, this is section 191, interfacing with the bony wall between the middle and inner ear, while in other embodiments, this feature is not present), the delivery device configured to enable movement of a therapeutic substance outlet (e.g., any one of orifices 820 or pores 823 as will be describe below, or permeable sections 824 as will also be detailed below) of the delivery device proximate a second tissue area away from the first tissue area (e.g., to a location at the 180, 270 or 360 or more degree turn within the cochlea) more on this bellow) after attachment to the first tissue area to deliver the therapeutic substance from the outlet while implanted in the recipient. This as opposed to an embodiment where the delivery device is merely, for example, delivery tube 206 which can be inserted into the cochlea a given distance, where there would be no attachment to a first tissue area internal of a recipient, or if there is attachment, there is no movement of an opening to the second tissue area after attachment.

It is briefly noted that while the above refers to an outlet, this does not mean that this excludes a device that includes two or more outlets. The outlet referred to in the above is simply a reference outlet so that movement can be gauged. In this regard, there could be two or more outlets, were one of the outlets may not necessarily move. As long as one outlet moves, such as covered by the above explanation.

In an exemplary embodiment, the attachment can be to the wall of the cochlea as detailed above, while in other embodiments, the attachment can be to a location in the middle ear away from the wall of the cochlea. In at least some exemplary embodiments, any attachment that is inside the recipient that can enable the teachings detailed herein can be utilized in at least some exemplary embodiments.

That said, in at least some exemplary embodiments, such as where there is no attachment, one portion of the delivery device is held stationary relative to the longitudinal direction of the cochlea, and then the outlet is deployed. The holding stationary can be with a surgeon's hand or with a forceps or simply by gravity.

In an exemplary embodiment, the attachment is permanent, while in other embodiments, the attachment is only temporary.

In some embodiments of the apparatus, the apparatus is configured such that the movement includes expanding an expandable component so that the outlet moves with expansion of the expandable component. In an exemplary embodiment, the movement can be a result of unfolding, stretching and/or flexing of the delivery apparatus 810. In an exemplary embodiment, the movement includes expanding a flexible component so that the outlet moves with expansion of the flexible component.

In some exemplary embodiments of the apparatus, the delivery device includes a catheter configured to transport therapeutic substance to the fixed location. In an exemplary embodiment, the delivery device is configured to enable transportation of the therapeutic substance from the fixed location to the outlet via a component different from the catheter. With respect to at least some of the exemplary embodiments herein, the component different from the catheter can be a tube that includes the outlet.

In an exemplary embodiment of one or more of the apparatuses disclosed herein, the tube delivery apparatus 810 can be any (or other structure—delivery apparatus 810 can be any structure that can enable the teachings detailed herein) includes a plurality of outlets spaced apart from each other at least along a longitudinal axis of the tube (or laterally, such as the embodiment of FIG. 14 depicts), the outlets configured to enable delivery of the therapeutic substance from the outlets. Further, in some embodiments of the apparatuses disclosed herein, the apparatus is configured to deploy the tube (or whatever embodiment is utilized for the delivery apparatus 810) from a first position where a majority of the outlets are proximate the first tissue area to a second positon where a majority of the outlets are located away from the first tissue area. For example, this is achieved when the device is undeployed from the state depicted in FIG. 11 to the state depicted in FIG. 12, for example. In an exemplary embodiment, the apparatus is configured to deploy the tube (or whatever embodiment is utilized for the delivery apparatus 810) from a first position where at least 5, 10, 15, 20, 25, 30, 35, 40, 45, 50, 55, 60, 65, 70, 75, 80, 85, 90, 95 or 100%, or any value a range of values therebetween in 1% increments, of the outlets and/or of the collective area of the outlets when opened at their maximum design opening and/or opened at their maximum when used in a method and/or the percentage of diffusion or elution area and/or outlet area is proximate the first tissue area to a second positon where at least 5, 10, 15, 20, 25, 30, 35, 40, 45, 50, 55, 60, 65, 70, 75, 80, 85, 90, 95 or 100% value a range of values therebetween, or any value a range of values therebetween in 1% increments, of the outlets and/or of the collective area of the outlets when opened at their maximum design opening and/or opened as their maximum when used in a method and/or the percentage of diffusion or elution area and/or outlet area are located away from the first tissue area.

Still further by way of example only and not by way of limitation, in an exemplary embodiment of one or more of the apparatuses detailed herein, the apparatus is configured for rigid attachment at the first tissue location (e.g., via a flange that is rigidly attached to tube 1020, where there can be a bone screw or the like or adhesive to attach the flange or any other element of the device 390 to the bone, as noted above, in an exemplary embodiment, the first tissue location is a location at or proximate a wall of a cochlea that separates an interior of the cochlea from a middle ear of the recipient. Still further, in an exemplary embodiment, this apparatus or any other apparatus can be, in some embodiments, configured to move the outlet so that the outlet is moved from the first tissue location, inside a duct of the cochlea, to a location that is at least one full cochlea turn or at least $\frac{1}{4}$, $\frac{1}{2}$, $\frac{3}{4}$, 1.25, 1.5, 1.75, 2, 2.25, or more turns from the most basil location of the cochlea, while the apparatus is fixed at the first location. This can also be the case with respect to when the apparatus is simply held at the first location and/or simply does not move relative to the first location in the longitudinal direction of the cochlea (again, the oar analogy) during deployment.

An exemplary embodiment, referring to FIG. 11, all or part of section 193*ish* would be located inside the cochlea prior to deployment, and then deployment would commence. The above said, in some embodiments, deployment can commence while the tube 1020 is being inserted into the cochlea as well. That is, the tube 1020 can be moved into the cochlea in the longitudinal direction while the delivery apparatus 810 is being deployed and thus also moving in the longitudinal direction.

In at least some exemplary embodiments, the apparatuses detailed herein can include sections that elute and/or diffuse and/or enable the elution and/or diffusion of therapeutic substance from inside the delivery apparatus 810 to outside the delivery apparatus 810.

FIG. 16 presents an exemplary delivery apparatus that includes sections 824 that can be diffusion and/or elution sections of the delivery apparatus 810. Here, the therapeutic substance will diffuse through and/or elute from the wall of the delivery apparatus 810 at the sections, but will not do so (or effectively only negligibly do so at other sections). The sizes and shapes of the diffusion and/or elution sections can be any shape, and can have any one or more or are all of the shapes detailed above with respect to the orifices 820 (e.g., the oval shapes of FIG. 12 can represent diffusion/elution zones, or the oval shapes of FIG. 12 can represent zones where there is no diffusion/elution, for that matter). As seen in FIG. 16, the diffusion/elution zones 824 can be spaced along the longitudinal length of the delivery apparatus 810. The spacing can be uniform or non uniform, both with respect to the longitudinal axis of the delivery apparatus 810 and to the lateral direction as well. The diffusion/elution zones can be of equal areas or can have different areas at different locations along the longitudinal length.

It is noted that in at least some exemplary embodiments, the different sections can have different diffusion/elution properties. FIG. 17 presents an exemplary embodiment where there are four different sections (also referred to herein as zones). Section 824 has an elution/diffusion property such that the mass and/or volumetric flow rate at a given pressure or otherwise during normal usage is less than or greater than that of section 825, which is less than or greater than that of section 826, which is less than or greater than that of section 827, etc. While four (4) different elution/diffusion zones are depicted in FIG. 17, other embodiments can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 or more distinct different diffusion/elution zones with respect to their being a space between the zones and/or having different properties, at least relative to a zone that is proximate another zone. In an exemplary embodiment, zone 824 can be contiguous with zone 825, and the differences between the two zones are the properties. Moreover, the zones can overlap with respect to the longitudinal direction. Any arrangement that can enable the teaching detailed herein can be pleasantly some exemplary embodiments.

Some methods of diffusion can be enabled via the use of a porous surface/wall structure of the delivery apparatus 810.

It is briefly noted that while the embodiments of FIGS. 16 and 17 depict discrete sections/zones, in an exemplary embodiment, the entirety of the delivery apparatus can be a diffusion and/or elution zone. An exemplary embodiment, the properties across the entire zone can be the same, while in other embodiments, the properties can vary. In an exemplary embodiment, less than, greater than or equal to 5, 10, 15, 20, 25, 30, 35, 40, 45, 50, 55, 60, 65, 70, 75, 80, 85, 90, 95, or 100%, or any value or range of values therebetween in 1% increments can make up elution and/or diffusion zone(s).

In at least some exemplary embodiments of the apparatuses detailed herein, the apparatus includes a drug permeable membrane that is configured to be deployed in a cochlea and function as a one way filter (in some embodiments but not others) that becomes permeable to the drug or at least more permeable to the drug as a result of increasing a pore size of a plurality of pores in the membrane due as a result of increased pressure inside the delivery apparatus and/or as a result of tensile forces in the membrane increasing upon at least one of deployment or pressurization of the therapeutic substance to be delivered. Here, the outlet corresponds to one or more of the plurality of pores.

In at least some exemplary embodiments of the apparatuses detailed herein, the apparatus includes one or more diffusion and/or elution sections configured to be deployed in a cochlea and function as a one way filter (in some embodiments but not others) that elutes and/or diffuses the drug and/or at least more of the drug as a result of increased pressure inside the delivery apparatus and/or as a result of tensile forces in the membrane increasing upon at least one of deployment or pressurization of the therapeutic substance to be delivered.

In an exemplary embodiment, the permeability and/or diffusivity and/or eluteability, on a mass flow rate or a volumetric flow rate, all other things being equal, increases by at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 125, 150, 175, 200, 250, 300, 350, 400, 450, 500, 600, 700, 800, 900, or 1000 times or more upon deployment, including full deployment and/or pressurization, including full pressurization, relative to that which was the case prior thereto. In an exemplary embodiment, pressurization can increase by at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 125, 150, 175, 200, 250, 300, 350, 400, 450, 500, 600, 700, 800, 900, or 1000 times to full pressurization relative to that which was the case prior to deployment.

In an exemplary embodiment, there is one or more of the apparatuses detailed herein, wherein the apparatus is a cochlea therapeutic substance delivery device configured to extend the outlet along a duct of the cochlea and the apparatus is configured to variably control a distance of the outlet extension into the cochlea to locate the outlet adjacent a specific location inside the cochlea. In an exemplary embodiment, this can be achieved by varying the pressure or otherwise controlling the pressure inside the delivery apparatus 810. In an exemplary embodiment, such as seen in FIG. 18, the delivery device 390 can include a cable or other tether 883, located inside the delivery apparatus 810, the length of which can be adjusted via a spool 885, so as to extend and/or retract the tether. The length of the tether can control the length of deployment/extension of the delivery apparatus 810. While the embodiment depicted in FIG. 18 as the tether attached to the most distal end of the delivery apparatus 810, and alternate embodiment, the tether can be located at any location along the longitudinal length of the delivery apparatus 810. This can have the effect of, for example, controlling the location of the "bunching" of the material of the delivery apparatus 810. Typically, the bunching will occur at a location proximate and/or inboard of the attachment location of the tether. Why locating the attachment portion of the tether at different locations, the area within the cochlea where there is full expansion/deployment of a local section of the delivery apparatus 810 can be varied. By way of example only and not by way of limitation, in the embodiment of FIG. 18, the device will likely not have the optimum or maximum therapeutic substance delivery at the bunch locations relative to the other locations. Accordingly, locations inboard of the bunch locations will have a delivery regime that is "more normal." Conversely, if the tether was attached in the middle, for example, the bunching would occur inboard of the attachment location, and at least the portions located distal of the attachment location would have a more normal therapeutic substance delivery regime.

While the embodiment of FIG. 18 utilizes a tether, in some embodiments, other devices and systems and/or methods can be utilized to control the distance of extension. In an exemplary embodiment, the material of the delivery apparatus can be configured so that the flexibility and/or the expandability can be varied, such as varied with respect to internal pressure (the greater the pressure, the greater the expansion). An exemplary embodiment, an electric charge or some other phenomenon can be applied to bury the flexibility under expandability of the delivery apparatus.

In an exemplary embodiment, any one or more of the apparatuses detailed herein can include a first structure configured to be attached to tissue internal of a recipient (again, for example, the flange, or the tube 1020 with some adhesive thereon, etc.), a second structure (e.g., delivery apparatus 810, for example) configured to be supported by the first structure in an initial state during a first temporal period, and configured to be deployed from the first structure in a deployed state during a second temporal period after the first temporal period. In an exemplary embodiment, the apparatus is a therapeutic substance delivery device configured to deliver therapeutic substance from the second structure to a location remote from the first structure during and/or after deployment of the second structure. Further, in an exemplary embodiment, the second structure is at least one of in or controllably placeable in fluid communication with the first structure (such as by the valve detailed above with respect to FIG. 5, or by another valve that can be controlled from the outside of the recipient and/or via control regime of an implanted device (e.g., a processor or other electronic circuitry configured to control the flow of substance into the delivery apparatus 810 in this regard, embodiments can include electronic circuitry or other componentry that can enable the automated or semiautomated or preprogrammed control of the delivery of the therapeutic substance into the delivery apparatus 810—this can further be utilized to control the rate of delivery of a therapeutic substance therefrom and to the cochlea, such as by varying the pressure and/or mass flow rate and/or volumetric flow rate, etc., By, for example, variably opening and/or closing and/or adjusting the amount of opening and/or closing of the valve, such as where there is a back pressure upstream of the valve—further comments on embodiments, this hardware and/or firmware, etc. can be utilized to control pump to affect a similar result and/or the same result)) so that therapeutic substance can travel from the first structure to the second structure.

In at least some exemplary embodiments of the apparatuses detailed herein, the first structure includes a catheter to channel the therapeutic substance to the second structure and at least a portion of the second structure is located in the catheter when the second component is supported by the first component prior to deployment. Further, as detailed above, in some embodiments, the second structure is a tube that is ejected from the catheter via a pressurization within the catheter during deployment. It is briefly noted that while at least some exemplary embodiments depict the apparatus 810 being attached to the tube on the inside of the tube, in an alternate embodiment, the apparatus 810 is attached to the tube on the outside of the tube (e.g., akin to a nozzle being inserted into an end of a balloon) and/or at the very end of the tube. Any arrangement that can enable fixation of apparatus 810 to tube 1020 and/or the placement of the apparatus 810 and the communication with the tube 1020 can be lies in at least some exemplary embodiments.

Figure 30:
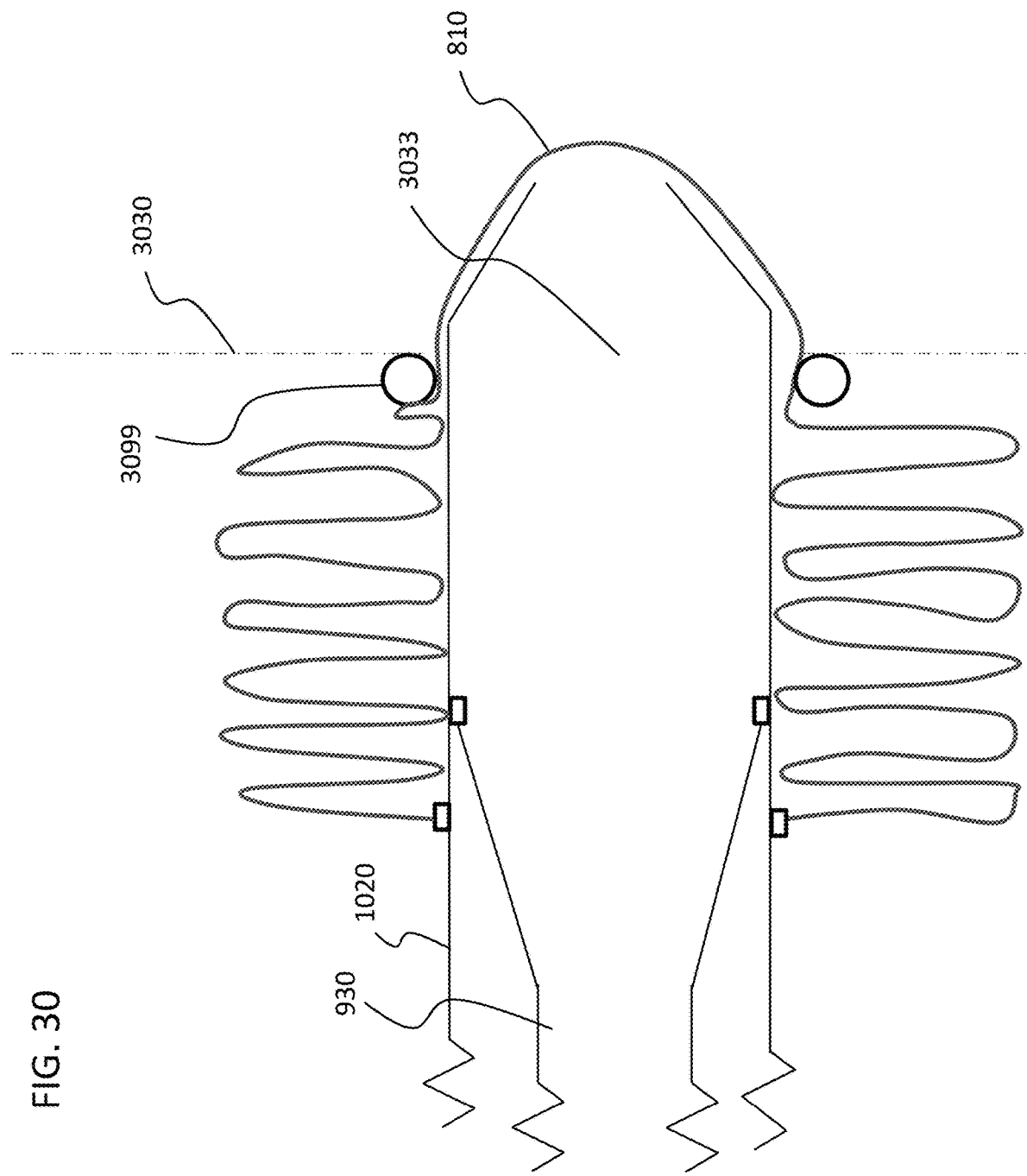
FIGS. 30-32 present additional embodiments.
Figure 31:
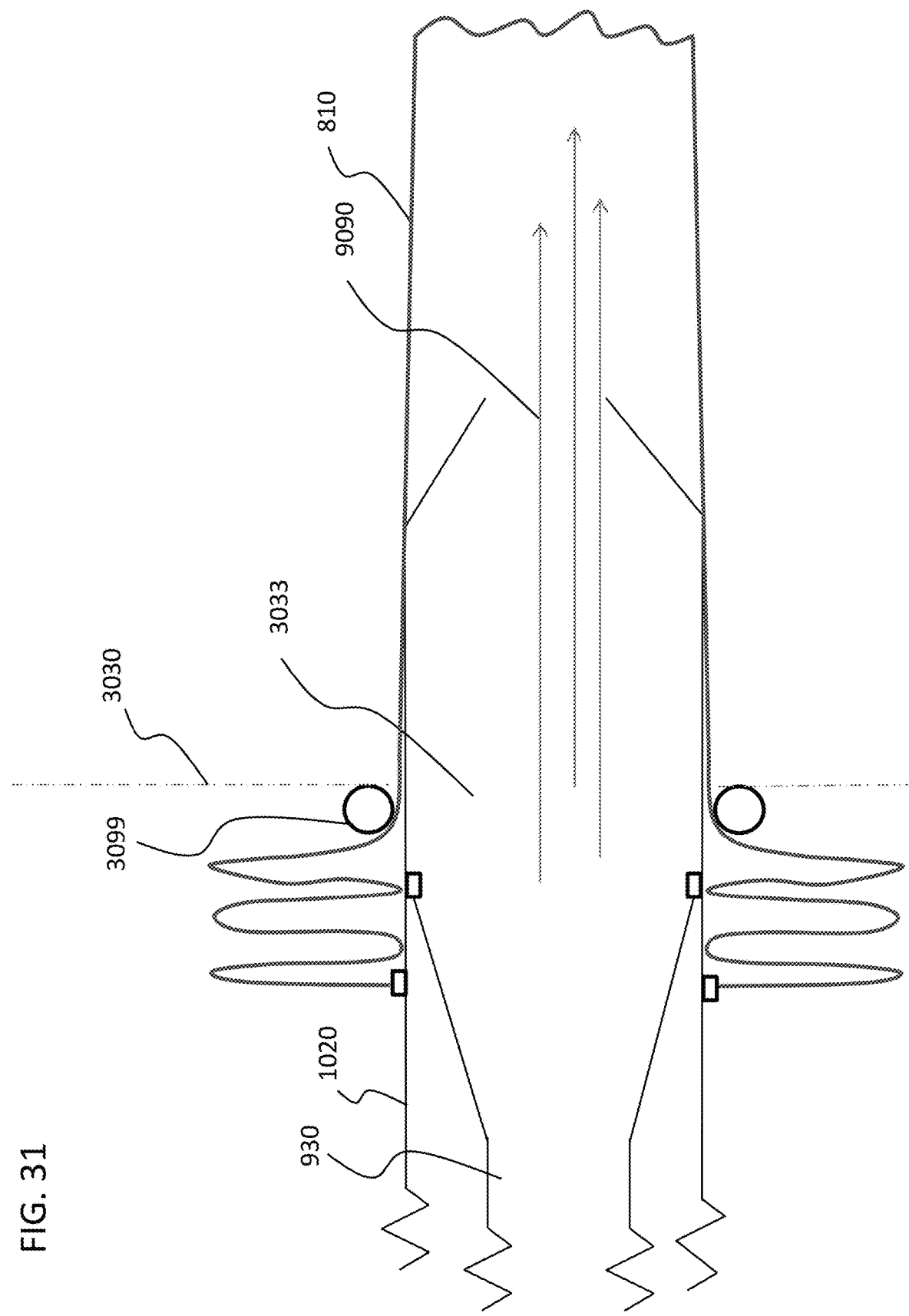

To this end, FIGS. 30 and 31 depict an exemplary embodiment of an arrangement where the apparatus 810 is attached to the tube 1020 at the location on the outside of the tube 1020. In this exemplary embodiment, the apparatus 810 is bunched up over the tube prior to insertion into the cochlea (and even after, as will be described below, albeit a bit less bunched)/at the initial insertion of the tube 1020 into the cochlea, as seen in FIG. 30, where reference 3030 represents the wall between the middle ear and the inner ear, and reference 3033 represents a hole through that wall into the cochlea (where the cochlea is represented by the area to the right of the wall 3030 and FIG. 30). In an exemplary embodiment, the tube 1020 is placed through the hole 3033 in the cochlea with the apparatus 810 over the end of the tube as shown in FIG. 30. O-ring(s) 3099 are utilized to seal the hole 3033 in the wall 3030 to prevent and/or limit the amount of perilymph that escapes into the middle ear. This can also form a seal against the apparatus 810 (more on this below). The configuration of FIG. 30 is exemplary of the device prior to insertion of the device in the cochlea and/or in the middle ear. In this regard, in an exemplary embodiment, a surgeon or other healthcare professional brings the device in the configuration seen in FIG. 30 to the recipient/patient and then inserts the device into the cochlea or otherwise placing the device proximate the entrance into the cochlea (in some embodiments, the tube 1020 is not put into the cochlea).

Then, in some embodiments, the tube 1020 is pushed forward into the cochlea bit more than that seen in FIG. 30, such as by way of example the amount shown in FIG. 31 (but again, in some embodiments, the tube 1020 does not enter the cochlea). As seen in FIG. 31, the O-ring 3099 moves up along the tube 1020 to maintain the seal. In an exemplary embodiment, O-ring 3099 also seals the apparatus 810 against the tube 1020.

In this exemplary embodiment, fluid flow is then introduced through the conduit 930, and thus through tube 1020, which fluid flow causes the apparatus 810 to extend in the longitudinal direction, as seen by way of example in FIG. 31, where arrows 9090 represent the fluid flow. As seen, apparatus 810 expands into the cochlea by unfurling the bunched area. More specifically, the pressure increase inside the apparatus 810 owing to the fluid flow and/or the increase of fluid volume inside the apparatus 810 causes the apparatus 810 to extend in a manner analogous to the teachings detailed above. In an exemplary embodiment, the internal pressure can increase and swell the apparatus 810, and the apparatus 810 can function according to the teachings detailed herein.

In an exemplary embodiment, the arrangement of FIGS. 30 and 31 can be utilized for controlling deployment distance into the cochlea. In an exemplary embodiment, the apparatus 810 can be marked with indicia along the longitudinal length of the apparatus 810, which indicia can be visible to the surgeon or other healthcare professional during the insertion process. By monitoring the indicia, the surgeon can estimate or otherwise determine how far the apparatus 810 has been inserted into the cochlea. Upon a determination that the apparatus 810 has been inserted a desired depth in the cochlea, the surgeon can stop further deployment by stopping the flow of fluid 9090 or clamping down on O-ring 3099 or some other apparatus, such as a clamp that is adjustable, to stop further unfurling of the apparatus 810, and thus stops further insertion of the apparatus 810. Accordingly, an exemplary embodiment includes a stop-deploy-start delivery mechanism.

Figure 32:
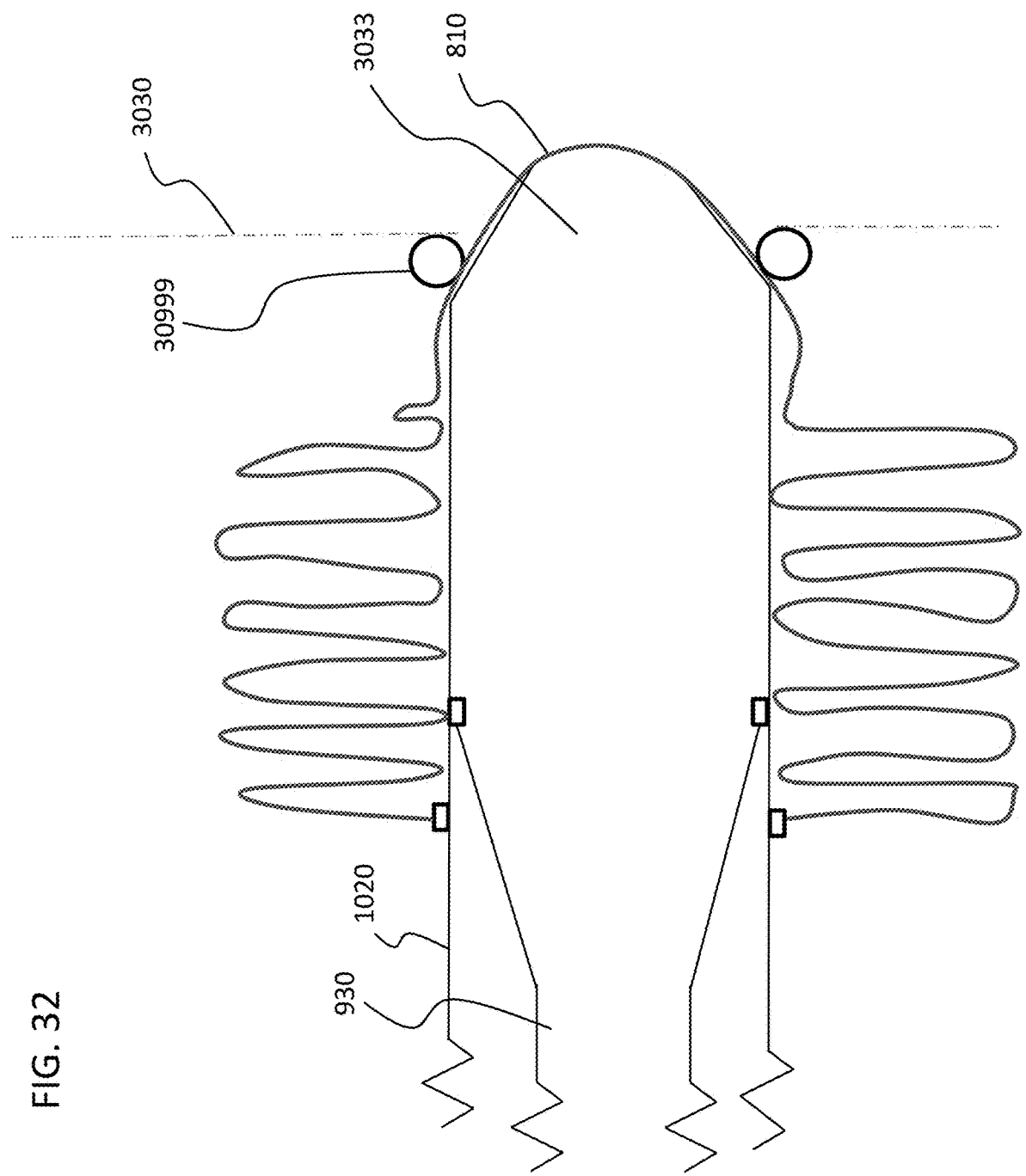

FIG. 32 presents another exemplary embodiment which is a variation of the embodiments of FIGS. 30 and 31, where the O-ring 3099 is replaced with an O-ring 30999, which has a smaller diameter in a relaxed state or a semi relaxed state than that of O-ring 3099. In this regard, this exemplary embodiment, the O-ring is located initially at the beveled edge of the tube 1020. In an exemplary embodiment, the tube 1020 is inserted into the hole into the cochlea and/or placed against the hole, and the wall pushes the O-ring 30999 up the bevel and onto the cylindrical portion of the tube 1020. In this exemplary embodiment, the O-ring 30999 does not provide compression onto the outer surface of apparatus 810 at the distal portions of the tube 1020 when on the beveled portion, or at least does not provide too much compression thereon. In this exemplary embodiment, this will permit the apparatus 810 to slide through the interior of the O-ring 30999, if there is any contact at all. When the O-ring 30999 is held against the wall 3030 that establishes a boundary between the middle ear and the inner ear, as seen in FIG. 32, the O-ring 30999 is prevented from being pushed to the right during deployment of the apparatus 810. In an exemplary embodiment, the surgeon or other healthcare professional monitors the deployment of the apparatus 810, such as by monitoring the indicia on the outer surface of the apparatus 810, and upon a determination that the apparatus 810 has been deployed a certain desired amount, the surgeon or other healthcare professional pushes the tube 1020 forward into the cochlea or otherwise towards the cochlea, which causes the O-ring 30999 to rollup or otherwise travel along the distal length of the tube 1020 towards the proximal end, and because the outer diameter of the tube 1020 increases relative to the beveled edge, this creates additional tension on the O-ring 30999, which provides compression onto the apparatus 810 and traps apparatus 810 between the outer surface of the tube 1020, thus preventing further deployment. That is, upon a determination that the apparatus 810 has been deployed a sufficient distance, the surgeon or other healthcare professional gives the tube a slight forward push to stop further deployment. In an exemplary embodiment, the O-ring never leaves the beveled edge, but instead, simply moves up further along the beveled edge to a point where the tension is increased sufficiently to stop further unfurling of the apparatus 810.

In an exemplary embodiment, one or more or all of the above-detailed deployment states is achieved relative to a pre-deployment state by increasing the pressure inside conduit 930 (or tube 206) by at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5 6, 7, 8, 9, 10, 11, 12, 13, 14, 15, 20, 25, 30, 35, 40, 45, or 50 or more times or any value range of either between in 0.01 increments, relative to the value prior to deployment. In an exemplary embodiment, one or more or all of the above-detailed deployment states is achieved relative to a pre-deployment state by increasing the mass flow rate and/or the volumetric flow rate of the therapeutic substance through the conduit 930 at the location where the conduit ends by at least 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5 6, 7, 8, 9, 10, 11, 12, 13, 14, 15, 20, 25, 30, 35, 40, 45, or 50 or more, or any value or range of values therebetween in 0.01 increments relative to a pre-deployment state. In an exemplary embodiment, one or more or all of the above-detailed deployment states is achieved relative to a pre-deployment state by increasing the amount (volume and/or mass) of therapeutic substance located inside the delivery apparatus 810 by 1, 1.1, 1.2, 1.3, 1.4, 1.5, 1.6, 1.7, 1.8, 1.9, 2, 2.5, 3, 3.5, 4, 4.5, 5 6, 7, 8, 9, 10, 11, 12, 13, 14, 15, 20, 25, 30, 35, 40, 45, 50, 60, 70, 80, 90, 100, 125, 150, 175, 200, 250, 300, 350, 400, or 500 times or more, or any value or range of values therebetween in 0.1 increments relative to a pre-deployment state. It is briefly noted that in the scenario where the initial value is zero, the increase would result in an increase more than the last number noted (because we would have a value divided by zero, which would be an infinite number).

In an exemplary embodiment of the apparatuses detailed herein, the first structure can include a catheter to channel the therapeutic substance to the second structure, as noted above, and further, at least a portion of the second structure is located about a portion of the first structure that establishes a conduit of the catheter when the second component is supported by the first component prior to deployment. This is seen, for example, in FIG. 11. In this embodiment, 1020 can be the catheter.

In an exemplary embodiment, 1020 is the delivery tube. In this regard, the delivery device 390 can be a portion of the tub (the distal portion) and the seal 1005 and the delivery apparatus 810. Additional components can be located on the tube, such as the aforementioned stops or flanges or seals (to seal the opening—the seal(s) could be located about the outside of the tube 206. In some embodiments, the tube 1020 (or tube 206) is sufficiently flexible such that it self seals in the hole in the cochlea (e.g., the hole could be slightly smaller than the maximum outer diameter of the tube 206/1020, thus sealing the hole).

In view of the above, in some embodiments, there is the apparatus as disclosed herein or a variation thereof, wherein the second structure is a tube that is longitudinally expanded off the portion of the first structure that established the conduit during deployment via pressurization of a fluid in the catheter, which is in fluid communication with the second structure during expansion of the tube.

In at least some exemplary embodiments of the apparatuses detailed herein, the apparatus is an inner ear therapeutic substance delivery apparatus, or another type of delivery apparatus for that matter—again, as noted above, in at least some exemplary embodiments, the teachings detailed herein can be applicable to other types of medical devices other than devices that interface with the cochlea, such as by way of example only and not by way of limitation, devices that interface with the heart with the kidneys or the bladder or arteries or veins, or the eye, or the brain, etc., and the second structure (e.g., the delivery apparatus 810) is biodegradable when exposed to perilymph. By way of example only and not by way of limitation, in an exemplary embodiment, at least 50, 55, 60, 65, 70, 75, 80, 85, 90, 95, or 100% of the delivery apparatus 810 will dissolve within 1, 1.5, 2, 2.5, 3, 3.5, 4, 4.5, 5, 5.5, 6, 6.5, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, or 100 or more days for any value or range of values therebetween in 0.1 day increments from the time that the delivery apparatus 810 is first exposed to the perilymph from the time that delivery apparatus 810 is first deployed. The aforementioned percentages can be calculated based on length remaining and/or mass remaining and/or surface area remaining, and can be determined by, for example, removing the delivery device 390 from the cochlea and analyzing what comes out with the device and/or utilizing imaging systems. In this regard, in some embodiments, the material of the delivery apparatus can include radioscopic material or material that fluoresces for material that will show up on an x-ray, etc. or a heavy metal (e.g., platinum, for example), that will aid in imaging. Indeed, Cora learned all of this is that in some embodiments, the delivery apparatus having these features can have utilitarian value with respect to imaging for the purposes of determining how far the delivery apparatus 810 has been deployed into the cochlea/the state of deployment, etc. By way of example only and not by way of limitation, a platinum bead can be located at the very tip of the delivery apparatus 810. By way of example only and not by way of limitation, platinum beads can be located every 5 mm along the length of the delivery apparatus 810. By utilizing imaging or other systems, the location of the beads can be plotted to determine how far the delivery apparatus 810 has been inserted into the cochlea.

In an exemplary embodiment, a dissolvable cap and/or a movable, jettisonable cap, can be located at the end of section 193*ish*, so as to protect the delivery apparatus 810 from the perilymph until the desired time for the delivery apparatus 810 to be exposed thereto. In an exemplary embodiment, the cap can be dissolvable, as just detailed, while in other embodiments, the cap can be located on a hinge or a flexible portion such that the cap will open, by rough analogy to the outer doors of a torpedo tube on a submarine (the deployment of the delivery apparatus 810 will push the cap off or open). Still further, in an exemplary embodiment, the cap can be a rupturable structure, such as a membrane or the like, which will rupture upon the beginning of deployment/the increase of pressure within the delivery apparatus 810.

In an exemplary embodiment, one or more of the apparatuses detailed herein is configured such that second structure is a thin-skinned tube that has orifices therein through which the therapeutic substance is delivered to the recipient. Further, by way of example only and not by way of limitation, the apparatuses can be configured to vary a shape of the orifices to control a rate of flow of the therapeutic substance through the orifices to control a therapeutic substance delivery rate to the recipient, consistent with the teachings detailed above.

Consistent with the teachings herein, in some embodiments, the second structure is a membraned walled tube, and the therapeutic substance diffuses through the membrane walled tube to deliver the therapeutic substance to the recipient. Consistent with the teachings herein, in some embodiments, the second structure is a thick-walled tube or a medium thickness tube or a thin walled tube, and the therapeutic substance elutes from the walled tube to deliver the therapeutic substance to the recipient.

In an exemplary embodiment, the therapeutic substance is API, and is contained in the tube's wall. In an exemplary embodiment, the therapeutic substance could be mixed into a silicone rubber that forms tube 810. In an embodiment, the therapeutic substance could elute into the perilymph after the tube is deployed/once the tube comes into contact with the perilymph.

In an exemplary embodiment, the tubes could have a thickness of less than, greater than or equal to 0.005, 0.006, 0.007, 0.008, 0.009, 0.01, 0.15, 0.02, 0.25, 0.03, 0.35, 0.04, 0.45 0.05, 0.06, 0.07, 0.08, 0.09, 0.1, 0.15, 0.2, 0.25, 0.3, 0.35, 0.4, or 0.5 mm or more, or any value or range of values therebetween in 0.001 mm increments. In some embodiments, a relatively thicker walled tube would be utilized for elution relative to that which would be utilized for diffusion.

In some exemplary embodiments, the material that is delivered into the delivery apparatus is a particulate that can "flows." By way of example only and not by way of limitation, silicone beads formed with therapeutic substance can flow into the delivery apparatus 810, from which the therapeutic substance elutes over time. That said, in some embodiments, the particles are "pure" therapeutic substance particles (or at least "pure" active and inactive ingredients), which can be flown into the delivery apparatus 810. In some embodiments, these particles are what expands the delivery apparatus 810, while in other embodiments, an expanding medium is utilized, followed by the particles. In an exemplary embodiment, a slurry of the particles and the expanding medium can be utilized.

In an exemplary embodiment, therapeutic substance can be mixed into the biodegradable material of the tube or otherwise the delivery apparatus and is released as the tube/delivery apparatus dissolved in the perilymph. This could be the primary regime of delivery or could be a secondary regime of delivery in that therapeutic substance can also be delivered from inside the tube to outside the tube in a manner according to the teachings detailed herein. By way of example only and not by way of limitation, this could be a way to provide two or more therapeutic substances into the cochlea, a first being delivered from inside the tube to outside the tube, and a second and/or a third and/or fourth, etc., being delivered as a result of the tube dissolving in the cochlea (or other body location).

In view of the teachings herein, it is understood that in at least some exemplary embodiments, there is an apparatus comprising a means for securing the apparatus to tissue (e.g., any of the structure and devices and systems disclosed herein to secure tube 1020 or the stationary part of the delivery device 392 the wall between the outer ear and the middle ear, any device disclosed herein that attaches to the inner ear that can provide securement (e.g., a spring loaded device that extends outward to the lateral wall and the opposite wall, for example, or a non-spring-loaded device that is mechanically actuated and/or electrically actuated—a piezo device or a MEMS device can be used inside the cochlea or outside the cochlea for that matter, which can extend and/or retract to provide friction forces and/or gripping forces and/or penetrative forces in some embodiments (that will act as an anchor—fine spikes can be used or fine barbs can be used that are brought into contact with tissue inside the cochlea and/or on the bony wall, etc.). Further, in an exemplary embodiment of this apparatus, there is a means for delivering therapeutic substance inside a cochlea.

In an exemplary embodiment of this apparatus, there can be reservoir, which can be a refillable reservoir, and/or a catheter wherein the reservoir, refillable or otherwise, is in fluid communication with the catheter, and the catheter is in fluid communication with the means for delivering therapeutic substance. Further, in at least some exemplary embodiments, the apparatus is configured such that therapeutic substance contained in the reservoir is delivered to the means for delivering therapeutic substance via the conduit for delivery by the means for delivering therapeutic substance inside the cochlea.

In at least some exemplary embodiments of the apparatus is detailed herein, there is a catheter, as detailed herein. In an exemplary embodiment, the catheter is in fluid communication with the means for delivering therapeutic substance, and the apparatus is configured with a component that enables opening of the cochlea without drilling and/or enables a window of the cochlea to be pierced, thereby providing access to the cochlear for movement of the means for delivering therapeutic substance into the cochlea and is configured to seal the access location. This said, it is also noted that in at least some exemplary embodiments, there is utilitarian value with respect to maintaining a pressure inside scala tympani the same during insertion, or at least ensuring that the pressure does not change too much. In at least some exemplary embodiments, this can be achieved by a slow insertion that is slow enough for the displaced volume of perilymph to leave the cochlea through natural mechanisms and/or the device has some sort of pressure release valve at the access location to release the displaced perilymph into the middle ear. This is a different pressure release valve as opposed to one above for releasing therapeutic substance in case the internal pressure inside the device goes too high. Accordingly, in an exemplary embodiment, there can be a second passageway in the device that extends from inside the cochlea to the middle ear, and this passageway can have a pressure relief valve or the like that opens to allow perilymph or the like to flow from inside the cochlea into the middle ear.

An exemplary embodiment, the end of the tube 1020 can be pointed, like the end of a skin penetrating drug delivering needle. In an exemplary embodiment, the distal end of the tube 1020 can have a screw like feature and/or can have a drill like feature such that, when the tube 1020 is rotated, the tube will "bore" into the cochlea from the middle ear into the inner ear. In an exemplary embodiment, the drill/screw feature can be configured so that it will turn relative to the tube 1020 so that the tube 1020 need not be twisted or turned. In an exemplary embodiment, this drill or screw like feature can be powered by a miniature electric motor and/or a hydraulic motor and/or can be actuated as a result of pressure placed onto tube 1020 by the surgeon's hand or other device. Mechanical transmission devices can be utilized to transfer the force in the longitudinal direction to rotational force.

It is also noted that in at least the embodiment associated with the above mentioned feature, the feature can also result in securement of the delivery device 390 at the tissue location.

In an exemplary embodiment, the apparatus is configured to generate a pressure increase inside the means for delivering therapeutic substance so as to expand the means for delivering in a longitudinal direction, and also the means for delivering includes a therapeutic substance permeable membrane through which the therapeutic substance travels to reach tissue of the cochlea. Here, in some exemplary embodiments, there can be a symbiotic relationship between the pressure increase and the permeability of the membrane. In this regard, the increase in pressure can also result in an increase in the permeability of the membrane or otherwise an increase in the flow rate (mass or volume) relative to the which is the case prior to the pressure increase. The pressure increase can also open the orifices in the tube, expanding the orifices from the closed position to the open position. Thus, in some embodiments, the outlet(s) of the tube 810 can be initially closed, and/or small enough to allow the pressure to increase enough for deployment. Once deployed the pressure increases further which drives the fluid through the unchanged outlets or the outlet(s) open or increase in size or both to allow the therapeutic substance to be delivered.

In an exemplary embodiment, there is an apparatus is detailed herein, which is a cochlear implant electrode array, that includes one or more or all of the features detailed herein. In this regard, and in an exemplary embodiment, the cochlear implant electrode array can include a means for delivering therapeutic substance that is attached to the cochlear implant electrode array at a location that is at a distal portion of the electrode array. By way of example only and not by way of limitation, in an exemplary embodiment, the distal end of the electrode array can include a section corresponding to section 193*ish*, where the conduit 930 can extend through and/or along the length of the electrode array. The principles of operation can be the same vis-à-vis the deployments of the delivery apparatus 810 as disclosed herein with respect to a dedicated standalone therapy takes up the delivery device 390, except that the delivery apparatus 810 extends/is deployed from a location further within the cochlea relative to that which would otherwise be the case.

Figure 19:
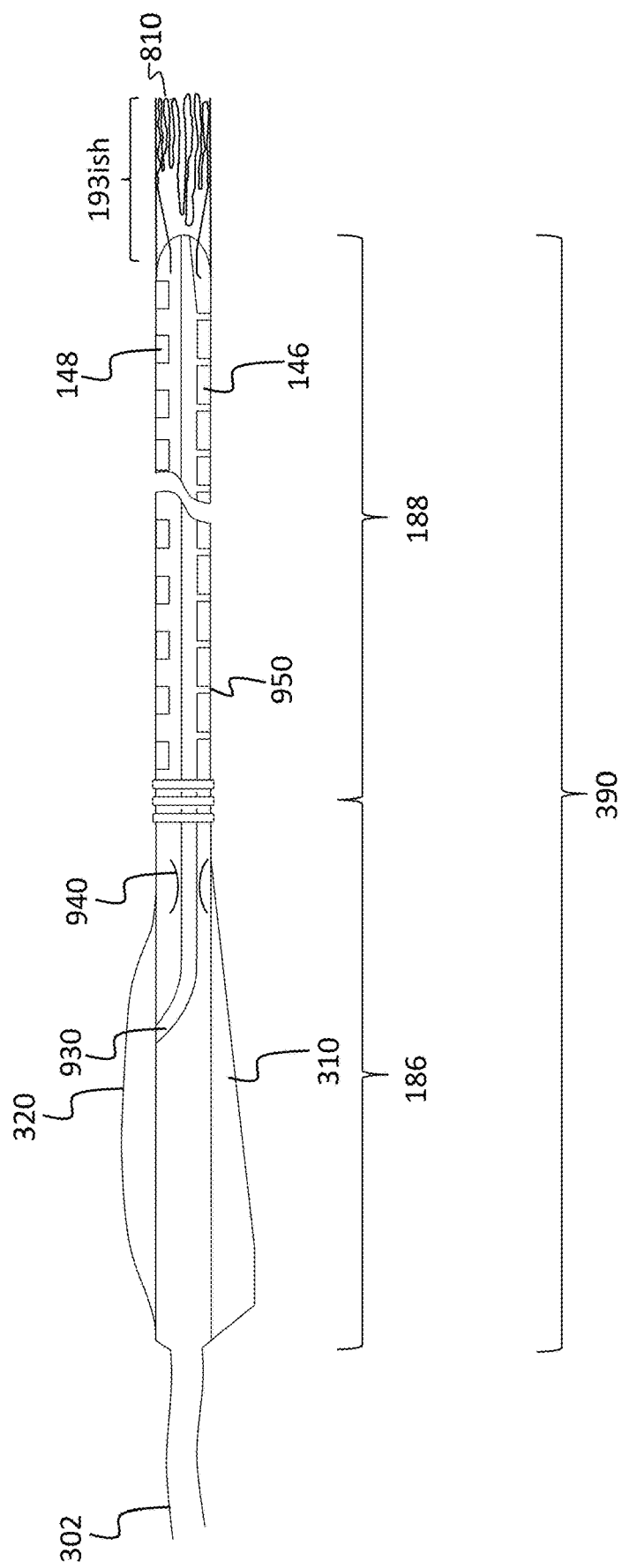
FIG. 19 depicts an exemplary electrode array in combination with a delivery apparatus.

In an exemplary embodiment, the electrode array can be configured to also deliver therapeutic substance along the length were at least along a portion of the length or at various locations thereof, so that the locations in the cochlea proximate electrode array are also provided directly with therapeutic substance, as opposed to only the locations where the delivery apparatus is located, which would "skip" the locations that are in the basal direction of the distal end of the electrode array. In this regard, FIG. 19 presents such an exemplary embodiment, where there is a traditional electrode array as seen, that includes electrodes 148 arrayed along the carrier 149. These electrodes are in signal communication with lead assembly 302, which extends to the receiver stimulator the implant in the traditional manner. In this exemplary embodiment, the reservoir 320, which is represented in a deflated or otherwise substantially empty state, relative to that which is shown in the figures above, is in fluid communication with conduit 930, which includes a flow restrictor 940 which can be in the form of a valve which can meet or otherwise turn one or off the flow of therapeutic substance from the reservoir to the downstream side of the conduit relative to the flow restrictor 940. The conduit 930 extends along the length of the carrier 149, and includes outlets 950 located along the length thereof. In some embodiments, these outlets are not present, and/or the outlets may be staggered or arrayed in a different manner (there may be no outlets at the basal location or fewer outlets of the basal location, etc.). The conduit 930 extends to section 193*ish*, which section includes the pre-deployed delivery apparatus 810 in accordance with the teachings detailed above by way of example. In an exemplary embodiment, the outlets 950 can be temporarily sealed so as to enable sufficient increase in pressure to deploy the delivery apparatus 810. In an exemplary embodiment, dissolvable plugs can be located in the opening 950, which plugged will dissolve when exposed to the perilymph. While the plugs are in place, the therapeutic substance will not be able to escape the electrode array, and thus the flow therapeutic substance will expand the delivery apparatus 810 in accordance with the teachings detailed above. The plugs can be relatively rapidly dissolving plugs, so that within a short time after the deployments of the delivery apparatus 810, therapeutic substance can be delivered through the outlets 950. Still, as noted above, in at least some exemplary embodiments, outlets 950 are not located along the carrier 149.

In an exemplary embodiment, there is an apparatus detailed herein, wherein the means for delivering (note that the portions of the electrode array by itself does not constitute a means for delivering therapeutic substance as that is used herein, as that is a prior design—however, the combination of the electrode array, with or without the outlets 950, plus the delivery device 810, would constitute a means for delivering) is a means for delivering therapeutic substance to a cochlea directly to tissue locations extending over a 90, 135, 180, 210, 250, 270, 300, 330, 360, 390, 425, 450, 500, 550, 600, 650, 700, 720, 750, 800, or 850 or greater degree turn of the cochlea and/or over any of the angles detailed herein. It is briefly noted that if the means for delivering directly to tissue locations extends over a 90° area, it can extend over a greater than 90° area as well. Providing that the therapeutic substance is delivered directly to the tissue over that aforementioned area, such is within the scope. By "directly to tissue locations," it is meant that there is effectively no need for the perilymph to travel any substantial distance in the longitudinal direction for the therapeutic substance to reach the tissue of the cochlea. Put another way, the deficiencies of the prior art are such that because of the limitations of the ability of the drug delivery system to reach portions of the cochlea, locations of the cochlea that are more apical from the end of the delivery system may not be treated in an efficacious manner. Here, there are few, if any, tissue locations that are "shadowed" by the delivery apparatus that are not efficaciously treated during the use of the delivery device 390.

In an exemplary embodiment, the openings are arrayed such that the therapeutic substance need not travel more than 0.5, 1, 1.5, 2, 2.5, 3, 3.5, 4, 4.5, 5, 5.5, 6, 6.5, 7, 7.5, 8, 8.5, 9, 9.5, or 10 mm or any value or range of values therebetween in 0.05 mm increments in the longitudinal direction from a given opening to reach the tissue of the cochlea with the exception of tissue located more apical from the most distal end of the delivery apparatus.

Corollary to the above, in an exemplary embodiment, the means for delivering is a means for delivering therapeutic substance to a cochlea directly to tissue locations extending along at least a portion of a duct of the cochlea, and the means for delivering is configured to effectively provide a uniform dissolution of therapeutic substance to local locations proximate local locations of the means for delivering to take into account the taper of the cochlea. In this regard, the cochlea narrows with location further towards the apical end. Accordingly, the local volume relative to the delivery apparatus changes with location along the delivery apparatus. In at least some exemplary embodiments, their utilitarian value with respect to having an even or relatively even distribution of therapeutic substance in the perilymph. Accordingly, less therapeutic substance would be needed to be delivered at the locations that are narrower relative to the locations that are wider, all things being equal. This can be achieved, for example, by utilizing smaller openings and/or fewer openings the further along the longitudinal length of the delivery apparatus the openings are located.

In an exemplary embodiment, the resulting therapeutic substance concentration per unit volume of perilymph is within 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80% or any value range of values therebetween in 0.1% increments of one another for any given location relative to any other given location of equal length along the cochlea (e.g., a location that takes up 7 mm of longitudinal length along the duct of the cochlea as compared to another location that also takes up 7 mm of longitudinal length along the duct of the cochlea, a location that takes up 4 mm of longitudinal length as compared to another location that also takes up 4 mm of longitudinal length, etc.), where the largest concentration for a given location is the control (e.g., if the largest concentration is 10 units, the concentration in the other location where the concentrations are within 10% would be either 9 units or 11 units, etc.).

In an exemplary embodiment, the means for delivering is a means for delivering therapeutic substance to a cochlea directly to tissue locations extending along at least a portion of a duct of the cochlea and the means for delivering is configured to provide therapeutic substance directly locally to apical portions of the cochlea and is configured to not provide therapeutic substance directly to basal portions of the cochlea. In this regard, in an exemplary embodiment, there are no openings along the proximal portions of the delivery apparatus 810, but there are openings along the more distal portions of the delivery apparatus 810. An exemplary embodiment of this embodiment is such as where the electrode array supports the delivery apparatus 810 at the tip of the electrode array, as seen in the embodiment of FIG. 19, and where, for example, there are or are not outlets 950 (again, the combination of FIG. 19 falls within the means for delivering therapeutic substance, but if there was only the device to the left of section 193*ish*, that would not be a means for delivering, as that is a prior device).

In an exemplary embodiment, the means for delivering therapeutic substance is configured to movably extend into the cochlea while the means for fixing is fixed to tissue, and wherein the apparatus includes an indicator to indicate a distance of extension of the means for delivering into the cochlea from outside the cochlea.

The embodiments detailed above have been presented in terms of deploying of the delivery apparatus 810. Conversely, it is noted that in an exemplary embodiment, the delivery apparatus 810 can be underemployed/retracted back into tube 1020, at least partially. Some additional details of this will be described below.

Figure 20:
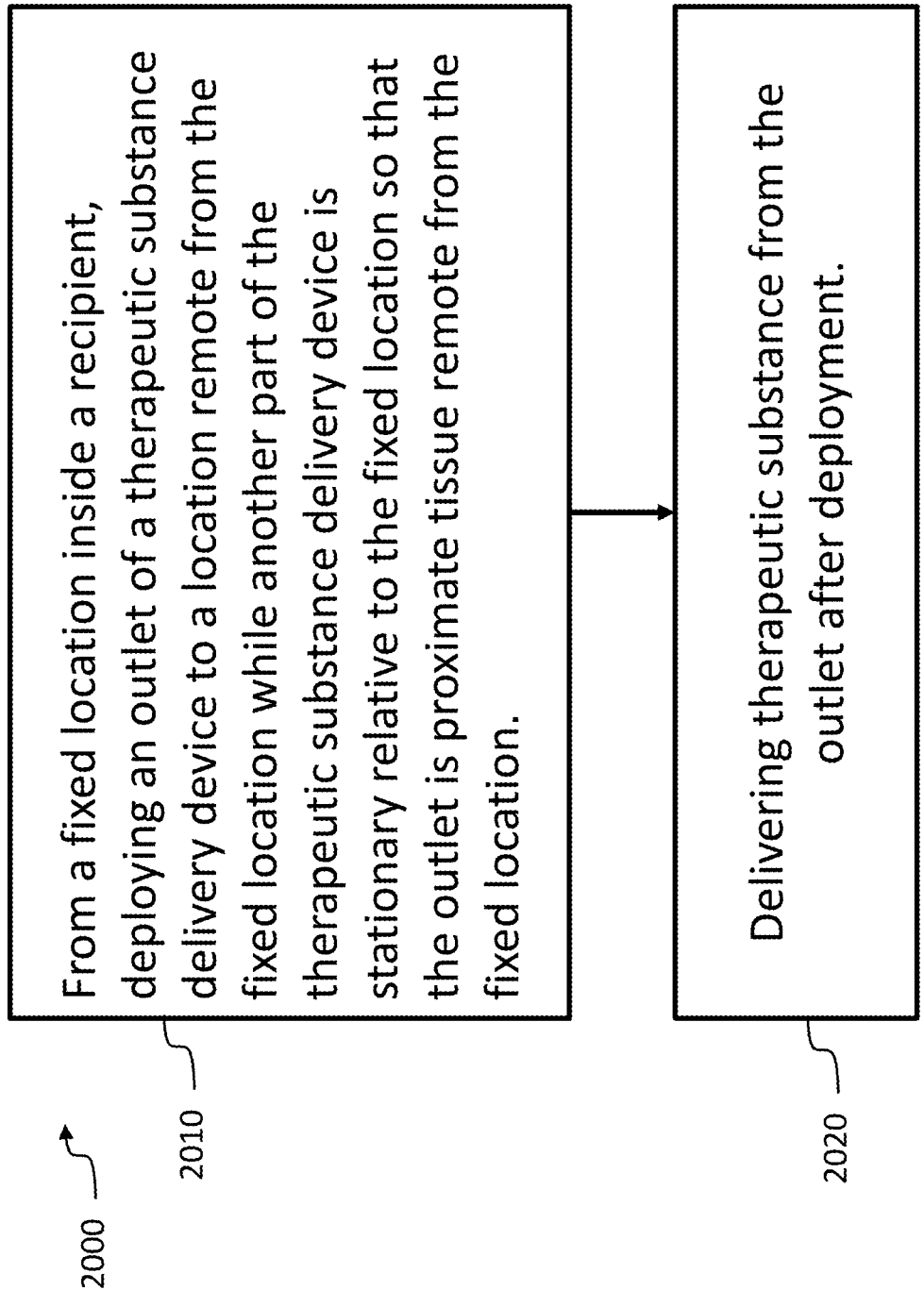
FIGS. 20 and 21 present exemplary flowcharts for exemplary methods.

FIG. 20 presents an exemplary method according to an exemplary embodiment, method 2000. Method 2000 includes method action 2010, which includes, from a fixed location inside a recipient, deploying an outlet of a therapeutic substance delivery device to a location remote from the fixed location while another part of the therapeutic substance delivery device is stationary relative to the fixed location so that the outlet is proximate tissue remote from the fixed location. It is noted that in this exemplary method, the delivery device need not be secured to the fixed location. The phrase "fixed location" refers to tissue or the like that does not move relative to the rest of the body. That said, in an exemplary embodiment of this method, the delivery device 390 can indeed be fixed to the fixed location consistent with the teachings detailed above.

Method 2000 further includes method action 2020, which includes delivering therapeutic substance from the outlet after deployment. This can be performed according to any of the teachings detailed herein and/or variations thereof.

In an exemplary embodiment of method 2000, an exemplary embodiment of method 2000, the action of deploying an outlet includes unfurling a tube in a duct of a cochlea so that the duct of the cochlea guides the tube such that the tube extends in the cochlea in a turning manner that extends at least 90, 135, 160, 180, 210, 225, 250, 275, 300, 330, 360, 390, 420, 450, 475, 500, 525, 550, 575, 600, 625, 650, 675, 700, 725, 750, 775, 800, or 825 or more degrees, or any value or range of values therebetween in 1° increments. The unfurling can be in accordance with any of the teachings detailed herein. Also, while the embodiments of FIG. 11 depicts the tube 810 "bunched up," in an alternate embodiment, the two can be coiled, and can "roll out," which would also constitute unfurling. This as opposed to being blown up like a balloon/simply expanding in the lateral direction, which would not be unfurling.

In an exemplary embodiment of method 2000, the action of deploying an outlet includes extending a component of the delivery device in a cochlea of a recipient in a turning manner that extends at least any of the angle values noted above. Also, there are a plurality of outlets along the component through which the therapeutic substance is delivered, such that an effectively even therapeutic substance concentration is results over the at least any of the values detailed above. In an exemplary embodiment of method 2000, the action of deploying an outlet includes extending a component of the delivery device in a cochlea of a recipient in a turning manner that extends at least any of the angle values noted above. Also, there are a plurality of outlets along the component through which the therapeutic substance is delivered, such that an effectively even therapeutic substance concentration is results over less than the at least any of the values detailed above, which could be less than 90, 85, 80, 75, 70, 65, 60, 55, 50, 45, 40, 35, 30, 25, 20, 15, 10, or 5% or less, or any value or range of values therebetween in 1% increments relative to the total angle at issue.

In an exemplary embodiment of method 2000, the action of deploying an outlet includes extending a component of the delivery device in a cochlea of a recipient in a turning manner that extends at least 540 degrees, there are at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 100, 125, 150, 175, 200, 225, 250, 275 or 300 or more discrete outlets along the component through which the therapeutic substance is delivered.

In an exemplary embodiment, the action of delivering therapeutic substance from the outlet of method 2000 is executed by increasing a pressure inside the therapeutic substance delivery device so that the outlet changes shape in a manner that enables the therapeutic substance to travel through the outlet at a rate at least substantially higher than that which is the case prior to the shape change, and a sustained therapeutic substance delivery release rate is controlled by controlling the pressure. In an exemplary embodiment, the action of delivering therapeutic substance from the outlet of method 2000 is executed by increasing a pressure inside the therapeutic substance delivery device so that the outlet effectively does not change shape in a manner, and/or the therapeutic substance travels through the outlet at a rate effectively equal to that which is the case prior to the increase in pressure, and a sustained therapeutic substance delivery release rate is achieved unrelated to the pressure.

In at least some exemplary embodiments, the outlet is moved to a location inside a cochlea of the recipient, and the action of delivering therapeutic substance is executed via the establishment of a concentration gradient that transports the therapeutic substance through the outlet. In some embodiments, an initial pressure differential is utilized to extend the delivery apparatus 810, and in the pressure differential can be removed or otherwise lowered. In at least some exemplary embodiments, the concentration gradient exists at pressures that are about the same with respect to inside the delivery apparatus 810 and outside delivery apparatus 810. In an exemplary embodiment, the pressure differential between the inside and the outside, is such that the pressure on the outside is within 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50% of the value of the pressure on the inside, for 20, 21, 22, 23, 24, 25, 30, 35, 40, 45, 50, 55, 60, 65, 70, 75, 80, 85, 90, 91, 92, 93, 94, 95, 96, 97, 98, 99, or 100% of the time that therapeutic substance is being delivered in an efficacious manner and/or for the aforementioned percentages with respect to the total mass and/or the total volume of the therapeutic substance delivered.

In an exemplary embodiment, the pressure on the inside of the delivery apparatus 810 can in some instances be lower than the pressure on the outside, so as to draw in perilymph or other body fluids so as to establish an exchange with the body fluids of the therapeutic substance, which would then leave the delivery apparatus 810 with the therapeutic substance. In this regard, pressure changes can be positive and negative to move the body fluids in and out of the tube 810.

Consistent with the teachings above, the outlet is in a flexible tube, and the action of deploying the outlet includes moving therapeutic substance into the tube from a location outside the tube, thereby moving the outlet to the location remote from the fixed location, and the tube is configured such that in the absence of the therapeutic substance or another pressurizing fluid, the tube would not support its own weight. This would be evaluated in a fluid that is or reflects perilymph, or whatever is the body fluid associated with the method.

Figure 21:
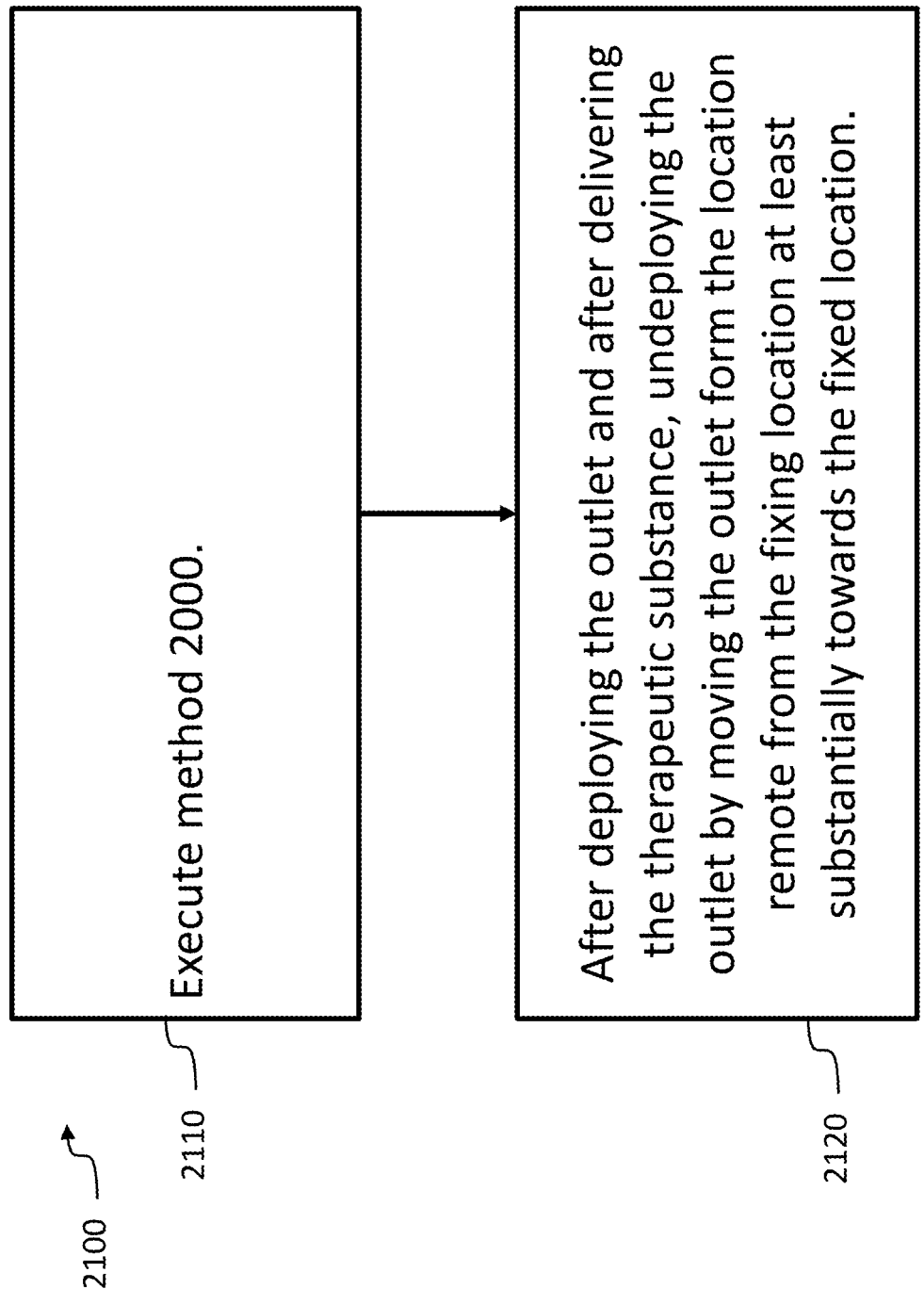

FIG. 21 presents a flowchart for an exemplary method, method 2100, which includes method action 2110, which includes executing method 2000. Method 2100 further includes method action 2120, which includes, after deploying the outlet and after delivering the therapeutic substance, undeploying the outlet by moving the outlet from the location remote from the fixing location at least substantially towards the fixed location.

Deploying and undeploying might be also be executed in conjunction with an acute setting or only with such or only with a chronic setting or both. An exemplary scenario could be minimally invasive intra-tympanic approach where a surgeon would place the catheter through the tympanic membrane onto the round window, deploy the tube into the cochlea (through the round window, for example, or any other appropriate orifice), deliver a therapeutic substance, then undeploy the tube straight away (or within any of the timeframes herein), then remove the entire therapeutic substance delivery device 390 or other device. Undeploying to collapse the tube 810 could be executed by way of example only and not by way of limitation, by "sucking" back into the catheter or tube 1020. In an exemplary embodiment, this can have more utility with respect to safety of the like that if the device was simply pulled out after delivery of therapeutic substance, and such can have utilitarian value in a scenario where, for example, the devices deployed for more than a half a turn, or thereabouts.

In some embodiments, less, than, greater than or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 75, 90, 120, 160, 250, 300, 400, 500, 600, 700, 800, 900, 1000, 1100, 1200, 1300, 1400 or 1500 minutes or any value or range of values therebetween in 1 second increments, or less than or greater than or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 75, 90, 120, 160, 250, 300, 400, 500, 600, 700, 800, 900, 1000, 1100, 1200, 1300, 1400, or 1500 days, or weeks, or any value or range of values therebetween in 0.1 day increments elapses between the action of deploying and the action of undeploying and/or withdrawing the delivery device 390 from the cochlea, and the method further comprises, after at least any of the above noted timeframes, from the undeploying, again deploying the outlet and delivering therapeutic substance from the outlet and then reundeploying the outlet. In an exemplary embodiment, any of the aforementioned times can be the times between the action of deploying the action of delivering therapeutic substance (beginning, end, or mid point (mean, medium, or mode, with respect to time or volume or mass) and/or any of the aforementioned times can be the times between the action of delivering therapeutic substance (beginning, end, midpoint, etc.), and the undeployment. The time of therapeutic substance delivery can be any of the times detailed above. Any of the times detailed above can be the time from the insertion/implantation, of a another implant, such as a cochlear implant or a middle ear implant, etc., and the deployment and/or the delivery of the therapeutic substance, etc.

In an exemplary embodiment of these methods, the outlet is a flexible tube, and during the action of deployment, the flexible tube is in fluid communication with a catheter that is in fluid communication with a reservoir containing the therapeutic substance, wherein the action of delivering therapeutic substance includes moving the therapeutic substance from the reservoir, through the catheter to the flexible tube, and any of these methods can, in some embodiments, further comprise detaching the catheter from the tube after delivery of the therapeutic substance, and removing the catheter from the recipient.

FIG. 15 presents some exemplary details of some exemplary embodiments. In an exemplary embodiment, D1 can be less than, greater than, or equal to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mm or more, or any value or range of values therebetween in 0.01 mm increments (e.g., 22.22 mm, 25.17 mm, 17.04 mm to 23.23 mm, etc.). It is noted that in some embodiments, D1 is limited by the "unspiraled" length of the cochlea, in that in at least some exemplary embodiments, the design is such that the tip of the delivery apparatus 810 will not reach the apical end of the cochlea spiral. Conversely, in some embodiments, additional length is added so as to increase the likelihood or otherwise ensure that the tip reaches about as far as possible within the cochlea. Thus, there can be some "extra material," and thus extra length, roughly analogous to having more heat shield than one specifically needed on the Apollo 11 reentry capsule.

D2 can be less than, greater than or equal to 0 (in for example an embodiment where the seal 1005 extends out of the end of the tube 1020), 0.1, 0.2, 0.3, 0.4, 0.5, 0.6, 0.7, 0.8, 0.9, 1, 1.5, 2.0, 2.5, 3, 3.5, 4, 4.5, 5, 5.5, 6, 6.5, 7, 8, 9, 10, 11, 12, 13, 14, 15, 16, 17, 18, 19, 20, 21, 22, 23, 24, 25, 26, 27, 28, 29, 30 mm or more or any value or range of values therebetween in 0.01 mm increments. In this regard, in at least some exemplary embodiments, D2 is a value that provides utilitarian value with respect to providing a space sufficient to retain or otherwise contain at least an effective portion of the delivery apparatus 810 in the undeployed state. In the embodiments depicted above, it is envisioned that at least a portion of the delivery apparatus 810 is located out board of the seal 1005, as seen in FIG. 11. However, as also can be seen in FIG. 11, at least some of the delivery apparatus 810 is located in board in the undeployed state. In some exemplary embodiments, by mass and/or by length, less than, greater than, or equal to 0, 5, 10, 15, 20, 25, 30, 35, 40, 45, 50, 55, 60, 65, 70, 75, 80, 85, 90, 95, or 100 percent, or any value or range of values therebetween in 0.1% increments is located inboard or outboard of the outboard and/or inboard most portion of the seal 1005 in the undeployed state. Also, as seen in the figures, the delivery apparatus 810 is attached to the seal at the outboard face, and thus as shown in the figures, when fully deployed, 100% of the delivery apparatus 810 is located outboard of the inboard face of the seal, and at least effectively 100% of the delivery apparatus 810 located outboard of the outboard face of the seal, when fully deployed. In at least some exemplary embodiments, when fully deployed (where "fully deployed" refers to the maximum distance of deployment without anything stopping such, such as the cochlea wall—this is the distance that would extend in free space or in a large volume of liquid without constraints) by mass and/or by length, less than, greater than or equal to 50, 55, 60, 65, 70, 75, 80, 85, 90, 95 or 100 percent or any value or range of values therebetween in 0.1% increments is located inboard or outboard of the outboard and/or inboard most portion of the seal 1005. That said, in an exemplary embodiment where, for example, walls of the cochlea restrict the full deployment of the delivery apparatus 810, an exemplary embodiment, by mass and/or by length, less than, greater than or equal to 20, 25, 30, 35, 40, 45, 50, 55, 60, 65, 70, 75, 80, 85, 90, 95 or 100 percent or any value or range of values therebetween in 0.1% increments is located inboard or outboard of the outboard and/or inboard most portion of the seal 1005 when deployed to the maximum distance in a cochlea (as differentiated from full deployment—note that the two can be the same, depending on the geometries of the cochlea and the delivery apparatus 810).

In view of the above, in at least some embodiments of the apparatuses disclosed herein, the apparatus is an inner ear therapeutic substance delivery apparatus, and the above detailed/noted second structure is configured to expand in a longitudinal direction from the above detailed noted first structure by at least or no more than or equal to 1, 2, 3, 4, 5, 6, 7, 8, 8, 10, 11, 12, 13, 14, 15, 16, 17, 18, 19 or 20 mm or any value or range of values therebetween in 0.1 mm increments. In view of the above, in at least some embodiments of the apparatuses disclosed herein, the apparatus is an inner ear therapeutic substance delivery apparatus, and the above detailed/noted second structure is configured to expand in a longitudinal direction from the above detailed noted first structure by at least or no more than or equal to 1, 2, 3, 4, 5, 6, 7, 8, 8, 10, 11, 12, 13, 14, 15, 16, 17, 18, 19, 20, 21, 22, 23, 24, 25, 26, 27, 28, 29 or 30 mm or any value or range of values therebetween in 0.1 mm increments.

In view of the above, in at least some embodiments of the apparatuses disclosed herein, the apparatus is a therapeutic substance delivery apparatus, whether it is for the inner ear or another part of the body (again, the teachings herein can be used for other areas of treatment other than the inner ear, and the above detailed/noted second structure is configured to expand in a longitudinal direction from the above detailed noted first structure by at least or no more than or equal to 1, 2, 3, 4, 5, 6, 7, 8, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 56, 47, 48, 49, 50, 51, 52, 53, 54, 55, 56, 57, 58, 59, 60, 65, 70, 75, 80, 85, 90, 95, 100, 125, 25, 175, 200, 225, 250, 275 or 300 mm from the most distal end of the first structure.

In an exemplary embodiment, the apparatuses detailed herein can be an inner ear therapeutic substance delivery apparatus, or any other delivery apparatus for that matter, and the above noted second structure is configured to expand in a longitudinal direction from the above noted first structure by at least 1, 1.5, 2, 2.5, 3, 3.5, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 times or more a distance that the second structure overlaps with the first structure when supported by the first structure prior to deployment. (If the distance of overlap is zero, it will be greater than 50 times because of division by zero.) In this regard, if D99 is 3 mm, and D1 minus D2 is 30 mm, that that would be 10 times expansion.

In an exemplary embodiment, the delivery apparatus 810 is not a filter as that would be understood in this art. Also, in an exemplary embodiment, the flow rate is essentially entirely controlled by the overall device, as opposed to the outlets and/or the structure of the delivery apparatus 810.

In at least some exemplary embodiments, the tube 1020 is inserted into the cochlea a variable distance in some embodiments. In some embodiments, the delivery device 930 is configured with a stop to prevent the tube 1020 from being inserted a further distance into the cochlea from where the stop hits, for example, the bony wall that is the interface between the interior in the middle ear. In other embodiments, the delivery device 930 is not configured with a stop, and the tube 1020 or any other pertinent components of delivery device 930 can be inserted any distance that is desirable or otherwise having utilitarian value, subject to the limitations of the interior contours of the cochlea. Thus, in an exemplary embodiment, the tube 1020 can be inserted to a location proximate the first turn of the cochlea, or even beyond that (where tube 1020 can be a flexible tube). In this regard, in at least some exemplary embodiments, depending on the geometry of the delivery apparatus 810, the delivery apparatus 810 can be deployed to the maximum distance in the cochlea but not fully deployed because the end of the cochlea would be reached prior to full deployment, such as, for example, if the tube 1020 was inserted a relatively far distance into the cochlea relative to other scenarios of insertion.

In view of the above, in at least some exemplary embodiments, there can be utilitarian value with respect to locating the proximal end of the delivery apparatus 810 as far into the cochlea as possible before deployment, or at least a given distance into the cochlea from the bony wall/the wall that establishes the demarcation between the basal end of the cochlea in the middle ear. Indeed, in this regard, in an exemplary embodiment, D6 can be the distance from the end of the tube 1020 to a stop, or to the outboard/distal most portion of the cochlea interface section. Also, D6 can be a distance from the outside surface of the cochlea in the middle ear, where D6 is used to gauge distances in measurements, as opposed to structure (note that all of the dimensions herein can be that which results from methods of utilizing the teachings detailed herein, as well as structural features of some embodiments). D6 can be less than, greater than or equal to 0, 0.25, 0.5, 0.75, 1, 1.25, 1.5, 1.75, 2, 2.5, 3, 3.5, 4, 4.5, 5, 5.5, 6, 6.5, 7, 8, 9, 10, 11, 12, 13, 14, 15, 16, 17, 18, 19, 20, 21, 22, 23, 24, 25, 26, 27, 28, 29 or 30 mm or more or any value or range of values therebetween in 0.01 mm increments In some exemplary embodiments, markers, gauge readings, etc., are located on the outside of the tube 1020 or other pertinent component of the delivery device 930 so as to enable the surgeon or other healthcare professional to determine how far end of the tube 1020 has been inserted into the cochlea.

D3 can be less than, greater than or equal to 0.05, 0.1, 0.15, 0.2, 0.25, 0.3, 0.35, 0.4, 0.45, 0.5, 0.6, 0.7, 0.8, 0.9, 1.0, 1.1, 1.2, 1.3, 1.4, 1.5, 1.6, 1.7, 1.8, 1.9 or 2 mm or more or any value or range of values therebetween in 0.01 mm increments, subject to the diameter of the given cochlea (some of the latter values may not be feasible for a human cochlea). In an exemplary embodiment, D7 is 1.0, 1.1, 1.2, 1.3, 1.4, 1.5, 1.6, 1.7, 1.8, 1.9, 2, 2.25, 2.5, 2.75, 3, 3.25, 3.5, 3.75, 4, 4.5, 5, 5.5, 6, 6.5, 7, 7.5, 8, 8.5, 9, 9.5, 10, 11, 12, 13, 14 or 15 or more times D3.

In an exemplary embodiment, D4 and/or D5 can be less than, greater than or equal to 0 (in the case where the opening is completely closed) 0.05, 0.1, 0.15, 0.2, 0.25, 0.3, 0.35, 0.4, 0.45, 0.5, 0.6, 0.7, 0.8, 0.9, 1.0, 1.1, 1.2, 1.3, 1.4, 1.5, 1.6, 1.7, 1.8, 1.9 or 2 mm or more or any value or range of values therebetween in 0.01 mm increments, in its fully open state (design wise—this may not be how open the outlets can be during normal use—conversely, these values could be openings that exist during methods of use).

As seen in FIG. 15, the openings 820 can be aligned along the longitudinal direction of the delivery apparatus 810 with one another, and/or can be offset from one another with respect to location about the longitudinal axis on the surface of the delivery apparatus 810. Any spatial orientation and/or geometry that can enable the teachings detailed herein can be utilized in at least some exemplary embodiment. Any order can be used as well.

In exemplary embodiment, the openings are arranged, sized, dimensioned and/or located to address the overall features associated with the delivery system. In this regard, larger openings might be utilized at locations further distal of the delivery apparatus 810 to address the fact that the pressure and/or mass and/or mass flow rate within the delivery apparatus 810 could be lower with location along the longitudinal axis towards the distal end relative to location more proximal because of the openings that are located more proximal than the distal openings. Conversely, in at least some exemplary embodiments, the system can be configured such that the pressure is about effectively the same along the entire length, due to, for example, over pressure, and thus in at least some exemplary embodiments, the openings will be the same along the length and located potentially equidistant from one another. That said, because of the nature of the cochlea, which tapers with respect to location from the basal and to the apical end, and thus the volume (the local volume) decreases with location toward the apical end, the openings may be sized, dimensioned and/or located to address this phenomenon (e.g., the local flow rate at locations towards the basal end may be utilitarianly higher than at locations towards the apical end, because, for example, there is less perilymph to "dilute" the therapeutic substance at the apical locations because there is locally a smaller volume at the apical locations). Any arrangement that can enable utilitarian value with respect to application of local therapeutic substance within the cochlea can utilize at least some exemplary embodiments.

FIG. 22 presents another exemplary embodiment, where the spacing between the openings 820 is larger than that of some of the embodiments detailed above, and there are fewer openings than that of the above. FIG. 23 depicts another exemplary embodiment, where the spacing of the openings between one another is different over the length of the delivery apparatus 810 relative to the other embodiments detailed herein. FIG. 24 presents yet another exemplary embodiment having different size openings in different spacings of the openings 820.

FIG. 25 presents another exemplary embodiment where the delivery apparatus 810 is tapered. Here, the tapering is basically linear. FIG. 26 presents another exemplary embodiment that includes some tapering of the delivery apparatus 810. Here, the tapering is limited to certain sections but not others. The tapering can provide for the difference therapeutic substance delivery is disclosed herein for different locations along the length of the delivery apparatus to take into account the fact that the cochlea is with varies along the length thereof. The tapering can thus provide a delivery apparatus 810 that has a variable inside diameter. The effect can be, for example, an effect that is similar with respect to HVAC systems where the ducting has a reduced interior cross sectional area further downstream of the system.

FIGS. 27-29 present an exemplary embodiment with a device that opens and outlet 2929 upon the delivery apparatus 810 reaching a certain length. FIGS. 27 to 29 depict extension of the delivery apparatus 810 over time. As can be seen in FIG. 27, initially, the tether 2777 is generally loose with in the delivery apparatus 810. Then, in FIG. 28, the tether 2777 becomes taut with additional extension of the delivery apparatus 810, at least relative to that depicted in FIG. 27. Here, plug 2727 is seen attached to the distal end of the tether 2777. Relative to FIG. 28, the delivery apparatus 810 extends even further as seen in FIG. 29. Because the tether 2777 is taut, the plug 2727 is pulled out of the outlet 2929. This enables the therapeutic substance to be delivered out outlet 2929 in a longitudinal direction. This can have utilitarian value with respect to reaching portions of the cochlea that are apical of the end of the therapeutic substance delivery apparatus 390. This can also have utilitarian value with respect to ensuring that the pressure increase or the flow increase, etc., into the delivery apparatus 810, which is used to extend the delivery apparatus, is not "wasted" or otherwise diminished. That is, in this embodiment, greater extension/deployment pressures/forces will exist while the plug 2727 plums the outlet 2929 relative to that which would be the case if the outlet 299 was simply open during the entire deployment regime. Another exemplary embodiment can utilize a dissolvable plug or the like or any of the other plugs herein. In an exemplary embodiment, a sufficient increase in pressure could eject the plug, thus opening the outlet 2929. In an exemplary embodiment, the outlet 2929 can be established by a weakened portion, which tears upon the increase in pressure. In an exemplary embodiment, there could be a pressure that is sufficient to extend the delivery apparatus 810, and then there could be a subsequent increase in pressure that could result in the tearing or the ejectment of the plug, etc. In an exemplary embodiment, the pressure difference and/or flow rate difference and/or mass flow rate, etc., between that needed to fully deploy the delivery apparatus 810, and that which is needed to open the openings herein, can be a scenario where at least and/or no more than a 5, 10, 15, 20, 25, 30, 35, 40, 45, 50, 55, 60, 65, 70, 75, 80, 85, 90, 95, 100, 125, 150, 175, 200, 225, 250, 275, 300 or 400 or 500 or 600 or 700 or 800% or more increase or any value or range of values therebetween in 1% increments is required.

In an exemplary embodiment, a processor or a computing device or a computer can utilize to control the deployment and/or delivery times. In an exemplary embodiment, deployment can be by way of the use of a non-therapeutic substance, such as a saline solution or some other biocompatible fluid. In an exemplary embodiment, this first fluid can be utilized to deploy the delivery apparatus 810. Then, at some time after deployment, the first fluid could then be replaced by a second fluid in the form of the therapeutic substance. This can be controlled by a processor or the like, or could be controlled manually via signals that can be sent to an implanted were semi-implanted or device that is even outside of the recipient. With respect to the embodiment of FIG. 5, in an exemplary embodiment, there could be two reservoirs, one with the saline solution or the inner solution, and in the other reservoir with a therapeutic substance. The two reservoirs can be manifold into the same tube 206.

In some embodiments, opening of the tube 1020 can be slightly inserted into the cochleostomy or round window or oval window incision and fixed in an angle tangential to the scala tympani and held at an angle using, for example, bone cement or a mechanical locking mechanism, etc. (Bone cement can be used to fix the first structure in place.) A controlled process (e.g. pump, syringe—a syringe/piston apparatus can be used in some embodiments) can apply positive pressure to the reservoir and/or to whatever location the therapeutic substance is stored and thus the tube or an area inside the tube (the embodiments above depict the conduit 930 extending to see, but as noted above, in some embodiments, the conduit 930 can actually be the entire tube 1020) that deploys the tube 810, which can be a drug permeable tube, into the perilymph and along the scala tympani towards the apex thereof.

A rate of deployment can be greater than less greater than less than or equal to 1, 2, 3, 4, 5, 6, 7, 8, 9, 10, 11, 12, 13, 14, 15, 20, 25, 30, 35, 40, 45, 50, 55, 60 degrees or any value or range of values therebetween in 0.1° increments per 0.1, 0.2, 0.3, 0.4, 0.5, 0.6, 0.7, 0.8, 0.9, 1, 1.25, 1.5, 1.75, 2, 2.25, 2.5, 2.75, 3, 4, 5, 6, 7, 8, 9, 10, 20, 30, 40, 50, 60, 90, 120, 150, 200, 300, 400 seconds or minutes or any value or range of values therebetween in 0.01 increments.

The sustained drug release rate can be controlled by the positive pressure inside the device. A non-sustained release can also occur in some embodiments.

In some embodiments, the tube 810 is a drug permeable membrane that is effectively a one-way valve which becomes permeable by increasing its pore size due to increased internal pressure. This can avoid, in some embodiments, clotting of the catheter and drug delivery tube due to protein and other organic matter entering the device.

To implant the device, the cochlear can be accessed either minimally invasive through the tympanic membrane or as per standard cochlear implant surgery. The drug delivery tube 810 can be a soft structure which is deployed rather than inserted into the cochlear to minimise damage to native tissue. This can be done for non-CI candidates with substantial residual hearing, in some embodiments. The location of the tube deployment can be in any perilymph or endolymph filled space like Scala Tympani, Scala Vestibuli, Scala, Endosteal, between the spiral ligament and bony capsule, or any other space in the body where controlled drug release over a specified length is desired e.g., the eye. The shape of delivery apparatus 810 can be cylindrical and linear, pre-curved. The apparatus 810 can be a mesh. Some physical properties of the deployable drug delivery tube can be flexible, foldable/collapsible and/or stretchable (stretchability per unit area can be less than, equal to or greater than 10, 15, 20, 25, 30, 40, 50, 60, 70, 80, 90, or 100, 150, 200, 250, 300, 400 or 500% or more or any value or range of values in 1% increments relative to the upstretched area, and such can exist or otherwise occur in any of the embodiments detailed herein).

The delivery rate may be controlled by any, some or all of the following: the membranes permeability for the drug, physical properties membrane like pore size, thickness, polarity, pore size might be controllable by stretching the membrane by increasing the internal pressure. The diffusion rate of the drug can be a function of the drug's concentration gradient across the tube's wall (membrane). Also, concentration differences of the drug can be dissolved in across the tube's wall (membrane). A pressure gradient across the apparatus 810 may be achieved by controlling the internal pressure of the drug reservoir and/or cannula with a pump, by using an osmotic agent such as sodium chloride or the drug itself, by filling a flexible reservoir "balloon," by using a gas (propellant) and/or other mechanical or chemical mean to increase and decrease the internal pressure.

Apparatus 810 can be made from a soft membrane which contains pores or openings that open to release drug containing fluid when stretched. Without filling it with drug solution it would not support its own weight and is therefore impossible to insert into the cochlea. Only when filled with drug solution does it deploy in some embodiments from a catheter/tube 1020 expands (inflates) into the cochlea along the scala tympani from the base towards the apex. Doing so the soft tube will follow the lateral wall of the scala tympani. Using this technique allows for full control of insertion speed by controlling the drug solution pressure and no lateral movements due to hand shaking common to standard manual insertion of electrodes or catheters. The tube will also follow the unique shape of one individual cochlea with minimal pressure on structures like the lateral wall or the basilar membrane at the ceiling of the scala tympani.

It is noted that while some embodiments depicted tube 1020 being inserted into the cochlea, in some other embodiments, the tube 1020 does not enter the cochlea. In an exemplary embodiment, the distal end of the tube 1020 is located between the outside surface in the inside surface of the bony wall that establishes the barrier between the inner ear and the middle ear. In an exemplary embodiment, the distal end of the tube 1020 does not enter the passageway.

It is noted that any disclosure of a device and/or system herein corresponds to a disclosure of a method of utilizing such device and/or system. It is further noted that any disclosure of a device and/or system herein corresponds to a disclosure of a method of manufacturing such device and/or system. It is further noted that any disclosure of a method action detailed herein corresponds to a disclosure of a device and/or system for executing that method action/a device and/or system having such functionality corresponding to the method action. It is also noted that any disclosure of a functionality of a device herein corresponds to a method including a method action corresponding to such functionality. Also, any disclosure of any manufacturing methods detailed herein corresponds to a disclosure of a device and/or system resulting from such manufacturing methods and/or a disclosure of a method of utilizing the resulting device and/or system.

Unless otherwise specified or otherwise not enabled by the art, any one or more teachings detailed herein with respect to one embodiment can be combined with one or more teachings of any other teaching detailed herein with respect to other embodiments, and this includes the duplication or repetition of any given teaching of one component with any like component. Also, embodiments include devices systems and/or methods that explicitly exclude any one or more of a given teaching herein. That is, at least some embodiments include devices systems and/or methods that explicitly do not have one or more of the things that are disclosed herein.

While various embodiments of the present invention have been described above, it should be understood that they have been presented by way of example only, and not limitation. It will be apparent to persons skilled in the relevant art that various changes in form and detail can be made therein without departing from the scope of the invention.

The invention claimed is:

1. An apparatus, comprising:
a therapeutic substance delivery device configured for attachment to a first tissue area internal of a recipient, the delivery device configured to enable movement of a therapeutic substance outlet, via movement of a component of which the outlet is a part, of the delivery device proximate a second tissue area away from the first tissue area after attachment to the first tissue area to deliver a therapeutic substance from the outlet while implanted in the recipient, wherein
the component is stowed, prior to the movement of the component, over a distance less than 30 mm.

2. The apparatus of claim 1, wherein:
the movement includes expanding the component so that the outlet moves with expansion of the component.

3. The apparatus of claim 2, wherein:
the component is a means for expanding; and
the apparatus is configured for implantation into a cochlea of a human.

4. The apparatus of claim 1, wherein:
the movement includes expanding the component so that the outlet moves with expansion of the component, wherein the component is flexible.

5. The apparatus of claim 4, wherein:
expanding the flexible component is not uncurling.

6. The apparatus of claim 1, wherein:
the delivery device includes a catheter configured to transport the therapeutic substance to a fixed location; and
the delivery device is configured to enable transportation of the therapeutic substance from the fixed location to the outlet via the component, wherein the component is different from the catheter.

7. The apparatus of claim 6, wherein:
the therapeutic substance delivery device is configured for implantation into a cochlea of a human; and
the catheter is configured to extend into the cochlea of a human when the delivery device is fully implanted in the cochlea of the human.

8. The apparatus of claim 6, wherein:
the component is a tube.

9. The apparatus of claim 8, wherein:
the tube includes a plurality of outlets, one of which is the therapeutic substance outlet, spaced apart from each other at least along a longitudinal axis of the tube, the outlets configured to enable delivery of the therapeutic substance from the outlets.

10. The apparatus of claim 9, wherein:
the apparatus is configured to deploy the tube from a first position where a majority of the outlets, including the therapeutic substance outlet, are proximate the first tissue area to a second position where the majority of the outlets are located away from the first tissue area.

11. The apparatus of claim 1, wherein:
the apparatus is configured for rigid attachment at the first tissue area, wherein the first tissue area is a location at or proximate a wall of a cochlea that separates an interior of the cochlea from a middle ear of the recipient; and
the apparatus is configured to move the outlet so that the outlet is moved from the first tissue area, inside a duct of the cochlea, to a location that is at least one full cochlea turn from a most basil location of the cochlea, while the apparatus is fixed at the first location.

12. The apparatus of claim 1, wherein:
the component includes a drug permeable membrane that is configured to be deployed in a cochlea and function as a one way filter that becomes permeable to the drug by increasing a pore size of a plurality of pores in the membrane due to tensile forces in the membrane increasing upon at least one of deployment or pressurization of the therapeutic substance to be delivered; and
the outlet corresponds to one or more of the plurality of pores.

13. The apparatus of claim 1, wherein:
the apparatus is only a cochlea therapeutic substance delivery device configured to extend the outlet along a duct of the cochlea; and
the apparatus is configured to variably control a distance of the outlet extension into the cochlea to locate the outlet adjacent a specific location inside the cochlea.

14. The apparatus of claim 1, wherein:
the component is stowed, prior to the movement of the component, over a distance less than 15 mm.

15. An apparatus, comprising:
a first structure configured to be attached to tissue internal of a recipient; and
a second structure configured to be supported by the first structure in an initial state during a first temporal period, and configured to be deployed from the first structure in a deployed state during a second temporal period after the first temporal period, wherein the apparatus is a therapeutic substance delivery device configured to deliver therapeutic substance from the second structure to a location remote from the first structure during and/or after deployment of the second structure, the second structure is at least one of in or controllably placeable in fluid communication with the first structure so that therapeutic substance can travel from the first structure to the second structure, and at least one of:

the second structure includes a plurality of therapeutic substance outlets, wherein a diameter of a first of the plurality of outlets is larger than a diameter of a second of the plurality of outlets, wherein the first of the plurality of outlets is located more distally than the second of the plurality of outlets as a result of deployment from the first structure in the deployed state; or the second structure includes a plurality of diffusion zones spaced apart from one another.

16. The apparatus of claim 15, wherein:
the first structure includes a catheter to channel the therapeutic substance to the second structure; and
at least a portion of the second structure is located in the catheter when the second structure is supported by the first structure prior to deployment.

17. The apparatus of claim 15, wherein:
the first structure includes a catheter to channel the therapeutic substance to the second structure; and
at least a portion of the second structure is located about a portion of the first structure that establishes a conduit of the catheter when the second component is supported by the first component prior to deployment.

18. The apparatus of claim 15, wherein:
the apparatus is an inner ear therapeutic substance delivery apparatus, and the second structure is configured to expand in a longitudinal direction from the first structure by at least 20 mm from the most distal end of the first structure.

19. The apparatus of claim 15, wherein:
the apparatus is an inner ear therapeutic substance delivery apparatus, and the second structure is configured to expand in a longitudinal direction from the first structure by at least 10 times a distance that the second structure overlaps with the first structure when supported by the first structure prior to deployment.

20. The apparatus of claim 15, wherein:
the second structure is a thin-skinned tube that has orifices therein, corresponding to the outlets, through which the therapeutic substance is delivered to the recipient; and
the apparatus is configured to vary a shape of the orifices to control a rate of flow of the therapeutic substance through the orifices to control a therapeutic substance delivery rate to the recipient.

21. The apparatus of claim 15, wherein:
the second structure is a tube that includes membraned walled section(s); and
the therapeutic substance diffuses through the membraned walled section(s) to deliver the therapeutic substance to the recipient.

22. The apparatus of claim 15, wherein:
the second structure is walled tube and the therapeutic substance is combined with the wall of the walled tube; and
the therapeutic substance elutes from the tube to deliver the therapeutic substance to the recipient.

23. The apparatus of claim 15, wherein:
the second structure is dissolvable walled tube and the therapeutic substance is combined with the wall of the walled tube; and the therapeutic substance is delivered to the recipient as the walled tube dissolves.

24. The apparatus of claim 15, wherein:
the apparatus includes a portion made from silicone and/or a portion made from titanium; and
the apparatus is a standalone apparatus separate from a cochlear implant.

25. The apparatus of claim 15, wherein:
the second structure includes the plurality of diffusion zones spaced apart from one another.

26. The apparatus of claim 15, wherein:
the second structure includes the plurality of therapeutic substance outlets, wherein the diameter of the first of the plurality of outlets is larger than the diameter of the second of the plurality of outlets, wherein the first of the plurality of outlets is located more distally than the second of the plurality of outlets as a result of deployment from the first structure in the deployed state.

27. An apparatus, comprising:
a therapeutic substance delivery device configured for attachment to a first tissue area internal of a recipient, the delivery device configured to enable movement of a therapeutic substance outlet, via movement of a component of which the outlet is a part, of the delivery device proximate a second tissue area away from the first tissue area after attachment to the first tissue area to deliver a therapeutic substance from the outlet while implanted in the recipient, wherein
the component is stowed, prior to the movement of the component, in a bunched up and/or rolled up state.

28. The apparatus of claim 27, further comprising:
a refillable reservoir; and
a catheter, wherein
the refillable reservoir is in fluid communication with the catheter, and the catheter is in fluid communication with the component, and
the apparatus is configured such that therapeutic substance contained in the reservoir is delivered to the component via the catheter for delivery by the component.

29. The apparatus of claim 27, further comprising:
a catheter, wherein
the catheter is in fluid communication with the component, and
the apparatus is configured with a second component that enables opening of the cochlea without drilling and/or enables a window of the cochlea to be pierced, thereby providing access to the cochlea for movement of the component into the cochlea and is configured to seal the access location.

30. The apparatus of claim 27, further comprising:
a cochlear implant electrode array of a cochlear implant, wherein
the component is attached at least indirectly to the cochlear implant at a location that is at a distal portion of the electrode array.

31. The apparatus of claim 27, wherein:
the component is configured to deliver therapeutic substance to a cochlea directly to tissue locations extending over a 360 degree turn of the cochlea.

32. The apparatus of claim 27, wherein:
the component is a means for delivering therapeutic substance to a cochlea directly to tissue locations extending along at least a portion of a duct of the cochlea; and
the component is configured to effectively provide a uniform dissolution of therapeutic substance to local locations proximate local locations of the component for delivering to take into account the taper of the cochlea.

33. The apparatus of claim 27, wherein:

the component is a means for delivering therapeutic substance to a cochlea directly to tissue locations extending along at least a portion of a duct of the cochlea; and the component is configured to provide therapeutic substance directly locally to apical portions of the cochlea and is configured to not provide therapeutic substance directly to basil portions of the cochlea.

34. The apparatus of claim 27, wherein:

the component is stowed, prior to the movement of the component, in the bunched up state.

35. The apparatus of claim 27, wherein:

the component is stowed, prior to the movement of the component, in the rolled up state.

\* \* \* \* \*